(12) United States Patent
Kanda et al.

(10) Patent No.: US 6,610,853 B1
(45) Date of Patent: Aug. 26, 2003

(54) N-(PHENYLSULFONYL)PICOLINAMIDE DERIVATIVES, PROCESS FOR PRODUCING THE SAME, AND HERBICIDE

(75) Inventors: Yoichi Kanda, Fukushima (JP); Koki Sato, Fukushima (JP); Tsutomu Sato, Fukushima (JP)

(73) Assignee: Kureha Kagaku Kogyo K.K., Tokyo (JP)

( * ) Notice: Subject to any disclaimer, the term of this patent is extended or adjusted under 35 U.S.C. 154(b) by 0 days.

(21) Appl. No.: 09/601,791

(22) PCT Filed: Feb. 13, 1998

(86) PCT No.: PCT/JP98/00583

§ 371 (c)(1),
(2), (4) Date: Aug. 8, 2000

(87) PCT Pub. No.: WO99/41238

PCT Pub. Date: Aug. 19, 1999

(51) Int. Cl.⁷ .................. C07D 213/81; A01N 43/40
(52) U.S. Cl. ....................... 546/323; 504/244
(58) Field of Search ............. 546/323; 504/244

(56) References Cited

U.S. PATENT DOCUMENTS 5,529,974 A * 6/1996 Kerber .................. 504/112

FOREIGN PATENT DOCUMENTS

| CH | 0365484 | * 10/1989 | ......... C07C/311/51 |
|----|---------|-----------|----------------------|
| GB | 2286589 | * 8/1995  | ......... C07D/215/48 |
| JP | 62-181261 | 8/1987 | |
| JP | 63-57570 | 3/1988 | |
| JP | 10-59942 | 3/1998 | |

OTHER PUBLICATIONS

Morkved, Eva H. and Marshall W. Cronyn. "Potential Acyl Transfer Agents. Reactions of N–Acyl–2–pyridinecarboxamides with Nucleophiles," 1982, Acta Chemica Scandinavia, B36(6), 381–8.*

* cited by examiner

*Primary Examiner*—Alan L. Rotman
*Assistant Examiner*—Janet L Coppins
(74) *Attorney, Agent, or Firm*—McDermott, Will & Emery

(57) ABSTRACT

A herbicide containing as the active ingredient an N-(henylsulfonyl)picolinamide derivative represented by general formula (I) wherein X represents a halogeno, a $C_{1-4}$ alkyl, a $C_{1-4}$ haloalkyl, a $C_{1-4}$ alkoxy, a $C_{1-4}$ haloalkoxy, a ($C_{1-4}$ alkoxy)carbonyl, a [di($C_{1-4}$ alkyl)amino]sulfonyl, an [N—($C_{1-4}$ alkyl)-N—($C_{1-4}$ alkoxy)amino]sulfonyl, a ($C_{1-4}$ alkylamino)sulfonyl, a $C_{1-4}$ alkylthio, a $C_{1-4}$ alkylsulfinyl, a $C_{1-4}$ alkylsulfonyl, or nitro; n is an integer of 0 to 5; Y represets a halogeno, a $C_{1-4}$ alkyl, a $C_{1-4}$ haloalkyl, a $C_{1-4}$ alkoxy, $C_{1-4}$ haloalkoxy, a $C_{1-4}$ alkylthio, a $C_{1-4}$ haloalkylthio, amino, a $C_{1-4}$ alkylamino, a di($C_{1-4}$ alkyl) amino, a ($C_{1-4}$ alkoxy) $C_{1-4}$ alkyl, a ($C_{1-4}$ alkylthio) $C_{1-4}$ alkyl, or nitro; and m is an integer of 0 to 4. This active ingredient is synthesized by condensing a substituted picolinic acid with a substituted benzenesulfonamide under dehydration, or by reacting the phenyl ester of a substituted picolinic acid with a substituted benzenesulfonamide in the presence of a basic compound.

(I)

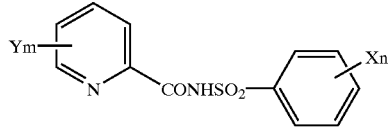

2 Claims, No Drawings

N-(PHENYLSULFONYL)PICOLINAMIDE DERIVATIVES, PROCESS FOR PRODUCING THE SAME, AND HERBICIDE

TECHNICAL FIELD

The present invention relates to N-(phenylsulfonyl)-picolinamide derivatives, a process for producing the same and a herbicide comprising said derivatives as an active ingredient.

TECHNICAL BACKGROUND

The following N-(phenylsulfonyl)picolinamide derivatives have been known heretofore.

N-[(4-Methylphenyl)sulfonyl]picolinamide (U.S. Pat. No. 5,294,610).

N-[(4-Aminophenyl)sulfonyl]picolinamide.

There is however no report that N-(phenylsulfonyl)-picolinamide derivatives can be used as an effective ingredient of herbicides.

By the way, there have conventionally been strong demands for herbicides capable of exhibiting excellent herbicidal activity even at such low application dosages as bringing about advantage of reducing the amount present in the environment, herbicides capable of exhibiting selectivity between crops and weeds irrespective of variations in environmental conditions, herbicides free from crop injury to the second crop in double-cropping, etc.

The present invention has been completed with a view toward meeting such demands as described above.

DISCLOSURE OF THE INVENTION

Accordingly, objects of the present invention are to provide novel compounds exhibiting excellent herbicidal effect, processes for producing the same, and novel herbicides comprising the same compound as the active ingredient.

As the result of various studies in order to find N-(phenylsulfonyl)picolinamide derivatives industrially effective, the present inventors have found that N-(phenylsulfonyl)-picolinamide derivatives have high herbicidal effect, and thus the present invention has been completed.

The present invention has the following constituent features.

The first invention relates to a herbicide comprising an N-(phenylsulfonyl)picolinamide derivative of the following formula (I) as the active ingredient:

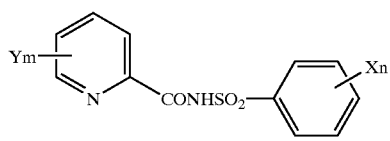

(I)

wherein X represents halogen atom, C1–C4 alkyl group, C1–C4 haloalkyl group, C1–C4 alkoxy group, C1–C4 haloalkoxy group, (C1–C4 alkoxy)carbonyl group, (di-C1–C4 alkylamino)sulfonyl group, [N—(C1–C4 alkyl)-N—(C1–C4 alkoxy)amino]sulfonyl group, (C1–C4 alkylamino)sulfonyl group, C1–C4 alkylthio group, C1–C4 alkylsulfinyl group, C1–C4 alkylsulfonyl group or nitro group, n is an integer of 0–5. In case of n being 2 or more, each X may be identical or different, Y represents halogen atom, C1–C4 alkyl group, C1–C4 haloalkyl group, C1–C4 alkoxy group, C1–C4 haloalkoxy group, C1–C4 alkylthio group, C1–C4 haloalkylthio group, amino group, C1–C4 alkylamino group, di-C1–C4 alkylamino group, (C1–C4 alkoxy) C1–C4 alkyl group, (C1–C4 alkylthio) C1–C4 alkyl group or nitro group, m is an integer of 0–4, and each Y may be identical or different in case of m being 2 or more.

The second invention relates to a process for producing an N-(phenylsulfonyl)picolinamide derivative of the following formula (I) which comprises condensing a substituted picolinic acid of the formula (II) with a substituted benzenesulfonamide of the formula (III) under dehydration, which is shown in the following reaction formula (The first process for production):

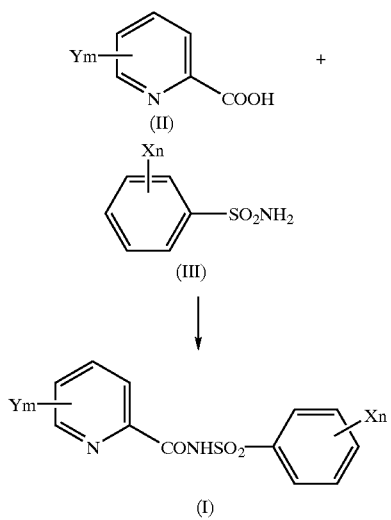

wherein X, Y, n and m are each the same definition as described above.

The third invention relates to a process for producing an N-(phenylsulfonyl)picolinamide derivative of the formula (I) which comprises reacting a substituted picolinic phenyl ester of the formula (IV) with a substituted benzenesulfonamide of the formula (III) in the presence of a basic compound, which is shown in the following reaction formula (the second process for production).

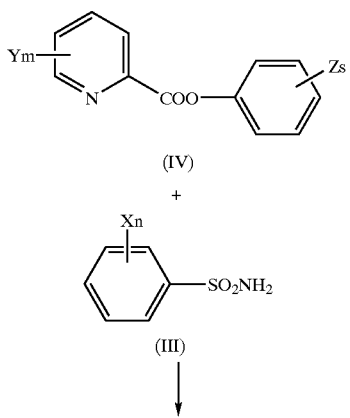

-continued

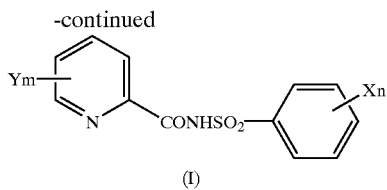

(I)

wherein X, Y, n and m are each the same definition as described above,

Z represents halogen atom, C1–C4 alkyl group, C1–C4 alkoxy group or nitro group, s is an integer of 0–5, and each Z may be identical or different in case of s being 2 or more.

The fourth invention relates to an N-(phenylsulfonyl)-picolinamide derivative of the following formula (I):

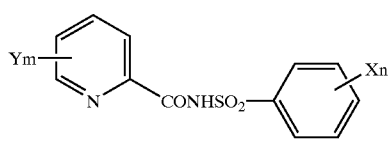

(I)

wherein X, Y, n and m are each the same definition as described above, exclusive of N-[(4-methylphenyl)sulfonyl]picolinamide.

BEST MODE OF PRACTICING THE INVENTION

The present invention will be illustrated in detail in the following.

The groups X and Y of the N-(phenylsulfonyl) picolinamide derivatives of the above-described formula (I) according to the present invention include the following typical substituents, and n and m are preferred to be the following values.

Regarding X:

Fluorine atom, chlorine atom and bromine atom as the halogen atom.

Methyl group as the C1–C4 alkyl group.

Trifluoromethyl group as the C1–C4 haloalkyl group.

Methoxy group as the C1–C4 alkoxy group.

Trifluoromethoxy group as the C1–C4 haloalkoxy group.

Methoxycarbonyl group as the (C1–C4 alkoxy)carbonyl group.

(Dimethylamino)sulfonyl group, (diethylamino)sulfonyl group and (methylethylamino)sulfonyl group as the (di-C1–C4 alkylamino)sulfonyl group. In this case, each C1–C4 alkyl may be identical or different.

(N-Methyl-N-methoxyamino)sulfonyl group as the [N—(C1–C4 alkyl)-N—(C1–C4 alkoxy)amino]sulfonyl group.

Methylaminosulfonyl group as the (C1–C4 alkylamino)sulfonyl group.

Methylthio group as the C1–C4 alkylthio group.

Methylsulfinyl group as the C1–C4 alkylsulfinyl group.

Methylsulfonyl group as the C1–C4 alkylsulfonyl group.

Preferred examples of these groups include fluorine atom, chlorine atom, methyl group, trifluoromethyl group, methoxy group, trifluoromethoxy group, methoxycarbonyl group, (dimethylamino)-sulfonyl group, (N-methyl-N-methoxyamino)sulfonyl group, methylthio group, methylsulfinyl group and methylsulfonyl group.

A preferred range of n is 0 to 3, more preferably 0 to 2.

Since the preferred positions of X attached to the benzene ring are ortho positions to the N-substituted sulfamoyl group, it is preferred that the X attaches to one or both of them.

Regarding Ym:

Fluorine atom, chlorine atom and bromine atom as the halogen atom.

Methyl group, ethyl group and 1-methylethyl group as the C1–C4 alkyl group.

Fluoromethyl group, difluromethyl group and trifluoromethyl group as the C1–C4 haloalkyl group.

Methoxy group, ethoxy group and (1-methylethyl)oxy group as the C1–C4 alkoxy group.

Difluoromethoxy group, trifluoromethoxy group, (2-fluoroethyl)oxy group, (2,2-difluoroethyl)oxy group, (2,2,2-trifluoroethyl)oxy group, (1,1,2,2-tetrafuruoroethyl)oxy group, (2-chloro-1,1,2-trifluoroethyl)oxy group and (3,3,3-trifluroropropyl)oxy group as the C1–C4 haloalkoxy group.

Methylthio group as the C1–C4 alkylthio group.

Difluoromethylthio group as the C1–C4 haloalkylthio group.

Methylamino group as the C1–C4 alkylamino group.

Dimethylamino group and methyl ethyl amino group. In this case, each C1–C4 alkyl may be identical or different.

Methoxymethyl group as (C1–C4 alkoxy) C1–C4 alkyl group.

Methylthiomethyl group as the (C1–C4 alkylthio) C1–C4 alkyl group.

Preferred examples of these groups include fluorine atom, chlorine atom, bromine atom, methyl group, 1-methylethyl group, fluoromethyl group, trifluoromethyl group, methoxy group, ethoxy group, (1-methylethyl)oxy group, difluoromethoxy group, trifluoromethoxy group, methylthio group, difluoromethylthio group, methylamino group, dimethylamino group, etc.

A preferred range of m is 0 to 3, more preferably 0 to 2.

Since the preferred positions of Y attached to the pyridine ring are 4-, 5- and 6-positions when the nitrogen atom of the pyridine ring is 1-position and the N-substituted carbamoyl group is 2-position, Y is preferred to be attached to at least one of them.

Specific examples of the N-(phenylsulfonyl)picolinamide derivatives of the above described formula (I) according to the present invention include those as shown in Table 1.

The columns of substituent Xn and Ym in the Table 1 have the following common rule.

Xn: "position-substituent" is described as the case that the N-substituted sulfamoyl group on the benzene ring is I-position.

Accordingly, "2-$CF_3$" means that the $CF_3$ is attached to 2-position.

Similarly, "2-$COOCH_3$" means that the $COOCH_3$ is attached to 2-position, and "2-Cl" means that a chlorine atom is attached to 2-position. These cases correspond to n being 1.

"2,4-$Cl_2$" means that each chlorine atom is attached to 2- and 4-positions. Similarly, "2,6-$F_2$" means that each fluorine atom is attached to 2- and 6-positions. These cases correspond to n being 2.

Ym: "position-substituent" is described as the case that the N-substituted carbamoyl group on the pyridine ring is 2-position.

Accordingly, "4-OCH$_3$" means that the OCH$_3$ is attached to 4-position. This case corresponds to m being 1.

"4,6-Cl$_2$" means that each chlorine atom is attached to 4- and 6-positions. Similarly, "4,6-(OCH$_3$)$_2$" means that each OCH$_3$ is attached to 4- and 6-positions. These cases correspond to m being 2.

"4-OCH$_3$6-Cl" means that OCH$_3$ is attached to 4-position and the chlorine is attached to 6-position. This case corresponds to m being 2.

Xn of substituted benzenesulfonamide of the formula (III) shown in Table 3 and Ym of substituted picolinic acid of the formula (II) in Table 2 follows the same rule as described above. The same rule is used in this description, too.

TABLE 1

| Compound | Xn | Ym |
|---|---|---|
| I-1 | 2-CF$_3$ | 4-CF$_3$-6-Cl |
| I-2 | 2-CF$_3$ | 4-CH(CH$_3$)$_2$-6-Cl |
| I-3 | 2-CF$_3$ | 4-CH$_2$F-6-Cl |
| I-4 | 2-CF$_3$ | 4-CH$_2$OCH$_3$-6-Cl |
| I-5 | 2-CF$_3$ | 4-CH$_2$SCH$_3$-6-Cl |
| I-6 | 2-CF$_3$ | 4-CH$_3$-6-OCH$_3$ |
| I-7 | 2-CF$_3$ | 4-CHF$_2$-6-Cl |
| I-11 | 2-CF$_3$ | 4-Cl-6-CF$_3$ |
| I-12 | 2-CF$_3$ | 4-Cl-6-CH(CH$_3$)$_2$ |
| I-13 | 2-CF$_3$ | 4-Cl-6-CH$_2$F |
| I-14 | 2-CF$_3$ | 4-Cl-6-CH$_2$OCH$_3$ |
| I-15 | 2-CF$_3$ | 4-Cl-6-CH$_2$SCH$_3$ |
| I-16 | 2-CF$_3$ | 4-Cl-6-CHF$_2$ |
| I-17 | 2-CF$_3$ | 4,6-Cl$_2$ |
| I-21 | 2-CF$_3$ | 4-Cl-6-F |
| I-22 | 2-CF$_3$ | 4-Cl |
| I-23 | 2-CF$_3$ | 4-Cl-6-N(CH$_3$)$_2$ |
| I-24 | 2-CF$_3$ | 4-Cl-6-N(CH$_3$)C$_2$H$_5$ |
| I-25 | 2-CF$_3$ | 4-Cl-6-NH$_2$ |
| I-26 | 2-CF$_3$ | 4-Cl-6-NHCH$_3$ |
| I-27 | 2-CF$_3$ | 4-Cl-6-OCF$_2$CHF$_2$ |
| I-31 | 2-CF$_3$ | 4-Cl-6-OCF$_2$CHFCl |
| I-32 | 2-CF$_3$ | 4-Cl-6-OCF$_3$ |
| I-33 | 2-CF$_3$ | 4-Cl-6-OCH(CH$_3$)$_2$ |
| I-34 | 2-CF$_3$ | 4-Cl-6-OCH$_2$CH$_2$CF$_3$ |
| I-35 | 2-CF$_3$ | 4-Cl-6-OCH$_2$CF$_3$ |
| I-36 | 2-CF$_3$ | 4-Cl-6-OCH$_2$CH$_2$F |
| I-37 | 2-CF$_3$ | 4-Cl-6-OCH$_2$CHF$_2$ |
| I-41 | 2-CF$_3$ | 4-Cl-6-OCH$_3$ |
| I-42 | 2-CF$_3$ | 4-Cl-6-OCHF$_2$ |
| I-43 | 2-CF$_3$ | 4-Cl-6-OC$_2$H$_5$ |
| I-44 | 2-CF$_3$ | 4-Cl-6-SCH$_3$ |
| I-45 | 2-CF$_3$ | 4-Cl-6-SCHF$_2$ |
| I-46 | 2-CF$_3$ | 4-F-6-Cl |
| I-47 | 2-CF$_3$ | 4-F-6-OCH$_3$ |
| I-51 | 2-CF$_3$ | 6-Cl |
| I-52 | 2-CF$_3$ | (No substituted) |
| I-53 | 2-CF$_3$ | 6-OCH$_3$ |
| I-54 | 2-CF$_3$ | 5-OCH$_3$ |
| I-55 | 2-CF$_3$ | 4-N(CH$_3$)$_2$-6-Cl |
| I-56 | 2-CF$_3$ | 4-N(CH$_3$)C$_2$H$_5$-6-Cl |
| I-57 | 2-CF$_3$ | 4-NH$_2$-6-Cl |
| I-61 | 2-CF$_3$ | 4-NHCH$_3$-6-Cl |
| I-62 | 2-CF$_3$ | 4-OCF$_2$CHF$_2$-6-Cl |
| I-63 | 2-CF$_3$ | 4-OCF$_2$CHFCl-6-Cl |
| I-64 | 2-CF$_3$ | 4-OCF$_3$-6-Cl |
| I-65 | 2-CF$_3$ | 4,6-(OCF$_3$)$_2$ |
| I-66 | 2-CF$_3$ | 4-OCH(CH$_3$)$_2$-6-Cl |
| I-67 | 2-CF$_3$ | 4-OCH$_2$CH$_2$CF$_3$-6-Cl |
| I-71 | 2-CF$_3$ | 4-OCH$_2$CF$_3$-6-Cl |
| I-72 | 2-CF$_3$ | 4-OCH$_2$CH$_2$F-6-Cl |
| I-73 | 2-CF$_3$ | 4-OCH$_2$CHF$_2$-6-Cl |
| I-74 | 2-CF$_3$ | 4-OCH$_3$-6-CH$_3$ |
| I-75 | 2-CF$_3$ | 4-OCH$_3$-6-Cl |
| I-76 | 2-CF$_3$ | 4-OCH$_3$ |
| I-77 | 2-CF$_3$ | 4,6-(OCH$_3$)$_2$ |
| I-78 | 2-CF$_3$ | 5-OCH$_3$-6-Cl |
| I-79 | 2-CF$_3$ | 5,6-(OCH$_3$)$_2$ |
| I-80 | 2-CF$_3$ | 5-OCF$_3$-6-Cl |
| I-81 | 2-CF$_3$ | 4-OCHF$_2$-6-Cl |

TABLE 1-continued

| Compound | Xn | Ym |
|---|---|---|
| I-82 | 2-CF$_3$ | 4-OC$_2$H$_5$-6-Cl |
| I-83 | 2-CF$_3$ | 4-SCH$_3$-6-Cl |
| I-84 | 2-CF$_3$ | 4-SCHF$_2$-6-Cl |
| I-85 | 2-CF$_3$ | 5-OCH$_3$-6-Br |
| I-86 | 2-CF$_3$ | 5-OCH$_3$-6-F |
| I-87 | 2-CF$_3$ | 5-OCF$_3$-6-OCH$_3$ |
| I-88 | 2-CF$_3$ | 5-OCF$_3$-6-Br |
| I-89 | 2-CF$_3$ | 5-OCF$_3$-6-F |
| I-91 | 2-CH$_3$ | 4-CF$_3$-6-Cl |
| I-92 | 2-CH$_3$ | 4-CH(CH$_3$)$_2$-6-Cl |
| I-93 | 2-CH$_3$ | 4-CH$_2$F-6-Cl |
| I-94 | 2-CH$_3$ | 4-CH$_2$OCH$_3$-6-Cl |
| I-95 | 2-CH$_3$ | 4-CH$_2$SCH$_3$-6-Cl |
| I-96 | 2-CH$_3$ | 4-CH$_3$-6-OCH$_3$ |
| I-97 | 2-CH$_3$ | 4-CHF$_2$-6-Cl |
| I-101 | 2-CH$_3$ | 4-Cl-6-CF$_3$ |
| I-102 | 2-CH$_3$ | 4-Cl-6-CH(CH$_3$)$_2$ |
| I-103 | 2-CH$_3$ | 4-Cl-6-CH$_2$F |
| I-104 | 2-CH$_3$ | 4-Cl-6-CH$_2$OCH$_3$ |
| I-105 | 2-CH$_3$ | 4-Cl-6-CH$_2$SCH$_3$ |
| I-106 | 2-CH$_3$ | 4-Cl-6-CHF$_2$ |
| I-107 | 2-CH$_3$ | 4,6-Cl$_2$ |
| I-111 | 2-CH$_3$ | 4-Cl-6-F |
| I-112 | 2-CH$_3$ | 4-Cl |
| I-113 | 2-CH$_3$ | 4-Cl-6-N(CH$_3$)$_2$ |
| I-114 | 2-CH$_3$ | 4-Cl-6-N(CH$_3$)C$_2$H$_5$ |
| I-115 | 2-CH$_3$ | 4-Cl-6-NH$_2$ |
| I-116 | 2-CH$_3$ | 4-Cl-6-NHCH$_3$ |
| I-117 | 2-CH$_3$ | 4-Cl-6-OCF$_2$CHF$_2$ |
| I-121 | 2-CH$_3$ | 4-Cl-6-OCF$_2$CHFCl |
| I-122 | 2-CH$_3$ | 4-Cl-6-OCF$_3$ |
| I-123 | 2-CH$_3$ | 4-Cl-6-OCH(CH$_3$)$_2$ |
| I-124 | 2-CH$_3$ | 4-Cl-6-OCH$_2$CH$_2$CF$_3$ |
| I-125 | 2-CH$_3$ | 4-Cl-6-OCH$_2$CF$_3$ |
| I-126 | 2-CH$_3$ | 4-Cl-6-OCH$_2$CH$_2$F |
| I-127 | 2-CH$_3$ | 4-Cl-6-OCH$_2$CHF$_2$ |
| I-131 | 2-CH$_3$ | 4-Cl-6-OCH$_3$ |
| I-132 | 2-CH$_3$ | 4-Cl-6-OCHF$_2$ |
| I-133 | 2-CH$_3$ | 4-Cl-6-OC$_2$H$_5$ |
| I-134 | 2-CH$_3$ | 4-Cl-6-SCH$_3$ |
| I-135 | 2-CH$_3$ | 4-Cl-6-SCHF$_2$ |
| I-136 | 2-CH$_3$ | 4-F-6-Cl |
| I-137 | 2-CH$_3$ | 4-F-6-OCH$_3$ |
| I-141 | 2-CH$_3$ | 6-Cl |
| I-142 | 2-CH$_3$ | (No substituted) |
| I-143 | 2-CH$_3$ | 6-OCH$_3$ |
| I-144 | 2-CH$_3$ | 5-OCH$_3$ |
| I-145 | 2-CH$_3$ | 4-N(CH$_3$)$_2$-6-Cl |
| I-146 | 2-CH$_3$ | 4-N(CH$_3$)C$_2$H$_5$-6-Cl |
| I-147 | 2-CH$_3$ | 4-NH$_2$-6-Cl |
| I-151 | 2-CH$_3$ | 4-NHCH$_3$-6-Cl |
| I-152 | 2-CH$_3$ | 4-OCF$_2$CHF$_2$-6-Cl |
| I-153 | 2-CH$_3$ | 4-OCF$_2$CHFCl-6-Cl |
| I-154 | 2-CH$_3$ | 4-OCF$_3$-6-Cl |
| I-155 | 2-CH$_3$ | 4,6-(OCF$_3$)$_2$ |
| I-156 | 2-CH$_3$ | 4-OCH(CH$_3$)$_2$-6-Cl |
| I-157 | 2-CH$_3$ | 4-OCH$_2$CH$_2$CF$_3$-6-Cl |
| I-161 | 2-CH$_3$ | 4-OCH$_2$CF$_3$-6-Cl |
| I-162 | 2-CH$_3$ | 4-OCH$_2$CH$_2$F-6-Cl |
| I-163 | 2-CH$_3$ | 4-OCH$_2$CHF$_2$-6-Cl |
| I-164 | 2-CH$_3$ | 4-OCH$_3$-6-CH$_3$ |
| I-165 | 2-CH$_3$ | 4-OCH$_3$-6-Cl |
| I-166 | 2-CH$_3$ | 4-OCH$_3$ |
| I-167 | 2-CH$_3$ | 4,6-(OCH$_3$)$_2$ |
| I-168 | 2-CH$_3$ | 5-OCH$_3$-6-Cl |
| I-169 | 2-CH$_3$ | 5,6-(OCH$_3$)$_2$ |
| I-170 | 2-CH$_3$ | 5-OCF$_3$-6-Cl |
| I-171 | 2-CH$_3$ | 4-OCHF$_2$-6-Cl |
| I-172 | 2-CH$_3$ | 4-OC$_2$H$_5$-6-Cl |
| I-173 | 2-CH$_3$ | 4-SCH$_3$-6-Cl |
| I-174 | 2-CH$_3$ | 4-SCHF$_2$-6-Cl |
| I-175 | 2-CH$_3$ | 5-OCH$_3$-6-Br |
| I-176 | 2-CH$_3$ | 5-OCH$_3$-6-F |
| I-177 | 2-CH$_3$ | 5-OCF$_3$-6-OCH$_3$ |
| I-178 | 2-CH$_3$ | 5-OCF$_3$-6-Br |
| I-179 | 2-CH$_3$ | 5-OCF$_3$-6-F |
| I-181 | 2-COOCH$_3$ | 4-CF$_3$-6-Cl |

TABLE 1-continued

| Compound | Xn | Ym |
|---|---|---|
| I-182 | 2-COOCH$_3$ | 4-CH(CH$_3$)$_2$-6-Cl |
| I-183 | 2-COOCH$_3$ | 4-CH$_2$F-6-Cl |
| I-184 | 2-COOCH$_3$ | 4-CH$_2$OCH$_3$-6-Cl |
| I-185 | 2-COOCH$_3$ | 4-CH$_2$SCH$_3$-6-Cl |
| I-186 | 2-COOCH$_3$ | 4-CH$_3$-6-OCH$_3$ |
| I-187 | 2-COOCH$_3$ | 4-CHF$_2$-6-Cl |
| I-188 | 2-COOCH$_3$ | 4-CH$_3$-6-Cl |
| I-189 | 2-COOCH$_3$ | 3,6-Cl$_2$ |
| I-191 | 2-COOCH$_3$ | 4-Cl-6-CF$_3$ |
| I-192 | 2-COOCH$_3$ | 4-Cl-6-CH(CH$_3$)$_2$ |
| I-193 | 2-COOCH$_3$ | 4-Cl-6-CH$_2$F |
| I-194 | 2-COOCH$_3$ | 4-Cl-6-CH$_2$OCH$_3$ |
| I-195 | 2-COOCH$_3$ | 4-Cl-6-CH$_2$SCH$_3$ |
| I-196 | 2-COOCH$_3$ | 4-Cl-6-CHF$_2$ |
| I-197 | 2-COOCH$_3$ | 4,6-Cl$_2$ |
| I-201 | 2-COOCH$_3$ | 4-Cl-6-F |
| I-202 | 2-COOCH$_3$ | 4-Cl |
| I-203 | 2-COOCH$_3$ | 4-Cl-6-N(CH$_3$)$_2$ |
| I-204 | 2-COOCH$_3$ | 4-Cl-6-N(CH$_3$)C$_2$H$_5$ |
| I-205 | 2-COOCH$_3$ | 4-Cl-6-NH$_2$ |
| I-206 | 2-COOCH$_3$ | 4-Cl-6-NHCH$_3$ |
| I-207 | 2-COOCH$_3$ | 4-Cl-6-OCF$_2$CHF$_2$ |
| I-211 | 2-COOCH$_3$ | 4-Cl-6-OCF$_2$CHFCl |
| I-212 | 2-COOCH$_3$ | 4-Cl-6-OCF$_3$ |
| I-213 | 2-COOCH$_3$ | 4-Cl-6-OCH(CH$_3$)$_2$ |
| I-214 | 2-COOCH$_3$ | 4-Cl-6-OCH$_2$CH$_2$CF$_3$ |
| I-215 | 2-COOCH$_3$ | 4-Cl-6-OCH$_2$CF$_3$ |
| I-216 | 2-COOCH$_3$ | 4-Cl-6-OCH$_2$CH$_2$F |
| I-217 | 2-COOCH$_3$ | 4-Cl-6-OCH$_2$CHF$_2$ |
| I-221 | 2-COOCH$_3$ | 4-Cl-6-OCH$_3$ |
| I-222 | 2-COOCH$_3$ | 4-Cl-6-OCHF$_2$ |
| I-223 | 2-COOCH$_3$ | 4-Cl-6-OC$_2$H$_5$ |
| I-224 | 2-COOCH$_3$ | 4-Cl-6-SCH$_3$ |
| I-225 | 2-COOCH$_3$ | 4-Cl-6-SCHF$_2$ |
| I-226 | 2-COOCH$_3$ | 4-F-6-Cl |
| I-227 | 2-COOCH$_3$ | 4-F-6-OCH$_3$ |
| I-228 | 2-COOCH$_3$ | 5-OCH$_3$-6-CH$_3$ |
| I-231 | 2-COOCH$_3$ | 6-Cl |
| I-232 | 2-COOCH$_3$ | (No substituted) |
| I-233 | 2-COOCH$_3$ | 6-OCH$_3$ |
| I-234 | 2-COOCH$_3$ | 5-OCH$_3$ |
| I-235 | 2-COOCH$_3$ | 4-N(CH$_3$)$_2$-6-Cl |
| I-236 | 2-COOCH$_3$ | 4-N(CH$_3$)C$_2$H$_5$-6-Cl |
| I-237 | 2-COOCH$_3$ | 4-NH$_2$-6-Cl |
| I-241 | 2-COOCH$_3$ | 4-NHCH$_3$-6-Cl |
| I-242 | 2-COOCH$_3$ | 4-OCF$_2$CHF$_2$-6-Cl |
| I-243 | 2-COOCH$_3$ | 4-OCF$_2$CHFCl-6-Cl |
| I-244 | 2-COOCH$_3$ | 4-OCF$_3$-6-Cl |
| I-245 | 2-COOCH$_3$ | 4,6-(OCF$_3$)$_2$ |
| I-246 | 2-COOCH$_3$ | 4-OCH(CH$_3$)$_2$-6-Cl |
| I-247 | 2-COOCH$_3$ | 4-OCH$_2$CH$_2$CF$_3$-6-Cl |
| I-251 | 2-COOCH$_3$ | 4-OCH$_2$CF$_3$-6-Cl |
| I-252 | 2-COOCH$_3$ | 4-OCH$_2$CH$_2$F-6-Cl |
| I-253 | 2-COOCH$_3$ | 4-OCH$_2$CHF$_2$-6-Cl |
| I-254 | 2-COOCH$_3$ | 4-OCH$_3$-6-CH$_3$ |
| I-255 | 2-COOCH$_3$ | 4-OCH$_3$-6-Cl |
| I-256 | 2-COOCH$_3$ | 4-OCH$_3$ |
| I-257 | 2-COOCH$_3$ | 4,6-(OCH$_3$)$_2$ |
| I-258 | 2-COOCH$_3$ | 5-OCH$_3$-6-Cl |
| I-259 | 2-COOCH$_3$ | 5,6-(OCH$_3$)$_2$ |
| I-260 | 2-COOCH$_3$ | 5-OCF$_3$-6-Cl |
| I-261 | 2-COOCH$_3$ | 4-OCHF$_2$-6-Cl |
| I-262 | 2-COOCH$_3$ | 4-OC$_2$H$_5$-6-Cl |
| I-263 | 2-COOCH$_3$ | 4-SCH$_3$-6-Cl |
| I-264 | 2-COOCH$_3$ | 4-SCHF$_2$-6-Cl |
| I-265 | 2-COOCH$_3$ | 5-OCH$_3$-6-Br |
| I-266 | 2-COOCH$_3$ | 5-OCH$_3$-6-F |
| I-267 | 2-COOCH$_3$ | 5-OCF$_3$-6-OCH$_3$ |
| I-268 | 2-COOCH$_3$ | 5-OCF$_3$-6-Br |
| I-269 | 2-COOCH$_3$ | 5-OCF$_3$-6-F |
| I-271 | 2,3-Cl$_2$ | 4-CF$_3$-6-Cl |
| I-272 | 2,3-Cl$_2$ | 4-CH(CH$_3$)$_2$-6-Cl |
| I-273 | 2,3-Cl$_2$ | 4-CH$_2$F-6-Cl |
| I-274 | 2,3-Cl$_2$ | 4-CH$_2$OCH$_3$-6-Cl |
| I-275 | 2,3-Cl$_2$ | 4-CH$_2$SCH$_3$-6-Cl |
| I-276 | 2,3-Cl$_2$ | 4-CH$_3$-6-OCH$_3$ |
| I-277 | 2,3-Cl$_2$ | 4-CHF$_2$-6-Cl |
| I-281 | 2,3-Cl$_2$ | 4-Cl-6-CF$_3$ |
| I-282 | 2,3-Cl$_2$ | 4-Cl-6-CH(CH$_3$)$_2$ |
| I-283 | 2,3-Cl$_2$ | 4-Cl-6-CH$_2$F |
| I-284 | 2,3-Cl$_2$ | 4-Cl-6-CH$_2$OCH$_3$ |
| I-285 | 2,3-Cl$_2$ | 4-Cl-6-CH$_2$SCH$_3$ |
| I-286 | 2,3-Cl$_2$ | 4-Cl-6-CHF$_2$ |
| I-287 | 2,3-Cl$_2$ | 4,6-Cl$_2$ |
| I-291 | 2,3-Cl$_2$ | 4-Cl-6-F |
| I-292 | 2,3-Cl$_2$ | 4-Cl |
| I-293 | 2,3-Cl$_2$ | 4-Cl-6-N(CH$_3$)$_2$ |
| I-294 | 2,3-Cl$_2$ | 4-Cl-6-N(CH$_3$)C$_2$H$_5$ |
| I-295 | 2,3-Cl$_2$ | 4-Cl-6-NH$_2$ |
| I-296 | 2,3-Cl$_2$ | 4-Cl-6-NHCH$_3$ |
| I-297 | 2,3-Cl$_2$ | 4-Cl-6-OCF$_2$CHF$_2$ |
| I-301 | 2,3-Cl$_2$ | 4-Cl-6-OCF$_2$CHFCl |
| I-302 | 2,3-Cl$_2$ | 4-Cl-6-OCF$_3$ |
| I-303 | 2,3-Cl$_2$ | 4-Cl-6-OCH(CH$_3$)$_2$ |
| I-304 | 2,3-Cl$_2$ | 4-Cl-6-OCH$_2$CH$_2$CF$_3$ |
| I-305 | 2,3-Cl$_2$ | 4-Cl-6-OCH$_2$CF$_3$ |
| I-306 | 2,3-Cl$_2$ | 4-Cl-6-OCH$_2$CH$_2$F |
| I-307 | 2,3-Cl$_2$ | 4-Cl-6-OCH$_2$CHF$_2$ |
| I-311 | 2,3-Cl$_2$ | 4-Cl-6-OCH$_3$ |
| I-312 | 2,3-Cl$_2$ | 4-Cl-6-OCHF$_2$ |
| I-313 | 2,3-Cl$_2$ | 4-Cl-6-OC$_2$H$_5$ |
| I-314 | 2,3-Cl$_2$ | 4-Cl-6-SCH$_3$ |
| I-315 | 2,3-Cl$_2$ | 4-Cl-6-SCHF$_2$ |
| I-316 | 2,3-Cl$_2$ | 4-F-6-Cl |
| I-317 | 2,3-Cl$_2$ | 4-F-6-OCH$_3$ |
| I-321 | 2,3-Cl$_2$ | 6-Cl |
| I-322 | 2,3-Cl$_2$ | (No substituted) |
| I-323 | 2,3-Cl$_2$ | 6-OCH$_3$ |
| I-324 | 2,3-Cl$_2$ | 5-OCH$_3$ |
| I-325 | 2,3-Cl$_2$ | 4-N(CH$_3$)$_2$-6-Cl |
| I-326 | 2,3-Cl$_2$ | 4-N(CH$_3$)C$_2$H$_5$-6-Cl |
| I-327 | 2,3-Cl$_2$ | 4-NH$_2$-6-Cl |
| I-331 | 2,3-Cl$_2$ | 4-NHCH$_3$-6-Cl |
| I-332 | 2,3-Cl$_2$ | 4-OCF$_2$CHF$_2$-6-Cl |
| I-333 | 2,3-Cl$_2$ | 4-OCF$_2$CHFCl-6-Cl |
| I-334 | 2,3-Cl$_2$ | 4-OCF$_3$-6-Cl |
| I-335 | 2,3-Cl$_2$ | 4,6-(OCF$_3$)$_2$ |
| I-336 | 2,3-Cl$_2$ | 4-OCH(CH$_3$)$_2$-6-Cl |
| I-337 | 2,3-Cl$_2$ | 4-OCH$_2$CH$_2$CF$_3$-6-Cl |
| I-341 | 2,3-Cl$_2$ | 4-OCH$_2$CF$_3$-6-Cl |
| I-342 | 2,3-Cl$_2$ | 4-OCH$_2$CH$_2$F-6-Cl |
| I-343 | 2,3-Cl$_2$ | 4-OCH$_2$CHF$_2$-6-Cl |
| I-344 | 2,3-Cl$_2$ | 4-OCH$_3$-6-CH$_3$ |
| I-345 | 2,3-Cl$_2$ | 4-OCH$_3$-6-Cl |
| I-346 | 2,3-Cl$_2$ | 4-OCH$_3$ |
| I-347 | 2,3-Cl$_2$ | 4,6-(OCH$_3$)$_2$ |
| I-348 | 2,3-Cl$_2$ | 5-OCH$_3$-6-Cl |
| I-349 | 2,3-Cl$_2$ | 5,6-(OCH$_3$)$_2$ |
| I-350 | 2,3-Cl$_2$ | 5-OCF$_3$-6-Cl |
| I-351 | 2,3-Cl$_2$ | 4-OCHF$_2$-6-Cl |
| I-352 | 2,3-Cl$_2$ | 4-OC$_2$H$_5$-6-Cl |
| I-353 | 2,3-Cl$_2$ | 4-SCH$_3$-6-Cl |
| I-354 | 2,3-Cl$_2$ | 4-SCHF$_2$-6-Cl |
| I-355 | 2,3-Cl$_2$ | 5-OCH$_3$-6-Br |
| I-356 | 2,3-Cl$_2$ | 5-OCH$_3$-6-F |
| I-357 | 2,3-Cl$_2$ | 5-OCF$_3$-6-OCH$_3$ |
| I-358 | 2,3-Cl$_2$ | 5-OCF$_3$-6-Br |
| I-359 | 2,3-Cl$_2$ | 5-OCH$_3$-6-F |
| I-361 | 2,4-Cl$_2$ | 4-CF$_3$-6-Cl |
| I-362 | 2,4-Cl$_2$ | 4-CH(CH$_3$)$_2$-6-Cl |
| I-363 | 2,4-Cl$_2$ | 4-CH$_2$F-6-Cl |
| I-364 | 2,4-Cl$_2$ | 4-CH$_2$OCH$_3$-6-Cl |
| I-365 | 2,4-Cl$_2$ | 4-CH$_2$SCH$_3$-6-Cl |
| I-366 | 2,4-Cl$_2$ | 4-CH$_3$-6-OCH$_3$ |
| I-367 | 2,4-Cl$_2$ | 4-CHF$_2$-6-Cl |
| I-371 | 2,4-Cl$_2$ | 4-Cl-6-CF$_3$ |
| I-372 | 2,4-Cl$_2$ | 4-Cl-6-CH(CH$_3$)$_2$ |
| I-373 | 2,4-Cl$_2$ | 4-Cl-6-CH$_2$F |
| I-374 | 2,4-Cl$_2$ | 4-Cl-6-CH$_2$OCH$_3$ |
| I-375 | 2,4-Cl$_2$ | 4-Cl-6-CH$_2$SCH$_3$ |
| I-376 | 2,4-Cl$_2$ | 4-Cl-6-CHF$_2$ |
| I-377 | 2,4-Cl$_2$ | 4,6-Cl$_2$ |
| I-381 | 2,4-Cl$_2$ | 4-Cl-6-F |
| I-382 | 2,4-Cl$_2$ | 4-Cl |

TABLE 1-continued

| Compound | Xn | Ym |
|---|---|---|
| I-383 | 2,4-Cl$_2$ | 4-Cl-6-N(CH$_3$)$_2$ |
| I-384 | 2,4-Cl$_2$ | 4-Cl-6-N(CH$_3$)C$_2$H$_5$ |
| I-385 | 2,4-Cl$_2$ | 4-Cl-6-NH$_2$ |
| I-386 | 2,4-Cl$_2$ | 4-Cl-6-NHCH$_3$ |
| I-387 | 2,4-Cl$_2$ | 4-Cl-6-OCF$_2$CHF$_2$ |
| I-391 | 2,4-Cl$_2$ | 4-Cl-6-OCF$_2$CHFCl |
| I-392 | 2,4-Cl$_2$ | 4-Cl-6-OCF$_3$ |
| I-393 | 2,4-Cl$_2$ | 4-Cl-6-OCH(CH$_3$)$_2$ |
| I-394 | 2,4-Cl$_2$ | 4-Cl-6-OCH$_2$CH$_2$CF$_3$ |
| I-395 | 2,4-Cl$_2$ | 4-Cl-6-OCH$_2$CF$_3$ |
| I-396 | 2,4-Cl$_2$ | 4-Cl-6-OCH$_2$CH$_2$F |
| I-397 | 2,4-Cl$_2$ | 4-Cl-6-OCH$_2$CHF$_2$ |
| I-401 | 2,4-Cl$_2$ | 4-Cl-6-OCH$_3$ |
| I-402 | 2,4-Cl$_2$ | 4-Cl-6-OCHF$_2$ |
| I-403 | 2,4-Cl$_2$ | 4-Cl-6-OC$_2$H$_5$ |
| I-404 | 2,4-Cl$_2$ | 4-Cl-6-SCH$_3$ |
| I-405 | 2,4-Cl$_2$ | 4-Cl-6-SCHF$_2$ |
| I-406 | 2,4-Cl$_2$ | 4-F-6-Cl |
| I-407 | 2,4-Cl$_2$ | 4-F-6-OCH$_3$ |
| I-411 | 2,4-Cl$_2$ | 6-Cl |
| I-412 | 2,4-Cl$_2$ | (No substituted) |
| I-413 | 2,4-Cl$_2$ | 6-OCH$_3$ |
| I-414 | 2,4-Cl$_2$ | 5-OCH$_3$ |
| I-415 | 2,4-Cl$_2$ | 4-N(CH$_3$)$_2$-6-Cl |
| I-416 | 2,4-Cl$_2$ | 4-N(CH$_3$)C$_2$H$_5$-6-Cl |
| I-417 | 2,4-Cl$_2$ | 4-NH$_2$-6-Cl |
| I-421 | 2,4-Cl$_2$ | 4-NHCH$_3$-6-Cl |
| I-422 | 2,4-Cl$_2$ | 4-OCF$_2$CHF$_2$-6-Cl |
| I-423 | 2,4-Cl$_2$ | 4-OCF$_2$CHFCl-6-Cl |
| I-424 | 2,4-Cl$_2$ | 4-OCF$_3$-6-Cl |
| I-425 | 2,4-Cl$_2$ | 4,6-(OCF$_3$)$_2$ |
| I-426 | 2,4-Cl$_2$ | 4-OCH(CH$_3$)$_2$-6-Cl |
| I-427 | 2,4-Cl$_2$ | 4-OCH$_2$CH$_2$CF$_3$-6-Cl |
| I-431 | 2,4-Cl$_2$ | 4-OCH$_2$CF$_3$-6-Cl |
| I-432 | 2,4-Cl$_2$ | 4-OCH$_2$F-6-Cl |
| I-433 | 2,4-Cl$_2$ | 4-OCH$_2$CHF$_2$-6-Cl |
| I-434 | 2,4-Cl$_2$ | 4-OCH$_3$-6-CH$_3$ |
| I-435 | 2,4-Cl$_2$ | 4-OCH$_3$-6-Cl |
| I-436 | 2,4-Cl$_2$ | 4-OCH$_3$ |
| I-437 | 2,4-Cl$_2$ | 4,6-(OCH$_3$)$_2$ |
| I-438 | 2,4-Cl$_2$ | 5-OCH$_3$-6-Cl |
| I-439 | 2,4-Cl$_2$ | 5,6-(OCH$_3$)$_2$ |
| I-440 | 2,4-Cl$_2$ | 5-OCF$_3$-6-Cl |
| I-441 | 2,4-Cl$_2$ | 4-OCHF$_2$-6-Cl |
| I-442 | 2,4-Cl$_2$ | 4-OC$_2$H$_5$-6-Cl |
| I-443 | 2,4-Cl$_2$ | 4-SCH$_3$-6-Cl |
| I-444 | 2,4-Cl$_2$ | 4-SCHF$_2$-6-Cl |
| I-445 | 2,4-Cl$_2$ | 5-OCH$_3$-6-Br |
| I-446 | 2,4-Cl$_2$ | 5-OCH$_3$-6-F |
| I-447 | 2,4-Cl$_2$ | 5-OCF$_3$-6-OCH$_3$ |
| I-448 | 2,4-Cl$_2$ | 5-OCF$_3$-6-Br |
| I-449 | 2,4-Cl$_2$ | 5-OCF$_3$-6-F |
| I-451 | 2,5-Cl$_2$ | 4-CF$_3$-6-Cl |
| I-452 | 2,5-Cl$_2$ | 4-CH(CH$_3$)$_2$-6-Cl |
| I-453 | 2,5-Cl$_2$ | 4-CH$_2$F-6-Cl |
| I-454 | 2,5-Cl$_2$ | 4-CH$_2$OCH$_3$-6-Cl |
| I-455 | 2,5-Cl$_2$ | 4-CH$_2$SCH$_3$-6-Cl |
| I-456 | 2,5-Cl$_2$ | 4-CH$_3$-6-OCH$_3$ |
| I-457 | 2,5-Cl$_2$ | 4-CHF$_2$-6-Cl |
| I-461 | 2,5-Cl$_2$ | 4-Cl-6-CF$_3$ |
| I-462 | 2,5-Cl$_2$ | 4-Cl-6-CH(CH$_3$)$_2$ |
| I-463 | 2,5-Cl$_2$ | 4-Cl-6-CH$_2$F |
| I-464 | 2,5-Cl$_2$ | 4-Cl-6-CH$_2$OCH$_3$ |
| I-465 | 2,5-Cl$_2$ | 4-Cl-6-CH$_2$SCH$_3$ |
| I-466 | 2,5-Cl$_2$ | 4-Cl-6-CHF$_2$ |
| I-467 | 2,5-Cl$_2$ | 4,6-Cl$_2$ |
| I-471 | 2,5-Cl$_2$ | 4-Cl-6-F |
| I-472 | 2,5-Cl$_2$ | 4-Cl |
| I-473 | 2,5-Cl$_2$ | 4-Cl-6-N(CH$_3$)$_2$ |
| I-474 | 2,5-Cl$_2$ | 4-Cl-6-N(CH$_3$)C$_2$H$_5$ |
| I-475 | 2,5-Cl$_2$ | 4-Cl-6-NH$_2$ |
| I-476 | 2,5-Cl$_2$ | 4-Cl-6-NHCH$_3$ |
| I-477 | 2,5-Cl$_2$ | 4-Cl-6-OCF$_2$CHF$_2$ |
| I-481 | 2,5-Cl$_2$ | 4-Cl-6-OCF$_2$CHFCl |
| I-482 | 2,5-Cl$_2$ | 4-Cl-6-OCF$_3$ |
| I-483 | 2,5-Cl$_2$ | 4-Cl-6-OCH(CH$_3$)$_2$ |
| I-484 | 2,5-Cl$_2$ | 4-Cl-6-OCH$_2$CH$_2$CF$_3$ |
| I-485 | 2,5-Cl$_2$ | 4-Cl-6-OCH$_2$CF$_3$ |
| I-486 | 2,5-Cl$_2$ | 4-Cl-6-OCH$_2$CH$_2$F |
| I-487 | 2,5-Cl$_2$ | 4-Cl-6-OCH$_2$CHF$_2$ |
| I-491 | 2,5-Cl$_2$ | 4-Cl-6-OCH$_3$ |
| I-492 | 2,5-Cl$_2$ | 4-cl-6-OCHF$_2$ |
| I-493 | 2,5-Cl$_2$ | 4-Cl-6-OC$_2$H$_5$ |
| I-494 | 2,5-Cl$_2$ | 4-Cl-6-SCH$_3$ |
| I-495 | 2,5-Cl$_2$ | 4-Cl-6-SCHF$_2$ |
| I-496 | 2,5-Cl$_2$ | 4-F-6-Cl |
| I-497 | 2,5-Cl$_2$ | 4-F-6-OCH$_3$ |
| I-501 | 2,5-Cl$_2$ | 6-Cl |
| I-502 | 2,5-Cl$_2$ | (No substituted) |
| I-503 | 2,5-Cl$_2$ | 6-OCH$_3$ |
| I-504 | 2,5-Cl$_2$ | 5-OCH$_3$ |
| I-505 | 2,5-Cl$_2$ | 4-N(CH$_3$)$_2$-6-Cl |
| I-506 | 2,5-Cl$_2$ | 4-N(CH$_3$)C$_2$H$_5$-6-Cl |
| I-507 | 2,5-Cl$_2$ | 4-NH$_2$-6-Cl |
| I-511 | 2,5-Cl$_2$ | 4-NHCH$_3$-6-Cl |
| I-512 | 2,5-Cl$_2$ | 4-OCF$_2$CHF$_2$-6-Cl |
| I-513 | 2,5-Cl$_2$ | 4-OCF$_2$CHFCl-6-Cl |
| I-514 | 2,5-Cl$_2$ | 4-OCF$_3$-6-Cl |
| I-515 | 2,5-Cl$_2$ | 4,6-(OCF$_3$)$_2$ |
| I-516 | 2,5-Cl$_2$ | 4-OCH(CH$_3$)$_2$-6-Cl |
| I-517 | 2,5-Cl$_2$ | 4-OCHQCH$_2$CF$_3$-6-Cl |
| I-521 | 2,5-Cl$_2$ | 4-OCH$_2$CF$_3$-6-Cl |
| I-522 | 2,5-Cl$_2$ | 4-OCH$_2$CH$_2$F-6-Cl |
| I-523 | 2,5-Cl$_2$ | 4-OCH$_2$CHF$_2$-6-Cl |
| I-524 | 2,5-Cl$_2$ | 4-OCH$_3$-6-CH$_3$ |
| I-525 | 2,5-Cl$_2$ | 4-OCH$_3$-6-Cl |
| I-526 | 2,5-Cl$_2$ | 4-OCH$_3$ |
| I-527 | 2,5-Cl$_2$ | 4,6-(OCH$_3$)$_2$ |
| I-528 | 2,5-Cl$_2$ | 5-OCH$_3$-6-Cl |
| I-529 | 2,5-Cl$_2$ | 5,6-(OCH$_3$)$_2$ |
| I-530 | 2,5-Cl$_2$ | 5-OCF$_3$-6-Cl |
| I-531 | 2,5-Cl$_2$ | 4-OCHF$_2$-6-Cl |
| I-532 | 2,5-Cl$_2$ | 4-OC$_2$H$_5$-6-Cl |
| I-533 | 2,5-Cl$_2$ | 4-SCH$_3$-6-Cl |
| I-534 | 2,5-Cl$_2$ | 4-SCHF$_2$-6-Cl |
| I-535 | 2,5-Cl$_2$ | 5-OCH$_3$-6-Br |
| I-536 | 2,5-Cl$_2$ | 5-OCH$_3$-6-F |
| I-537 | 2,5-Cl$_2$ | 5-OCF$_3$-6-OCH$_3$ |
| I-538 | 2,5-Cl$_2$ | 5-OCF$_3$-6-Br |
| I-539 | 2,5-Cl$_2$ | 5-OCH$_3$-6-F |
| I-541 | 2,6-Cl$_2$ | 4-CF$_3$-6-Cl |
| I-542 | 2,6-Cl$_2$ | 4-CH(CH$_3$)$_2$-6-Cl |
| I-543 | 2,6-Cl$_2$ | 4-CH$_2$F-6-Cl |
| I-544 | 2,6-Cl$_2$ | 4-CH$_2$OCH$_3$-6-Cl |
| I-545 | 2,6-Cl$_2$ | 4-CH$_2$SCH$_3$-6-Cl |
| I-546 | 2,6-Cl$_2$ | 4-CH$_3$-6-OCH$_3$ |
| I-547 | 2,6-Cl$_2$ | 4-CHF$_2$-6-Cl |
| I-548 | 2,6-Cl$_2$ | 4-CH$_3$-6-Cl |
| I-551 | 2,6-Cl$_2$ | 4-Cl-6-CF$_3$ |
| I-552 | 2,6-Cl$_2$ | 4-Cl-6-CH(CH$_3$)$_2$ |
| I-553 | 2,6-Cl$_2$ | 4-Cl-6-CH$_2$F |
| I-554 | 2,6-Cl$_2$ | 4-Cl-6-CH$_2$OCH$_3$ |
| I-555 | 2,6-Cl$_2$ | 4-Cl-6-CH$_2$SCH$_3$ |
| I-556 | 2,6-Cl$_2$ | 4-Cl-6-CHF$_2$ |
| I-557 | 2,6-Cl$_2$ | 4,6-Cl$_2$ |
| I-561 | 2,6-Cl$_2$ | 4-Cl-6-F |
| I-562 | 2,6-Cl$_2$ | 4-Cl |
| I-563 | 2,6-Cl$_2$ | 4-Cl-6-N(CH$_3$)$_2$ |
| I-564 | 2,6-Cl$_2$ | 4-Cl-6-N(CH$_3$)C$_2$H$_5$ |
| I-565 | 2,6-Cl$_2$ | 4-Cl-6-NH$_2$ |
| I-566 | 2,6-Cl$_2$ | 4-Cl-6-NHCH$_3$ |
| I-567 | 2,6-Cl$_2$ | 4-Cl-6-OCF$_2$CHF$_2$ |
| I-568 | 2,6-Cl$_2$ | 3,6-Cl$_2$ |
| I-571 | 2,6-Cl$_2$ | 4-Cl-6-OCF$_2$CHFCl |
| I-572 | 2,6-Cl$_2$ | 4-Cl-6-OCF$_3$ |
| I-573 | 2,6-Cl$_2$ | 4-Cl-6-OCH(CH$_3$)$_2$ |
| I-574 | 2,6-Cl$_2$ | 4-Cl-6-OCH$_2$CH$_2$CF$_3$ |
| I-575 | 2,6-Cl$_2$ | 4-Cl-6-OCH$_2$CF$_3$ |
| I-576 | 2,6-Cl$_2$ | 4-Cl-6-OCH$_2$CH$_2$F |
| I-577 | 2,6-Cl$_2$ | 4-Cl-6-OCH$_2$CHF$_2$ |
| I-581 | 2,6-Cl$_2$ | 4-Cl-6-OCH$_3$ |
| I-582 | 2,6-Cl$_2$ | 4-Cl-6-OCHF$_2$ |
| I-583 | 2,6-Cl$_2$ | 4-Cl-6-OC$_2$H$_5$ |
| I-584 | 2,6-Cl$_2$ | 4-Cl-6-SCH$_3$ |

TABLE 1-continued

| Compound | Xn | Ym |
|---|---|---|
| I-585 | 2,6-Cl$_2$ | 4-Cl-6-SCHF$_2$ |
| I-586 | 2,6-Cl$_2$ | 4-F-6-Cl |
| I-587 | 2,6-Cl$_2$ | 4-F-6-OCH$_3$ |
| I-591 | 2,6-Cl$_2$ | 6-Cl |
| I-592 | 2,6-Cl$_2$ | (No substituted) |
| I-593 | 2,6-Cl$_2$ | 6-OCH$_3$ |
| I-594 | 2,6-Cl$_2$ | 5-OCH$_3$ |
| I-595 | 2,6-Cl$_2$ | 4-N(CH$_3$)$_2$-6-Cl |
| I-596 | 2,6-Cl$_2$ | 4-N(CH$_3$)C$_2$H$_5$-6-Cl |
| I-597 | 2,6-Cl$_2$ | 4-NH$_2$-6-Cl |
| I-601 | 2,6-Cl$_2$ | 4-NHCH$_3$-6-Cl |
| I-602 | 2,6-Cl$_2$ | 4-OCF$_2$CHF$_2$-6-Cl |
| I-603 | 2,6-Cl$_2$ | 4-OCF$_2$CHFCl-6-Cl |
| I-604 | 2,6-Cl$_2$ | 4-OCF$_3$-6-Cl |
| I-605 | 2,6-Cl$_2$ | 4,6-(OCF$_3$)$_2$ |
| I-606 | 2,6-Cl$_2$ | 4-OCH(CH$_3$)$_2$-6-Cl |
| I-607 | 2,6-Cl$_2$ | 4-OCH$_2$CH$_2$CF$_3$-6-Cl |
| I-611 | 2,6-Cl$_2$ | 4-OCH$_2$CF$_3$-6-CL |
| I-612 | 2,6-Cl$_2$ | 4-OCH$_2$CH$_2$F-6-Cl |
| I-613 | 2,6-Cl$_2$ | 4-OCH$_2$CHF$_2$-6-Cl |
| I-614 | 2,6-Cl$_2$ | 4-OCH$_3$-6-CH$_3$ |
| I-615 | 2,6-Cl$_2$ | 4-OCH$_3$-6-Cl |
| I-616 | 2,6-Cl$_2$ | 4-OCH$_3$ |
| I-617 | 2,6-Cl$_2$ | 4,6-(OCH$_3$)$_2$ |
| I-618 | 2,6-Cl$_2$ | 5-OCH$_3$-6-Cl |
| I-619 | 2,6-Cl$_2$ | 5,6-(OCH$_3$)$_2$ |
| I-620 | 2,6-Cl$_2$ | 5-OCF$_3$-6-Cl |
| I-621 | 2,6-Cl$_2$ | 4-OCHF$_2$-6-Cl |
| I-622 | 2,6-Cl$_2$ | 4-OC$_2$H$_5$-6-Cl |
| I-623 | 2,6-Cl$_2$ | 4-SCH$_3$-6-Cl |
| I-624 | 2,6-Cl$_2$ | 4-SCHF$_2$-6-Cl |
| I-625 | 2,6-Cl$_2$ | 5-OCH$_3$-6-Br |
| I-626 | 2,6-Cl$_2$ | 5-OCH$_3$-6-F |
| I-627 | 2,6-Cl$_2$ | 5-OCF$_3$-6-OCH$_3$ |
| I-628 | 2,6-Cl$_2$ | 5-OCF$_3$-6-Br |
| I-629 | 2,6-Cl$_2$ | 5-OCF$_3$-6-F |
| I-631 | 2-Cl | 4-CF$_3$-6-Cl |
| I-632 | 2-Cl | 4-CH(CH$_3$)$_2$-6-Cl |
| I-633 | 2-Cl | 4-CH$_2$F-6-Cl |
| I-634 | 2-Cl | 4-CH$_2$OCH$_3$-6-Cl |
| I-635 | 2-Cl | 4-CH$_2$SCH$_3$-6-Cl |
| I-636 | 2-Cl | 4-CH$_3$-6-OCH$_3$ |
| I-637 | 2-Cl | 4-CHF$_2$-6-Cl |
| I-641 | 2-Cl | 4-Cl-6-CF$_3$ |
| I-642 | 2-Cl | 4-Cl-6-CH(CH$_3$)$_2$ |
| I-643 | 2-Cl | 4-Cl-6-CH$_2$F |
| I-644 | 2-Cl | 4-Cl-6-CH$_2$OCH$_3$ |
| I-645 | 2-Cl | 4-Cl-6-CH$_2$SCH$_3$ |
| I-646 | 2-Cl | 4-Cl-6-CHF$_2$ |
| I-647 | 2-Cl | 4 6-Cl$_2$ |
| I-651 | 2-Cl | 4-Cl-6-F |
| I-652 | 2-Cl | 4-Cl |
| I-653 | 2-Cl | 4-Cl-6-N(CH$_3$)$_2$ |
| I-654 | 2-Cl | 4-Cl-6-N(CH$_3$)C$_2$H$_5$ |
| I-655 | 2-Cl | 4-Cl-6-NH$_2$ |
| I-656 | 2-Cl | 4-Cl-6-NHCH$_3$ |
| I-657 | 2-Cl | 4-Cl-6-OCF$_2$CHF$_2$ |
| I-661 | 2-Cl | 4-Cl-6-OCF$_2$CHFCl |
| I-662 | 2-Cl | 4-Cl-6-OCF$_3$ |
| I-663 | 2-Cl | 4-Cl-6-OCH(CH$_3$)$_2$ |
| I-664 | 2-Cl | 4-Cl-6-OCH$_2$CH$_2$CF$_3$ |
| I-665 | 2-Cl | 4-Cl-6-OCH$_2$CF$_3$ |
| I-666 | 2-Cl | 4-Cl-6-OCH$_2$CH$_2$F |
| I-667 | 2-Cl | 4-Cl-6-OCH$_2$CHF$_2$ |
| I-671 | 2-Cl | 4-Cl-6-OCH$_3$ |
| I-672 | 2-Cl | 4-Cl-6-OCHF$_2$ |
| I-673 | 2-Cl | 4-Cl-6-OC$_2$H$_5$ |
| I-674 | 2-Cl | 4-Cl-6-SCH$_3$ |
| I-675 | 2-Cl | 4-Cl-6-SCHF$_2$ |
| I-676 | 2-Cl | 4-F-6-Cl |
| I-677 | 2-Cl | 4-F-6-OCH$_3$ |
| I-681 | 2-Cl | 6-Cl |
| I-682 | 2-Cl | (No substituted) |
| I-683 | 2-Cl | 6-OCH$_3$ |
| I-684 | 2-Cl | 5-OCH$_3$ |
| I-685 | 2-Cl | 4-N(CH$_3$)$_2$-6-Cl |
| I-686 | 2-Cl | 4-N(CH$_3$)C$_2$H$_5$-6-Cl |
| I-687 | 2-Cl | 4-NH$_2$-6-Cl |
| I-691 | 2-Cl | 4-NHCH$_3$-6-Cl |
| I-692 | 2-Cl | 4-OCF$_2$CHF$_2$-6-Cl |
| I-693 | 2-Cl | 4-OCF$_2$CHFCl-6-Cl |
| I-694 | 2-Cl | 4-OCF$_3$-6-Cl |
| I-695 | 2-Cl | 4,6-(OCF$_3$)$_2$ |
| I-696 | 2-Cl | 4-OCH(CH$_3$)$_2$-6-Cl |
| I-697 | 2-Cl | 4-OCH$_2$CH$_2$CF$_3$-6-Cl |
| I-701 | 2-Cl | 4-OCH$_2$CF$_3$-6-Cl |
| I-702 | 2-Cl | 4-OCH$_2$CH$_2$F-6-Cl |
| I-703 | 2-Cl | 4-OCH$_2$CHF$_2$-6-Cl |
| I-704 | 2 Cl | 4-OCH$_3$-6-CH$_3$ |
| I-705 | 2-Cl | 4-OCH$_3$-6-Cl |
| I-706 | 2-Cl | 4-OCH$_3$ |
| I-707 | 2-Cl | 4,6-(OCH$_3$)$_2$ |
| I-708 | 2-Cl | 5-OCH$_3$-6-Cl |
| I-709 | 2-Cl | 5,6-(OCH$_3$)$_2$ |
| I-710 | 2-Cl | 5-OCF$_3$-6-Cl |
| I-711 | 2-Cl | 4-OCHF$_2$-6-Cl |
| I-712 | 2-Cl | 4-OC$_2$H$_5$-6-Cl |
| I-713 | 2-Cl | 4-SCH$_3$-6-Cl |
| I-714 | 2-Cl | 4-SCHF$_2$-6-Cl |
| I-715 | 2-Cl | 5-OCH$_3$-6-Br |
| I-716 | 2-Cl | 5-OCH$_3$-6-F |
| I-717 | 2-Cl | 5-OCF$_3$-6-OCH$_3$ |
| I-718 | 2-Cl | 5-OCF$_3$-6-Br |
| I-719 | 2-Cl | 5-OCF$_3$-6-F |
| I-721 | 2-OCF$_3$ | 4-CF$_3$-6-Cl |
| I-722 | 2-OCF$_3$ | 4-CH(CH$_3$)$_2$-6-Cl |
| I-723 | 2-OCF$_3$ | 4-CH$_2$F-6-Cl |
| I-724 | 2-OCF$_3$ | 4-CH$_2$OCH$_3$-6-Cl |
| I-725 | 2-OCF$_3$ | 4-CH$_2$SCH$_3$-6-Cl |
| I-726 | 2-OCF$_3$ | 4-CH$_3$-6-OCH$_3$ |
| I-727 | 2-OCF$_3$ | 4-CHF$_2$-6-Cl |
| I-728 | 2-OCF$_3$ | 4-CH$_3$-6-Cl |
| I-731 | 2-OCF$_3$ | 4-Cl-6-CF$_3$ |
| I-732 | 2-OCF$_3$ | 4-Cl-6-CH(CH$_3$)$_2$ |
| I-733 | 2-OCF$_3$ | 4-Cl-6-CH$_2$F |
| I-734 | 2-OCF$_3$ | 4-Cl-6-CH$_2$OCH$_3$ |
| I-735 | 2-OCF$_3$ | 4-Cl-6-CH$_2$SCH$_3$ |
| I-736 | 2-OCF$_3$ | 4-Cl-6-CHF$_2$ |
| I-737 | 2-OCF$_3$ | 4,6-Cl$_2$ |
| I-738 | 2-OCF$_3$ | 3,6-Cl$_2$ |
| I-741 | 2-OCF$_3$ | 4-Cl-6-F |
| I-742 | 2-OCF$_3$ | 4-Cl |
| I-743 | 2-OCF$_3$ | 4-Cl-6-N(CH$_3$)$_2$ |
| I-744 | 2-OCF$_3$ | 4-Cl-6-N(CH$_3$)C$_2$H$_5$ |
| I-745 | 2-OCF$_3$ | 4-Cl-6-NH$_2$ |
| I-746 | 2-OCF$_3$ | 4-Cl-6-NHCH$_3$ |
| I-747 | 2-OCF$_3$ | 4-Cl-6-OCF$_2$CHF$_2$ |
| I-751 | 2-OCF$_3$ | 4-Cl-6-OCF$_2$CHFCl |
| I-752 | 2-OCF$_3$ | 4-Cl-6-OCF$_3$ |
| I-753 | 2-OCF$_3$ | 4-Cl-6-OCH(CH$_3$)$_2$ |
| I-754 | 2-OCF$_3$ | 4-Cl-6-OCH$_2$CH$_2$CF$_3$ |
| I-755 | 2-OCF$_3$ | 4-Cl-6-OCH$_2$CF$_3$ |
| I-756 | 2-OCF$_3$ | 4-Cl-6-OCH$_2$CH$_2$F |
| I-757 | 2-OCF$_3$ | 4-Cl-6-OCH$_2$CHF$_2$ |
| I-761 | 2-OCF$_3$ | 4-Cl-6-OCH$_3$ |
| I-762 | 2-OCF$_3$ | 4-Cl-6-OCHF$_2$ |
| I-763 | 2-OCF$_3$ | 4-Cl-6-OC$_2$H$_5$ |
| I-764 | 2-OCF$_3$ | 4-Cl-6-SCH$_3$ |
| I-765 | 2-OCF$_3$ | 4-Cl-6-SCHF$_2$ |
| I-766 | 2-OCF$_3$ | 4-F-6-Cl |
| I-767 | 2-OCF$_3$ | 4-F-6-OCH$_3$ |
| I-771 | 2-OCF$_3$ | 6-Cl |
| I-772 | 2-OCF$_3$ | (No substituted) |
| I-773 | 2-OCF$_3$ | 6-OCH$_3$ |
| I-774 | 2-OCF$_3$ | 5-OCH$_3$ |
| I-775 | 2-OCF$_3$ | 4-N(CH$_3$)$_2$-6-Cl |
| I-776 | 2-OCF$_3$ | 4-N(CH$_3$)C$_2$H$_5$-6-Cl |
| I-777 | 2-OCF$_3$ | 4-NH$_2$-6-Cl |
| I-778 | 2-OCF$_3$ | 5-OCH$_3$-6-NO$_2$ |
| I-778 | 2-OCF$_3$ | 5-OCH$_3$-6-NO$_2$ |
| I-781 | 2-OCF$_3$ | 4-NHCH$_3$-6-Cl |
| I-782 | 2-OCF$_3$ | 4-OCF$_2$CHF$_2$-6-Cl |
| I-783 | 2-OCF$_3$ | 4-OCF$_2$CHFCl-6-Cl |
| I-784 | 2-OCF$_3$ | 4-OCF$_3$-6-Cl |

TABLE 1-continued

| Compound | Xn | Ym |
|---|---|---|
| I-785 | 2-OCF$_3$ | 4,6-(OCF$_3$)$_2$ |
| I-786 | 2-OCF$_3$ | 4-OCH(CH$_3$)$_2$-6-Cl |
| I-787 | 2-OCF$_3$ | 4-OCH$_2$CH$_2$CF$_3$-6-Cl |
| I-791 | 2-OCF$_3$ | 4-OCH$_2$CF$_3$-6-Cl |
| I-792 | 2-OCF$_3$ | 4-OCH$_2$CH$_2$F-6-Cl |
| I-793 | 2-OCF$_3$ | 4-OCH$_2$CHF$_2$-6-Cl |
| I-794 | 2-OCF$_3$ | 4-OCH$_3$-6-CH$_3$ |
| I-795 | 2-OCF$_3$ | 4-OCH$_3$-6-Cl |
| I-796 | 2-OCF$_3$ | 4-OCH$_3$ |
| I-797 | 2-OCF$_3$ | 4,6-(OCH$_3$)$_2$ |
| I-798 | 2-OCF$_3$ | 5-OCH$_3$-6-Cl |
| I-799 | 2-OCF$_3$ | 5,6-(OCH$_3$)$_2$ |
| I-800 | 2-OCF$_3$ | 5-OCF$_3$-6-Cl |
| I-801 | 2-OCF$_3$ | 4-OCHF$_2$-6-Cl |
| I-802 | 2-OCF$_3$ | 4-OC$_2$H$_5$-6-Cl |
| I-803 | 2-OCF$_3$ | 4-SCH$_3$-6-Cl |
| I-804 | 2-OCF$_3$ | 4-SCHF$_2$-6-Cl |
| I-805 | 2-OCF$_3$ | 5-OCH$_3$-6-Br |
| I-806 | 2-OCF$_3$ | 5-OCH$_3$-6-F |
| I-807 | 2-OCF$_3$ | 5-OCF$_3$-6-OCH$_3$ |
| I-808 | 2-OCF$_3$ | 5-OCF$_3$-6-Br |
| I-809 | 2-OCF$_3$ | 5-OCF$_3$-6-F |
| I-811 | 2-SO$_2$N(CH$_3$)$_2$ | 4-CF$_3$-6-Cl |
| I-812 | 2-SO$_2$N(CH$_3$)$_2$ | 4-CH(CH$_3$)$_2$-6-Cl |
| I-813 | 2-SO$_2$N(CH$_3$)$_2$ | 4-CH$_2$F-6-Cl |
| I-814 | 2-SO$_2$N(CH$_3$)$_2$ | 4-CH$_2$OCH$_3$-6-Cl |
| I-815 | 2-SO$_2$N(CH$_3$)$_2$ | 4-CH$_2$SCH$_3$-6-Cl |
| I-816 | 2-SO$_2$N(CH$_3$)$_2$ | 4-CH$_3$-6-OCH$_3$ |
| I-817 | 2-SO$_2$N(CH$_3$)$_2$ | 4-CHF$_2$-6-Cl |
| I-818 | 2-SO$_2$CH$_3$ | 4-OCH$_3$-6-Cl |
| I-819 | 2-SO$_2$CH$_3$ | 5-OCH$_3$-6-Br |
| I-820 | 2-SO$_2$N(CH$_3$)$_2$ | 4-CH$_3$-6-Cl |
| I-821 | 2-SO$_2$N(CH$_3$)$_2$ | 4-Cl-6-CF$_3$ |
| I-822 | 2-SO$_2$N(CH$_3$)$_2$ | 4-Cl-6-CH(CH$_3$)$_2$ |
| I-823 | 2-SO$_2$N(CH$_3$)$_2$ | 4-Cl-6-CH$_2$F |
| I-824 | 2-SO$_2$N(CH$_3$)$_2$ | 4-Cl-6-CH$_2$OCH$_3$ |
| I-825 | 2-SO$_2$N(CH$_3$)$_2$ | 4-Cl-6-CH$_2$SCH$_3$ |
| I-826 | 2-SO$_2$N(CH$_3$)$_2$ | 4-Cl-6-CHF$_2$ |
| I-827 | 2-SO$_2$N(CH$_3$)$_2$ | 4,6-Cl$_2$ |
| I-828 | 2-SO$_2$N(CH$_3$)$_2$ | 3,6-Cl$_2$ |
| I-830 | 2-SO$_2$N(OCH$_3$)CH$_3$ | 5-OCH$_3$-6-Br |
| I-831 | 2-SO$_2$N(CH$_3$)$_2$ | 4-Cl-6-F |
| I-832 | 2-SO$_2$N(CH$_3$)$_2$ | 4-Cl |
| I-833 | 2-SO$_2$N(CH$_3$)$_2$ | 4-Cl-6-N(CH$_3$)$_2$ |
| I-834 | 2-SO$_2$N(CH$_3$)$_2$ | 4-Cl-6-N(CH$_3$)C$_2$H$_5$ |
| I-835 | 2-SO$_2$N(CH$_3$)$_2$ | 4-Cl-6-NH$_2$ |
| I-836 | 2-SO$_2$N(CH$_3$)$_2$ | 4-Cl-6-NHCH$_3$ |
| I-837 | 2-SO$_2$N(CH$_3$)$_2$ | 4-Cl-6-OCF$_2$CHF$_2$ |
| I-838 | 2-SO$_2$N(OCH$_3$)CH$_3$ | 4-OCH$_3$-6-Cl |
| I-841 | 2-SO$_2$N(CH$_3$)$_2$ | 4-Cl-6-OCF$_2$CHFCl |
| I-842 | 2-SO$_2$N(CH$_3$)$_2$ | 4-Cl-6-OCF$_3$ |
| I-843 | 2-SO$_2$N(CH$_3$)$_2$ | 4-Cl-6-OCH(CH$_3$)$_2$ |
| I-844 | 2-SO$_2$N(CH$_3$)$_2$ | 4-Cl-6-OCH$_2$CH$_2$CF$_3$ |
| I-845 | 2-SO$_2$N(CH$_3$)$_2$ | 4-Cl-6-OCH$_2$CF$_3$ |
| I-846 | 2-SO$_2$N(CH$_3$)$_2$ | 4-Cl-6-OCH$_2$CH$_2$F |
| I-847 | 2-SO$_2$N(CH$_3$)$_2$ | 4-Cl-6-OCH$_2$CHF$_2$ |
| I-851 | 2-SO$_2$N(CH$_3$)$_2$ | 4-Cl-6-OCH$_3$ |
| I-852 | 2-SO$_2$N(CH$_3$)$_2$ | 4-Cl-6-OCHF$_2$ |
| I-853 | 2-SO$_2$N(CH$_3$)$_2$ | 4-Cl-6-OC$_2$H$_5$ |
| I-854 | 2-SO$_2$N(CH$_3$)$_2$ | 4-Cl-6-SCH$_3$ |
| I-855 | 2-SO$_2$N(CH$_3$)$_2$ | 4-Cl-6-SCHF$_2$ |
| I-856 | 2-SO$_2$N(CH$_3$)$_2$ | 4-F-6-Cl |
| I-857 | 2-SO$_2$N(CH$_3$)$_2$ | 4-F-6-OCH$_3$ |
| I-858 | 2-SO$_2$N(CH$_3$)$_2$ | 5-OCH$_3$-6-NO$_2$ |
| I-859 | 2-SO$_2$N(CH$_3$)$_2$ | 5-OCH$_3$-6-CH$_3$ |
| I-861 | 2-SO$_2$N(CH$_3$)$_2$ | 6-Cl |
| I-862 | 2-SO$_2$N(CH$_3$)$_2$ | (No substituted) |
| I-863 | 2-SO$_2$N(CH$_3$)$_2$ | 6-OCH$_3$ |
| I-864 | 2-SO$_2$N(CH$_3$)$_2$ | 5-OCH$_3$ |
| I-865 | 2-SO$_2$N(CH$_3$)$_2$ | 4-N(CH$_3$)$_2$-6-Cl |
| I-866 | 2-SO$_2$N(CH$_3$)$_2$ | 4-N(CH$_3$)C$_2$H$_5$-6-Cl |
| I-867 | 2-SO$_2$N(CH$_3$)$_2$ | 4-NH$_2$-6-Cl |
| I-868 | 2-SO$_2$N(CH$_3$)$_2$ | 5-NO$_2$-6-CH$_3$ |
| I-871 | 2-SO$_2$N(CH$_3$)$_2$ | 4-NHCH$_3$-6-Cl |
| I-872 | 2-SO$_2$N(CH$_3$)$_2$ | 4-OCF$_2$CHF$_2$-6-Cl |
| I-873 | 2-SO$_2$N(CH$_3$)$_2$ | 4-OCF$_2$CHFCl-6-Cl |
| I-874 | 2-SO$_2$N(CH$_3$)$_2$ | 4-OCF$_3$-6-Cl |
| I-875 | 2-SO$_2$N(CH$_3$)$_2$ | 4,6-(OCF$_3$)$_2$ |
| I-876 | 2-SO$_2$N(CH$_3$)$_2$ | 4-OCH(CH$_3$)$_2$-6-Cl |
| I-877 | 2-SO$_2$N(CH$_3$)$_2$ | 4-OCH$_2$CH$_2$CF$_3$-6-Cl |
| I-878 | 2-SO$_2$N(CH$_3$)$_2$ | 4-CH$_3$-6-OCH$_3$ |
| I-879 | 2-SO$_2$N(C$_2$H$_5$CH$_3$)$_2$ | 5-OCH$_3$-6-Br |
| I-881 | 2-SO$_2$N(CH$_3$)$_2$ | 4-OCH$_2$CF$_3$-6-Cl |
| I-882 | 2-SO$_2$N(CH$_3$)$_2$ | 4-OCH$_2$F-6-Cl |
| I-883 | 2-SO$_2$N(CH$_3$)$_2$ | 4-OCH$_2$CHF$_2$-6-Cl |
| I-884 | 2-SO$_2$N(CH$_3$)$_2$ | 4-OCH$_3$-6-CH$_3$ |
| I-885 | 2-SO$_2$N(CH$_3$)$_2$ | 4-OCH$_3$-6-Cl |
| I-886 | 2-SO$_2$N(CH$_3$)$_2$ | 4-OCH$_3$ |
| I-887 | 2-SO$_2$N(CH$_3$)$_2$ | 4,6-(OCH$_3$)$_2$ |
| I-888 | 2-SO$_2$N(CH$_3$)$_2$ | 5-OCH$_3$-6-Cl |
| I-889 | 2-SO$_2$N(CH$_3$)$_2$ | 5,6-(OCH$_3$)$_2$ |
| I-890 | 2-SO$_2$N(CH$_3$)$_2$ | 5-OCF$_3$-6-Cl |
| I-891 | 2-SO$_2$N(CH$_3$)$_2$ | 4-OCHF$_2$-6-Cl |
| I-892 | 2-SO$_2$N(CH$_3$)$_2$ | 4-OC$_2$H$_5$-6-Cl |
| I-893 | 2-SO$_2$N(CH$_3$)$_2$ | 4-SCH$_3$-6-Cl |
| I-894 | 2-SO$_2$N(CH$_3$)$_2$ | 4-SCHF$_2$-6-Cl |
| I-895 | 2-SO$_2$N(CH$_3$)$_2$ | 5-OCH$_3$-6-Br |
| I-896 | 2-SO$_2$N(CH$_3$)$_2$ | 5-OCH$_3$-6-F |
| I-897 | 2-SO$_2$N(CH$_3$)$_2$ | 5-OCF$_3$-6-OCH$_3$ |
| I-898 | 2-SO$_2$N(CH$_3$)$_2$ | 5-OCF$_3$-6-Br |
| I-899 | 2-SO$_2$N(CH$_3$)$_2$ | 5-OCF$_3$-6-F |
| I-900 | 2-SO$_2$N(CH$_3$)$_2$ | 5-OCHF$_2$-6-Br |
| I-901 | 2,6-F$_2$ | 4-CF$_3$-6-Cl |
| I-902 | 2,6-F$_2$ | 4-CH(CH$_3$)$_2$-6-Cl |
| I-903 | 2,6-F$_2$ | 4-CH$_2$F-6-Cl |
| I-904 | 2,6-F$_2$ | 4-CH$_2$OCH$_3$-6-Cl |
| I-905 | 2,6-F$_2$ | 4-CH$_2$SCH$_3$-6-Cl |
| I-906 | 2,6-F$_2$ | 4-CH$_3$-6-OCH$_3$ |
| I-907 | 2,6-F$_2$ | 4-CHF$_2$-6-Cl |
| I-911 | 2,6-F$_2$ | 4-Cl-6-CF$_3$ |
| I-912 | 2,6-F$_2$ | 4-Cl-6-CH(CH$_3$)$_2$ |
| I-913 | 2,6-F$_2$ | 4-Cl-6-CH$_2$F |
| I-914 | 2,6-F$_2$ | 4-Cl-6-CH$_2$OCH$_3$ |
| I-915 | 2,6-F$_2$ | 4-Cl-6-CH$_2$SCH$_3$ |
| I-916 | 2,6-F$_2$ | 4-Cl-6-CHF$_2$ |
| I-917 | 2,6-F$_2$ | 4,6-Cl$_2$ |
| I-921 | 2,6-F$_2$ | 4-Cl-6-F |
| I-922 | 2,6-F$_2$ | 4-Cl |
| I-923 | 2,6-F$_2$ | 4-Cl-6-N(CH$_3$)$_2$ |
| I-924 | 2,6-F$_2$ | 4-Cl-6-N(CH$_3$)C2H |
| I-925 | 2,6-F$_2$ | 4-Cl-6-NH$_2$ |
| I-926 | 2,6-F$_2$ | 4-Cl-6-NHCH$_3$ |
| I-927 | 2,6-F$_2$ | 4-Cl-6-OCF$_2$CHF$_2$ |
| I-931 | 2,6-F$_2$ | 4-Cl-6-OCF$_2$CHFCl |
| I-932 | 2,6-F$_2$ | 4-Cl-6-OCF$_3$ |
| I-933 | 2,6-F$_2$ | 4-Cl-6-OCH(CH$_3$)$_2$ |
| I-934 | 2,6-F$_2$ | 4-Cl-6-OCH$_2$CH$_2$CF$_3$ |
| I-935 | 2,6-F$_2$ | 4-Cl-6-OCH$_2$CF$_3$ |
| I-936 | 2,6-F$_2$ | 4-Cl-6-OCH$_2$CH$_2$F |
| I-937 | 2,6-F$_2$ | 4-Cl-6-OCH$_2$CHF$_2$ |
| I-941 | 2,6-F$_2$ | 4-Cl-6-OCH$_3$ |
| I-942 | 2,6-F$_2$ | 4-Cl-6-OCHF$_2$ |
| I-943 | 2,6-F$_2$ | 4-Cl-6-OC$_2$H$_5$ |
| I-944 | 2,6-F$_2$ | 4-Cl-6-SCH$_3$ |
| I-945 | 2,6-F$_2$ | 4-Cl-6-SCHF$_2$ |
| I-946 | 2,6-F$_2$ | 4-F-6-Cl |
| I-947 | 2,6-F$_2$ | 4-F-6-OCH$_3$ |
| I-951 | 2,6-F$_2$ | 6-Cl |
| I-952 | 2,6-F$_2$ | (No substituted) |
| I-953 | 2,6-F$_2$ | 6-OCH$_3$ |
| I-954 | 2,6-F$_2$ | 5-OCH$_3$ |
| I-955 | 2,6-F$_2$ | 4-N(CH$_3$)$_2$-6-Cl |
| I-956 | 2,6-F$_2$ | 4-N(CH$_3$)C$_2$H$_5$-6-Cl |
| I-957 | 2,6-F$_2$ | 4-NH$_2$-6-Cl |
| I-961 | 2,6-F$_2$ | 4-NHCH$_3$-6-Cl |
| I-962 | 2,6-F$_2$ | 4-OCF$_2$CHF$_2$-6-Cl |
| I-963 | 2,6-F$_2$ | 4-OCF$_2$CHFCl-6-Cl |
| I-964 | 2,6-F$_2$ | 4-OCF$_3$-6-Cl |
| I-965 | 2,6-F$_2$ | 4,6-(OCF$_3$)$_2$ |
| I-966 | 2,6-F$_2$ | 4-OCH(CH$_3$)$_2$-6-Cl |
| I-967 | 2,6-F$_2$ | 4-OCH$_2$CH$_2$CF$_3$-6-Cl |
| I-971 | 2,6-F$_2$ | 4-OCH$_2$CF$_3$-6-Cl |
| I-972 | 2,6-F$_2$ | 4-OCH$_2$F-6-Cl |
| I-973 | 2,6-F$_2$ | 4-OCH$_2$CHF$_2$-6-Cl |

TABLE 1-continued

| Compound | Xn | Ym |
| --- | --- | --- |
| I-974 | 2,6-F$_2$ | 4-OCH$_3$-6-CH$_3$ |
| I-975 | 2,6-F$_2$ | 4-OCH$_3$-6-Cl |
| I-976 | 2,6-F$_2$ | 4-OCH$_3$ |
| I-977 | 2,6-F$_2$ | 4,6-(OCH$_3$)$_2$ |
| I-978 | 2,6-F$_2$ | 5-OCH$_3$-6-Cl |
| I-979 | 2,6-F$_2$ | 5,6-(OCH$_3$)$_2$ |
| I-980 | 2,6-F$_2$ | 5-OCF$_3$-6-Cl |
| I-981 | 2,6-F$_2$ | 4-OCHF$_2$-6-Cl |
| I-982 | 2,6-F$_2$ | 4-OC$_2$H$_5$-6-Cl |
| I-983 | 2,6-F$_2$ | 4-SCH$_3$-6-Cl |
| I-984 | 2,6-F$_2$ | 4-SCHF$_2$-6-Cl |
| I-985 | 2,6-F$_2$ | 5-OCH$_3$-6-Br |
| I-986 | 2,6-F$_2$ | 5-OCH$_3$-6-F |
| I-987 | 2,6-F$_2$ | 5-OCF$_3$-6-OCH$_3$ |
| I-988 | 2,6-F$_2$ | 5-OCF$_3$-6-Br |
| I-989 | 2,6-F$_2$ | 5-OCH$_3$-6-F |

In the first and the second processes according to the present invention, one or more of the following solvents can be used in the reaction steps and the step for isolation of the product.

Aromatic hydrocarbons such as benzene, toluene, xylene, methylnaphthalene, etc.

Aliphatic hydrocarbons such as petroleum ether, pentane, hexane, heptane, methylcyclohexane, etc.

Chlorinated hydrocarbons such as methylene chloride, chloroform, carbon tetrachloride, 1,2-dichloroethane, tetrachloroethane, chlorobenzene, etc.

Amides such as N,N-dimethylformamide, N,N-dimethylacetamide, N-methyl-2-pyrrolidinone, etc.

Ethers such as diethyl ether, dimethoxyethane, diisopropyl ether, tetrahydrofuran, diglyme, dioxane, etc.

Lower alkyl alcohols such as methyl alcohol, ethyl alcohol, 1-methyl alcohol, 1,1-dimethylethyl alcohol, etc.

The other solvents such as water, carbondioxide, acetonitrile, nitromethane, ethyl acetate, acetic acid, propionic acid, pyridine, methylsulfoxide, hexamethyl phosphoric amide, etc.

Reactions of the first and the second processes according to the present invention are preferably carried out in a solvent or a solvent mixture. It is possible for the reactions to use a solvent composition consisting of solvents which do not form a homogeneous phase one another. In such a case, it is suitable to add to the reaction system a phase-transfer catalyst, for example, common quaternary ammonium salt or crown ether.

When it is desired to use a salt in the reaction step or the step for separation of the product, one or more of the following salts can be used in the present invention.

Alkali metals such as lithium, sodium, potassium, etc., and alkaline earth metals such as magnesium, etc.

Alkali metal alkoxides such as sodium methoxide, sodium ethoxide, potassium t-butoxide, etc.

Alkali metal hydrides such as sodium hydride, potassium hydride, etc.

Alkali metal hydrogencarbonate such as potassium hydrogencarbonate, sodium hydrogencarbonate, etc.

Alkali metal hydroxide such as sodium hydroxide, potassium hydroxide, etc.

Alkaline earth metal hydroxide such as magnesium hydroxide, calcium hydroxide, etc.

Alkaline earth metal oxides such as magnesium oxide, calcium oxide, etc.

Alkali metal carbonates such as potassium carbonate, sodium carbonate, etc.

Alkaline earth metal hydrides such as calcium hydride, etc.

Organometallic compounds of alkali metal such as methyllithium, ethyllithium, butyllithium, sec-butyllithium, tert-butyllithium, phenyllithium, etc.

Organic Grignard reagents such as methylmagnesium iodide, ethylmagnesium bromide, n-butylmagnesium bromide, etc.

Organocopper compounds prepared from an organometallic compound of alkali metal or a Grignard reagent and a monovalent copper salt.

Alkali metal amides such as lithium diisopropylamide, etc.

Organic amines such as triethylamine, pyridine, 4-dimethylaminopyridine, N,N-dimethylaniline, 1,8-diazabicyclo[5.4.0]undeca-7-ene (referred as DBU, hereinafter)

When it is desired to use an acid in the reaction step or the step for separation of the product, one or more of the following acids can be used in the present invention.

Inorganic acids such as hydrochloric acid, hydrobromic acid, hydroiodic acid, perchloric acid, sulfuric acid, etc.; organic acids such as formic acid, acetic acid, butyric acid, p-toluenesulfonic acid, etc.; and Lewis acid such as boron trifluoride, aluminum chloride, zinc chloride, etc.

The N-(phenylsulfonyl)picolinamide derivatives of the above formula (I) according to the present invention can be produced by condensation reaction of 1 mol of a substituted picolinic acid of the above formula (II) with 0.7–1.5 equivalents of a substituted benzenesulfonamide of the above formula (III) under dehydration.

(The First Process for Production)

Upon the condensation reaction under dehydration in the above process for production, 1,3-dicyclohexylcarbodiimide, diethyl cyanophosphate, 1,1'-carbonyldiimidazole, thionyl chloride, etc are used generally as the dehydration-condensation agent, and chlorinated hydrocarbons such as methylene chloride, chloroform, 1,2-dichloroethane, etc. and ethers such as diethyl ether, tetrahydrofuran, dioxane, etc. are used generally as the solvent. Preferably, 1,3-dicyclohexylcarbodiimide is used as the dehydration-condensation agent and dichloromethane, tetrahydrofuran or dioxane is used as the solvent.

In the above described process for production, the substituted benzenesulfonamide of the above formula (III) and the substituted picolinic acid of the above formula (II) are mixed with the dehydration-condensation agent and the solvent, and the mixture was generally allowed to react at a temperature of 0–30° C., and preferably at 0–5° C. and then at 15–30° C. The reaction period of time is 1–6 hours and preferably 3–4 hours. This reaction is advantageously carried out in the presence of 4-dimethylaminopyridine.

The N-(phenylsulfonyl)picolinamide derivatives of the above formula (I) according to the present invention can be produced by reacting a substituted picolinic acid phenyl ester of the above formula (IV) with a substituted benzenesulfonamide of the formula (III) in a solvent, preferably in an aprotic polar solvent in the presence of a basic compound.

(The second process for production)

This process is suitable in case of using a substituted compound in which substituents in ortho positions of the sulfamoyl group on the benzene ring do not cause ring-closure condensation with the sulfamoyl group under a basic condition. Such substituents include halogen atoms, C1–C4 alkyl groups, C1–C4 haloalkyl groups, C1–C4 alkoxy groups, C1–C4 haloalkoxy groups, (di-C1–C4 alkylamino) sulfonyl groups, [N—(C1–C4 alkyl)-N—(C1–C4 alkoxy) amino]sulfonyl groups, (C1–C4 alkylamino)sulfonyl groups, C1–C4 alkylthio groups, C1–C4 alkylsulfonyl groups and nitro group.

Specific examples of the substituents Xn include 2-$CF_3$, 2-$CH_3$, 2,3-$Cl_2$, 2,4-$Cl_2$, 2,5-$Cl_2$, 2,6-$Cl_2$ 2-Cl, 2-$OCF_3$, 2-$SO_2N(CH_3)_2$, 2-$SO_2N(CH_2CH_3)_2$, 2-$SO_2N(OCH_3)(CH_3)$, 2,6-$F_2$, 2-$SO_2NHCH_3$, 2-$SCH_3$ and 2-$SO_2CH_3$.

The above mentioned reaction step is preferred to carry out in an inert organic solvent, for example, hydrocarbon such as benzene, toluene, xylene or cyclohexane, chlorinated hydrocarbon such as methylene chloride, chloroform, carbon tetrachloride or chlorobenzene, or ether such as diethyl ether, dimethoxyethane, diethylene glycol, dimethyl ether, tetrahydrofuran or dioxane, or in an aprotic polar solvent such as acetonitrile, nitromethane, N,N-dimethylformamide, N,N-dimethylacetamide or methylsulfoxide, and preferably, N,N-dimethylformamide or N,N-dimethylacetamide, at temperature of −10–160° C., preferably 20–100° C. In this reaction, sodium hydride or DBU is preferably used as the basic compound. Further, the reaction period of time is 1–5 hours, and preferably 1.5–2.5 hours.

The substituted picolinic acid of the formula (II) used in the first process for producing the N-(phenylsulfonyl) picolinamide of the formula (I) according to the present invention are listed in Table 2. It is possible to derive from these compounds the substituted picolinic acid phenyl esters of the formula (IV) used as the starting material in the second process according to the present invention.

TABLE 2

| Compound No. | Ym (Note) |
|---|---|
| II-1 | 4-$CF_3$-6-Cl |
| II-2 | 4-$CH(CH_3)_2$-6-Cl |
| II-3 | 4-$CH_2F$-6-Cl |
| II-4 | 4-$CH_2OCH_3$-6-Cl |
| II-5 | 4-$CH_2SCH_3$-6-Cl |
| II-6 | 4-$CH_3$-6-$OCH_3$ |
| II-7 | 4-$CHF_2$-6-Cl |
| II-8 | 4-$CH_3$-6-Cl |
| II-9 | 3,6-$Cl_2$ |
| II-11 | 4-Cl-6-$CF_3$ |
| II-12 | 4-Cl-6-$CH(CH_3)_2$ |
| II-13 | 4-Cl-6-$CH_2F$ |
| II-14 | 4-Cl-6-$CH_2OCH_3$ |
| II-15 | 4-Cl-6-$CH_2SCH_3$ |
| II-16 | 4-Cl-6-$CH_2F$ |
| II-17 | 4,6-$Cl_2$ |
| II-21 | 4-Cl-6-F |
| II-22 | 4-Cl |
| II-23 | 4-Cl-6-$N(CH_3)_2$ |
| II-24 | 4-Cl-6-$N(CH_3)C_2H_5$ |
| II-25 | 4-Cl-6-$NH_2$ |
| II-26 | 4-Cl-6-$NHCH_3$ |
| II-27 | 4-Cl-6-$OCF_2CHF_2$ |
| II-31 | 4-Cl-6-$OCF_2CHFCl$ |
| II-32 | 4-Cl-6-$OCF_3$ |
| II-33 | 4-Cl-6-$OCH(CH_3)_2$ |
| II-34 | 4-Cl-6-$OCH_2CH_2CF_3$ |
| II-35 | 4-Cl-6-$OCH_2CF_3$ |
| II-36 | 4-Cl-6-$OCH_2CH_2F$ |
| II-37 | 4-Cl-6-$OCH_2CHF_2$ |
| II-41 | 4-Cl-6-$OCH_3$ |
| II-42 | 4-Cl-6-$OCHF_2$ |
| II-43 | 4-Cl-6-$OC_2H_5$ |
| II-44 | 4-Cl-6-$SCH_3$ |
| II-45 | 4-Cl-6-$SCHF_2$ |
| II-46 | 4-F-6-Cl |
| II-47 | 4-F-6-$OCH_3$ |

TABLE 2-continued

| Compound No. | Ym (Note) |
|---|---|
| II-51 | 6-Cl |
| II-52 | (No substituted) |
| II-53 | 6-$OCH_3$ |
| II-54 | 5-$OCH_3$ |
| II-55 | 4-$N(CH_3)_2$-6-Cl |
| II-56 | 4-$N(CH_3)C_2H_5$-6-Cl |
| II-57 | 4-$NH_2$-6-Cl |
| II-61 | 4-$NHCH_3$-6-Cl |
| II-62 | 4-$OCF_2CHF_2$-6-Cl |
| II-63 | 4-$OCF_2CHFCl$-6-Cl |
| II-64 | 4-$OCF_3$-6-Cl |
| II-65 | 4,6-$(OCF_3)_2$ |
| II-66 | 4-$OCH(CH_3)_2$-6-Cl |
| II-67 | 4-$OCH_2CH_2CF_3$-6-Cl |
| II-71 | 4-$OCH_2CF_3$-6-Cl |
| II-72 | 4-$OCH_2CH_2F$-6-Cl |
| II-73 | 4-$OCH_2CHF_2$-6-Cl |
| II-74 | 4-$OCH_3$-6-$CH_3$ |
| II-75 | 4-$OCH_3$-6-Cl |
| II-76 | 4-$OCH_3$ |
| II-77 | 4,6-$(OCH_3)_2$ |
| II-78 | 5-$OCH_3$-6-Cl |
| II-79 | 5,6-$(OCH_3)_2$ |
| II-80 | 5-$OCF_3$-6-Cl |
| II-81 | 4-$OCHF_2$-6-Cl |
| II-82 | 4-$OC_2H_5$-6-Cl |
| II-83 | 4-$SCH_3$-6-Cl |
| II-84 | 4-$SCHF_2$-6-Cl |
| II-85 | 5-$OCH_3$-6-Br |
| II-86 | 5-$OCH_3$-6-F |
| II-87 | 5-$OCF_3$-6-$OCH_3$ |
| II-88 | 5-$OCF_3$-6-Br |
| II-89 | 5-$OCF_3$-6-F |
| II-90 | 5-$OCHF_2$-6-Br |
| II-91 | 5-$OCH_3$-6-$NO_2$ |
| II-92 | 5-$NO_2$-6-$CH_3$ |
| II-93 | 5-$OCH_3$-6-$N(CH_3)_2$ |

(Note):
The rule of notation regarding Ym is the same as in Table 1. But, the carboxyl group is attached to 2-position of the pyridine ring in Table 2, while the N-substituted carbamoyl group is attached to 2-position in Table 1.

In the following, starting materials used in the present invention will be illustrated in detail.

The substituted picolinic acid of the formula (II) and the substituted picolinic acid lower alkyl ester of the following formula (V) which is the starting material thereof can be synthesized according to the following reactions (1)–(3), whereby the carboxyl group or the lower alkoxycarbonyl group can be formed on the 2-position of the pyridine ring.

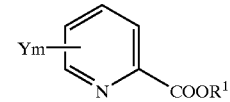

(V)

wherein Y is halogen atom, C1–C4 alkyl group, C1–C4 haloalkyl group, C1–C4 alkoxy group, C1–C4 haloalkoxy group, C1–C4 alkylthio group, C1–C4 haloalkylthio group, amino group, C1–C4 alkylamino group, di-C1–C4 alkylamino group, (C1–C4 alkoxy) C1–C4 alkyl group, (C1–C4 alkylthio) C1–C4 alkyl group or nitro group, m is an integer of 0–4, and each Y may be identical or different in case of m being 2 or more, and $R^1$ represents C1–C4 alkyl group.

(1) Substituted picolinic acid lower alkyl ester having a lower alkoxycarbonyl group derived from hydroxycarbonyl group of the starting material prior to formation of the pyridine ring:

As be shown in the following reaction formula, 4,6-dichloropicolinic acid lower alkyl ester of the formula (VI) can be synthesized by reacting N-methylpyridonic acid of the formula (VIII) with thionyl chloride to prepare 4,6-dichloropicolinic acid chloride of the formula (VII), followed by reacting the resultant compound of the formula (VII) with lower alkyl alcohol.

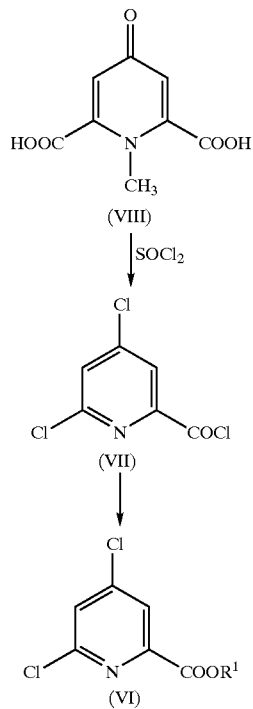

wherein $R^1$ is C1–C4 alkyl group.

(2) Substituted picolinic acid obtained by oxidation of 2-methyl group or 2-hydroxymethyl group on the pyridine ring:

The substituted 2-picolinic acid of the formula (II) can be synthesized by oxidation of a substituted 2-picoline (or substituted 2-pyridine methanol) of the following formula (IX).

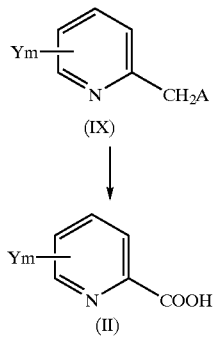

wherein Y and m are each the same definition as described above, and A represents hydrogen atom or hydroxyl group.

(3) Substituted picolinic acid obtained by hydrolysis of cyano group of substituted picolinonitrile:

The substituted picolinic acid of the formula (II) can be synthesized by hydrolyzing a substituted picolinonitrile of the formula (X) according the following reaction formula.

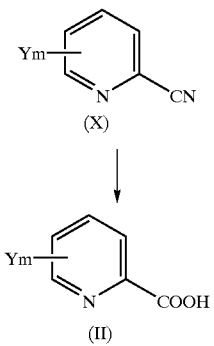

wherein Y and m means the same definition as described above.

Among the above-described 3 reactions, since the reaction process (1) causes simultaneous chlorination of 4- and 6-positions of the pyridine ring, these chlorine atoms can be utilized as releasable groups in nucleophilic substitution reactions.

As be shown in the following reaction formula, the 4,6-disubstituted picolinic acid lower alkyl ester of the following formula (XI) can be synthesized by nucleophilically substituting chlorine atoms on 4-position and/or 6-position of 4,6-dichloro-picolinic acid lower alkyl ester of the above formula (VI).

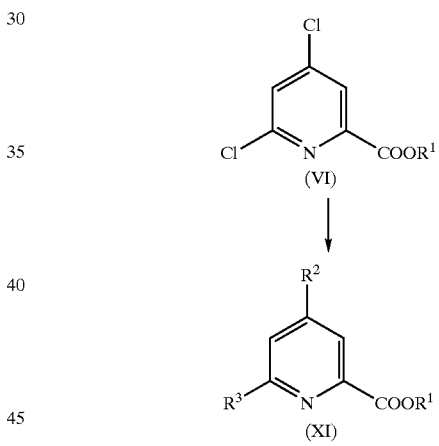

wherein $R^2$ and $R^3$ represent independently chlorine atom, C1–C4 alkoxy group, C1–C4 haloalkoxy group, C1–C4 alkylthio group, C1–C4 haloalkylthio group, amino group, C1–C4 alkylamino group or di-C1–C4 alkylamino group, and $R^1$ represents C1–C4 alkyl group, but $R^2$ and $R^3$ are not chlorine atom at the same time Among the 4,6-di-substituted picolinic acid lower alkyl ester of the above formula (XI), compounds having a chlorine atom attached to one of 4-position or 6-position, and a C1–C4 alkoxy group, C1–C4 haloalkoxy group, C1–C4 alkylthio group, C1–C4 haloalkylthio group, amino group, C1–C4 alkylamino group or di-C1–C4 alkylamino group attached to the other position can be synthesized by nucleophilic substitution reaction of the chlorine atom on the 4-position or 6-position under the basic condition.

Upon carrying out this nucleophilic substitution reaction, they can be synthesized by selecting the solvent to be used, by which either one of chlorine atoms on 4-position and 6-position causes the nucleophilic substitution under the basic condition.

In addition, compound in which the same or different substituents selected from C1–C4 alkoxy group, C1–C4 haloalkoxy group, C1–C4 alkylthio group, C1–C4 haloalkylthio group, amino group, C1–C4 alkylamino group or di-C1–C4 alkylamino group are attached to both of 4-position and 6-position can be synthesized from the compounds (XI) by nucleophilic substitution reaction of the chlorine atoms on the 4-position and 6-position under the basic condition. In this case, after substitution of one of chlorine atoms on 4-position and 6-position, the other chlorine atom may be substituted, or the both chlorine atoms may be substituted simultaneously.

Among the above reaction processes (1)–(3), the reaction process (2) is suitable for synthesis of substituted picolinic acids in which at least a substituent Y is C1–C4 alkoxy group or C1–C4 haloalkoxy group attached to 5-position.

Compounds of the following formula (XII) having a C1–C4 alkoxy group or C1–C4 haloalkoxy group attached to 5-position can be synthesized, according to the following reaction formula, by converting 5-hydroxyl group of 5-hydroxy-2-picoline of the formula (XIV) to an ether bond by C1–C4 alkylation or C1–C4 haloalkylation to produce 5-substituted-2-picoline of the formula (XIII), followed by converting 2-methyl group into carboxyl group by oxidation.

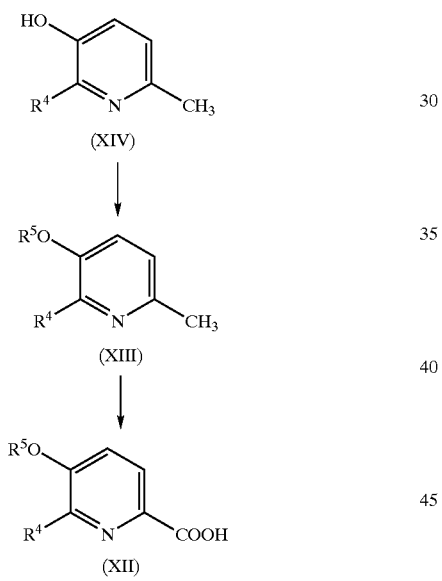

wherein $R^4$ represents hydrogen atom, chlorine atom, bromine atom or nitro group, and $R^5$ represents C1–C4 alkyl group or C1–C4 haloalkyl group.

Substituted picolinic acids having a chlorine atom attached to 6 position can be synthesized using 6-chlorinated compound [compound (XIV,$R^4$=Cl)] of 5-hidroxy-2-methylpyridine as the starting material. Further, as shown in the following reaction formula, substituted picolinic acid alkyl ester compounds of the formula (XV) having a C1–C4 alkoxy group or C1–C4 haloalkoxy group attached to 5 position and having a C1–C4 alkoxy group, C1–C4 haloalkoxy group, C1–C4 alkylthio group, C1–C4 haloalkylthio group, amino group, C1–C4 alkylamino group or di-C1–C4 alkylamino attached to 6 position can be derived by nucleophilic substitution reaction of the 6-chlorine atom of 5-substituted-6-chloropicolinic acid lower alkyl ester of the formula (XVI) which was obtained by converting carboxyl group into lower alkyl ester.

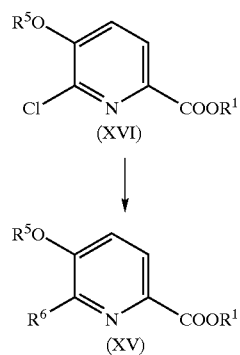

wherein $R^5$ represents C1–C4 alkyl group or C1–C4 haloalkyl group, $R^6$ represents C1–C4 alkoxy group, C1–C4 haloalkoxy group, C1–C4 alkylthio group, C1–C4 haloalkylthio group, amino group, C1–C4 alkylamino group or di-C1–C4 alkylamino group and $R^1$ represents C1–C4 alkyl group.

Upon synthesizing the substituted picolinic acid by oxidation reaction, when pyridine ring has a substituent on 4 position, it is preferred to use a process which comprises synthesizing 2-pyridinemethanol from 2-picoline-N-oxides and oxidizing the formed hydroxymethyl group into carboxyl group as compared with a process which comprises directly converting 2-methyl group on the pyridine ring into carboxyl group by oxidation.

For example, 4-methoxy-6-chloropicolinic acid can be synthesized by oxidation of hydroxymethyl group of 4-methoxy-6-chloro-2-pyridinemethanol, as shown in the following reaction formula.

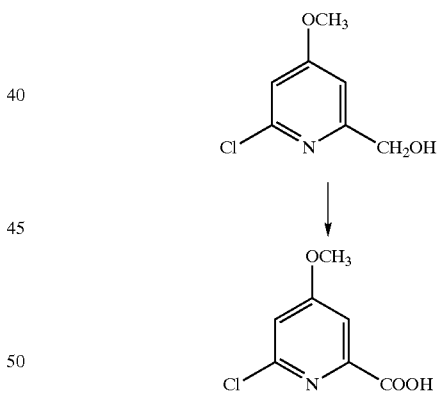

The following reaction formula shows a synthetic process of 4-methoxy-6-chloro-2-pyridinemethanol.

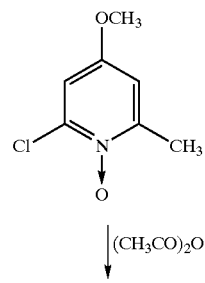

-continued

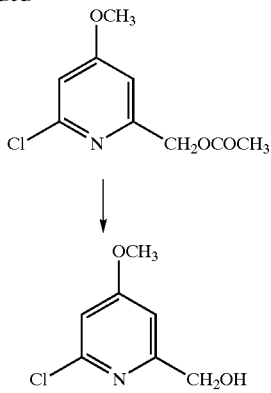

The substituted picolinic acids can be synthesized similarly via hydroxyl group in the case that 4-substituent is halogen atom or nitro group.

Thus resultant substituted picolinic acids may be converted into substituted picolinic acid lower alkyl esters in order to use as starting materials in the nucleophilic substitution reaction for halogen atom or nitro group as the releasable group.

Examples of oxidizing agent used for the above described oxidation reaction include sodium hypochlorite, sodium hypobromide, chlorine, bromine, potassium permanganate, chromic acid and sodium tungstate.

As the reaction solvent, various kinds of solvent, for example, inert solvents such as benzene and chloroform, acetic acid and water, may be used alone or as a mixture thereof.

The reaction temperature is generally 0–100° C., preferably 0–60° C., and the reaction time is from about 30 minutes to 15 days.

The above-mentioned reaction process (3) is suitable for synthesizing substituted picolinic acids using starting materials having C1–C4 alkyl group and/or C1–C4 haloalkyl group as at least one of substituents Y which is capable of being a reaction site for the oxidation reaction in the reaction process (2).

The following reaction formula shows a process for synthesizing substituted picolinic acids of the formula (XVII) using as the starting material 2-cyano-4-substituted-6-methylpyridine of the formula (XVIII) having methyl group as the C1–C4 alkyl group.

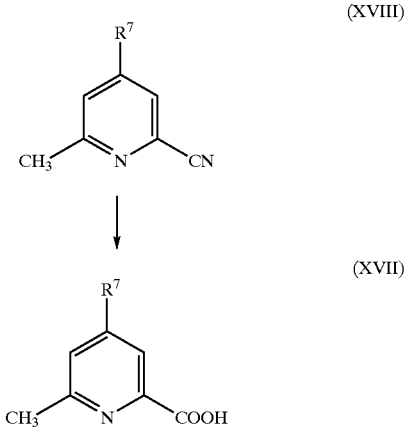

wherein $R^7$ represents hydrogen atom, halogen atom, nitro group, C1–C4 alkoxy group, C1–C4 haloalkoxy group, C1–C4 alkylthio group, C1–C4 haloalkylthio group, amino group, C1–C4 alkylamino group or di-C1–C4 alkylamino group.

The following reaction formula shows a process for synthesizing substituted picolinic acids of the formula (XXIX) using as the starting material 2-cyano-4-methyl-6-substituted pyridine of the formula (XXVIII) having methyl group as the C1–C4 alkyl group.

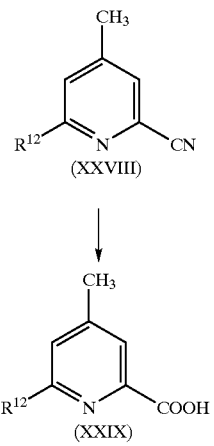

wherein $R^{12}$ represents hydrogen atom, halogen atom, nitro group, C1–C4 alkoxy group, C1–C4 haloalkoxy group, C1–C4 alkylthio group, C1–C4 haloalkylthio group, amino group, C1–C4 alkylamino group or di-C1–C4 alkylamino group.

The following reaction formula shows a synthetic route of 2-cyano-4-nitro-6-methylpyridine [Compound (XVIII), $R^7=NO_2$]

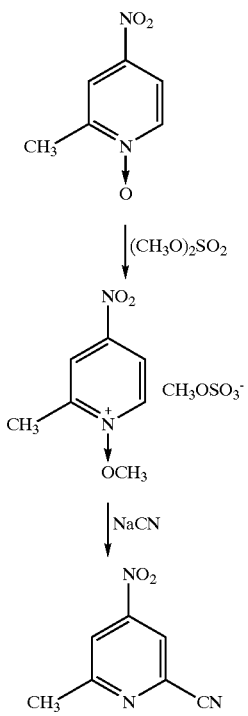

According to the above mentioned reaction formula, 2-picoline-N-oxide is allowed to react with dimethyl sulfate to derive a pyridinium monomethyl sulfate ester salt having methoxy group attached to the nitrogen atom of 1-position, followed by reacting with prussiate such as sodium prussiate to prepare a cyano-ion adduct. The 2-cyano-4-nitro-6-methylpyridine can be prepared by demethanolation of the adduct.

The following reaction formula shows a synthetic route of 2-cyano-substituted pyridines [Compound (XXXII)].

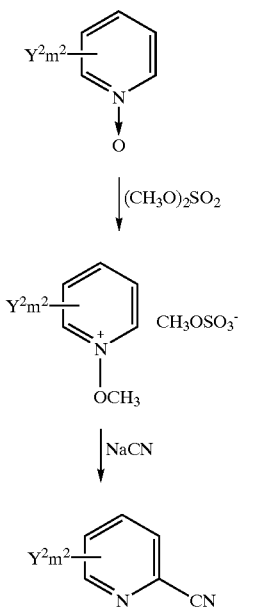

wherein $Y^2$ represents halogen atom, C1–C4 alkyl group, C1–C4 haloalkyl group, C1–C4 alkoxy group, C1–C4 haloalkoxy group, (C1–C4 alkoxy) C1–C4 alkyl group or nitro group, $m^2$ is an integer of 0–4, and each $Y^2$ may be identical or different when $m^2$ is 2 or more.

The substituted pyridine-N-oxides [Compound (XXX)] are allowed to react with dimethyl sulfate to introduce into substituted pyridinium monomethyl sulfate ester salts having methoxy group on the nitrogen atom of 1-position [Compound (XXXI)], followed by reacting with prussiate such as sodium prussiate to obtain cyano-ion adducts. 2-Cyano-substituted pyridines [Compound (XXXII)] can be prepared by demethanolation of adducts.

The following reaction formula shows a synthetic route of 2-cyano-5-methoxy-6-methylpyridine using dimethylcarbamoyl chloride and cyanotrimethyl silane.

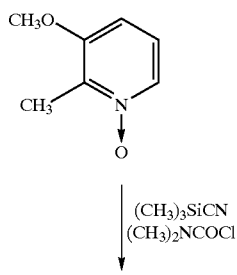

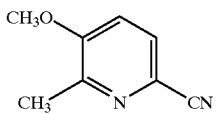

2-Cyano-4-substituted-6-methylpyridines of the formula (XIX) which have a C1–C4 alkoxy group, C1–C4 haloalkoxy group, C1–C4 alkylthio group, C1–C4 haloalkylthio group, amino group, C1–C4 alkylamino group or di-C1–C4 alkylamino group on 4-position can be synthesized by nucleophilic substitution reaction of the 4-nitro group of 2-cyano-4-nitro-6-methylpyridine [Compound (XVIII), $R^7$=NO$_2$], as shown in the following reaction formula.

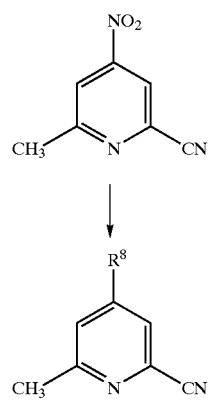

wherein $R^8$ represents C1–C4 alkoxy group, C1–C4 haloalkoxy group, C1–C4 alkylthio group, C1–C4 haloalkylthio group, amino group, C1–C4 alkylamino group or di-C1–C4 alkylamino group.

2-Cyano-4-methyl-6-substituted-pyridines of the formula (XXVII) which have a C1–C4 alkoxy group, C1–C4 haloalkoxy group, C1–C4 alkylthio group, C1–C4 haloalkylthio group, amino group, C1–C4 alkylamino group or di-C1–C4 alkylamino group on 6-position can be synthesized by nucleophilic substitution reaction of chlorine atom on the 6-position of 2-cyano-4-methyl-6-chloropyridine, as shown in the following reaction formula.

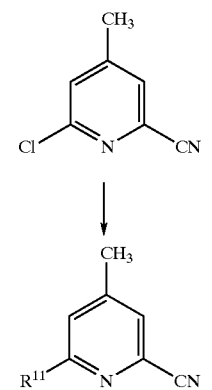

wherein $R^{11}$ represents C1–C4 alkoxy group, C1–C4 haloalkoxy group, C1–C4 alkylthio group, C1–C4 haloalkylthio group, amino group, C1–C4 alkylamino group or di-C1–C4 alkylamino group.

As nucleophilic reagents using for the above-mentioned various nucleophilic substitution reaction on the pyridine ring, the following compounds are exemplified.

C1–C4 Alkyl alcohols such as methyl alcohol, ethyl alcohol and 1-methylethyl alcohol in case of introducing C1–C4 alkoxy group such as $OCH_3$, $OC_2H_5$ or $OCH(CH_3)_2$.

C1–C4 Haloalkyl alcohols such as 2-fluoroethyl alcohol, 2,2-difluoroethyl alcohol, 2,2,2-trifluoroethyl alcohol and 3,3,3-trifluoropropyl alcohol in case of introducing C1–C4 haloalkoxy group such as $OCH_2CH_2F$, $OCH_2CHF_2$, $OCH_2CF_3$ or $OCH_2CH_2CF_3$.

C1–C4 Alkyl thiols such as methyl thiol in case of introducing C1–C4 alkylthio group such as $SCH_3$.

Ammonia in case of introducing amino group.

C1–C4 Alkyl amines such as methylamine in case of introducing C1–C4 alkylamino group such as $NHCH_3$.

Di-C1–C4 Alkyl amines such as dimethylamine and ethyl methylamine in case of introducing di-C1–C4 alkylamino group such as $N(CH_3)_2$ or $N(CH_3)C_2H_5$.

In case of the nucleophilic substitution reaction on the pyridine ring, it is preferred to carry out the reaction in the presence of a basic compound which captures conjugate acid of the releasable group. When the nucleophilic reagent is a basic compound, it may be used in an excess amount.

Further, the alkyl alcohols or alkyl thiols may be used as a state of sodium alkoxide or sodium thioalkoxide, respectively.

Regarding amounts of compounds used for the nucleophilic substitution reaction, the nucleophilic reagent is used in a range of 0.8–1.2 equivalents and the basic compound is used in a range of 0.8–1.2 equivalent based on 1 mol of the starting material. The reaction may be accelerated by using copper salts such as cuprous iodide together with the basic compound, The reaction temperature is in a range of −10–80° C., and the reaction time is in a range of 30 minutes–5 hours.

The reaction is preferably carried out in an aprotic polar solvent such as N,N-dimethylacetamide or acetonitrile, or ether such as dioxane.

On the other hand, the following processes are adopted in order to produce picolinic acids having substituents which are not suitable for introducing into the pyridine ring by nucleophilic substitution reaction.

A process that the methyl group is oxidized after halogenation of the pyridine ring to synthesize the substituted picolinic acid, in case of the substituents being halogen atom such as Cl or F.

A process that the substituted picolinic acid is synthesized via a step of introducing 2-cyano group after halogenation or nitration the pyridine ring, in case of the substituents being halogen atom such as Cl or F and nitro group.

A process that the substituted picolinic acid is synthesized via a step of introducing 2-cyano group into the pyridine ring to which the substituents are attached, in case of the substituents being C1–C4 alkyl group such as $CH_3$ or $CH(CH_3)_2$ or C1–C4 haloalkyl group such as $CH_2F$, $CHF_2$ or $CF_3$.

A process that the substituted picolinic acid is synthesized after the alkyl group of alkyl substituted 2-cyanopyridine is halogenized with N-chlorosuccinimide or N-bromosuccinimide, followed by converting to (C1–C4 alkoxy) C1–C4 alkyl group by alkoxylation or to (C1–C4 alkylthio) C1–C4 alkyl group by alkylthiolation, in case of the substituents being (C1–C4 alkoxy) C1–C4 alkyl group such as $CH_2OCH_3$ or (C1–C4 alkylthio) C1–C4 alkyl group such as $CH_2SCH_3$.

The substituted picolinic acid phenyl ester of the above formula (IV) can be prepared by synthesizing substituted picolinic acid chloride of the formula (XX) from the substituted picolinic acid of the formula (II), followed by reacting with phenol of the formula (XXI) in the presence of a basic compound, as shown in the following reaction formula.

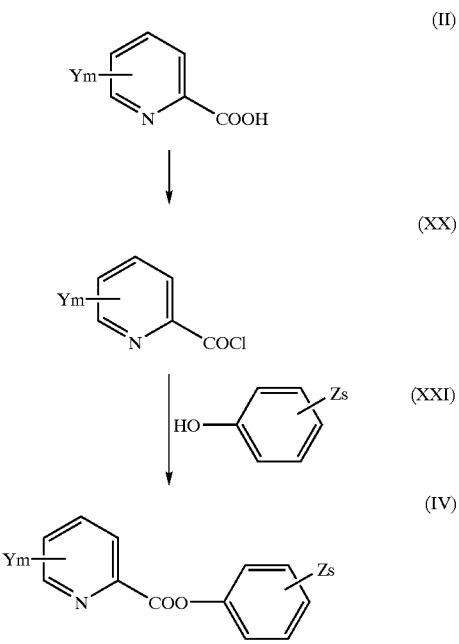

wherein Y and m mean each the same definition as described above, Z represents halogen atom, C1–C4 alkyl group, C1–C4 alkoxy group or nitro group, and s is an integer of 0–5, and each z may be identical or different when s is 2 or more.

In general, the compound of the formula (IV) in which the phenyl group in the phenyl ester portion has no substituent is used as the starting materials for production of the compound (I). However, the phenyl group may have the substituents Z.

Specific examples of the substituent Z include fluorine atom, chlorine atom and bromine atom as halogen atom, methyl group as C1–C4 alkyl group, and methoxy group as C1–C4 alkoxy group s is preferably an integer of 0–3.

The substituted picolinic acid chlorides of the formula (XX) can be synthesized by reacting the substituted picolinic acid of the formula (II) with a chlorinating agent such as thionylchloride in an inert solvent such as benzene, chlorobenzene, etc. at a reaction temperature of 20–120° C., preferably 80–90° C., for a reaction time of 30 minutes–6 hours, preferably 1.5–3 hours.

The substituted picolinic acid phenyl ester of the formula (IV) can be synthesized by reacting the substituted picolinic acid chloride of the formula (XX) with substituted phenol of the formula (XXI) in the presence of a basic compound such as triethylamine, etc. in an inert solvent such as dichloromethane, 1,2-dichloroethane, etc. at a reaction temperature of −10–40° C., preferably 20–25° C. for a reaction time of 30 minutes–6 hours, preferably 2–3 hours.

Examples of the substituted benzenesulfonamides of the above formula (III) used as the starting material in the production step of N-(phenylsulfonyl) picolinic acid amide derivatives of the formula (I) according to the present invention include the following compounds shown in Table 3.

TABLE 3

| Compound No. | Xn (Note) |
|---|---|
| III-1 | 2-CF$_3$ |
| III-2 | 2-CH$_3$ |
| III-3 | 2-COOCH$_3$ |
| III-4 | 2,3-Cl$_2$ |
| III-5 | 2,4-Cl$_2$ |
| III-6 | 2,5-Cl$_2$ |
| III-7 | 2,6-Cl$_2$ |
| III-8 | 2-SO$_2$N(CH$_2$CH$_3$)$_2$ |
| III-11 | 2-Cl |
| III-12 | 2-OCF$_3$ |
| III-13 | 2-SO$_2$N(CH$_3$)$_2$ |
| III-14 | 2,6-F$_2$ |
| III-15 | 2-SO$_2$NHCH$_3$ |
| III-16 | 2-SCH$_3$ |
| III-17 | 2-SOCH$_3$ |
| III-18 | 2-SO$_2$N(OCH$_3$)CH$_3$ |
| III-21 | 5-SO$_2$CH$_3$ |

Note):
The rule of notation regarding Xn is the same as in Table 1. But, the sulfamoyl group is attached to 1-position of the benzene ring in Table 3, while the N-substituted sulfamoyl group is attached to 1-position in Table 1.

The compound of the formula (III) can be produced as follows. As be shown in the following reaction formula, the compound of the formula (III) is synthesized by reacting the substituted benzenesulfonyl chloride of the formula (XXII) with ammonia.

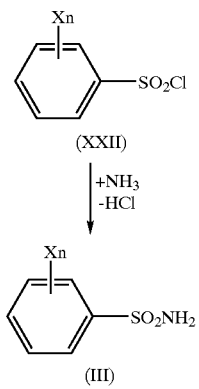

wherein X and n mean the same definitions as described above.

As the substituted benzenesulfonyl chlorides of the above formula (XXII), those available in the market or those prepared by the following process may be used.

In the above reaction, ammonia is used in an amount of about 2–8 times by mol per mol of the compound of the formula (XXII). In general, aqueous ammonia containing 28–30% ammonia is used.

The reaction is carried out by blending a mixture of the compound of the formula (XXII) and an aprotic polar solvent with a mixture of aqueous ammonia and an aprotic polar solvent.

The reaction temperature is in a range of about –20–100° C., preferably –10–30° C., and the reaction time is about 30 minutes–12 hours.

The substituted benzenesulfonyl chloride of the formula (XXII) can be produced according to the following three kinds of process.

(1) Process for producing the substituted benzenesulfonyl chloride of the formula (XXII) which comprises reacting substituted benzene of the formula (XXIII) with chlorosulfric acid as shown in the following reaction formula:

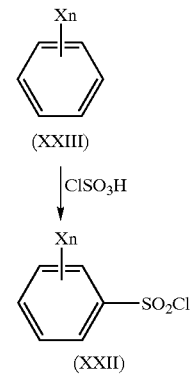

wherein X represents halogen atom, C1–C4 alkyl group, C1–C4 haloalkyl group, C1–C4 alkoxy group, C1–C4 haloalkoxy group, (C1–C4 alkoxy)carbonyl group, (di-C1–C4 alkylamino)sulfonyl group, [N—(C1–C4 alkyl)-N—(C1–C4 alkoxy)amino]sulfonyl group, (C1–C4 alkylamino)sulfonyl group, a C1–C4 alkylthio group, C1–C4 alkylsulfinyl group, C1–C4 alkylsulfonyl group or nitro group, n is an integer of 0–5, and each X may be identical or different when n is 2 or more.

This process for production is suitable in case of using substituted benzene having halogen atoms, C1–C4 alkyl groups, C1–C4 haloalkyl groups, C1–C4 alkoxy groups, C1–C4 haloalkoxy groups etc. as the substituent X.

In this process, chlorosulfuric acid is used in an amount of about 0.8–3 times by mol per mol of the substituted benzene of the formula (XXIII).

The reaction of this process can be carried out in an inert solvent such as carbon disulfide, chloroform, carbon tetrachloride, tetrachloroethane, etc. The reaction temperature is in a range of about 0–200° C., and preferably about 20–120° C. The reaction time is about 20 minutes–few days.

(2) Process for producing substituted benzenesulfonyl chloride of the formula (XXII) which comprises synthesizing the substituted benzenediazonium chloride of the formula (XXIV) from substituted aniline of the formula (XXV), followed by reacting the compound of the formula (XXIV) with sulfur dioxide in the presence of cuprous chloride:

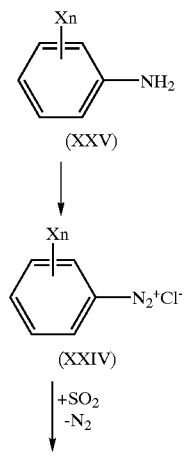

-continued

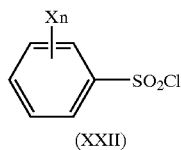
(XXII)

wherein X and n mean each the same definition as described above.

This process for production is suitable in case of using substituted aniline having halogen atoms, C1–C4 alkyl groups, C1–C4 haloalkyl groups, C1–C4 alkoxy groups, C1–C4 haloalkoxy groups, (C1–C4 alkoxy)carbonyl groups, (di-C1–C4 alkylamino)sulfonyl groups, [N—(C1–C4 alkyl)-N—(C1–C4 alkoxy)amino]sulfonyl groups, (C1–C4 alkylamino)sulfonyl groups, C1–C4 alkylthio groups, C1–C4 alkylsulfonyl groups, etc. as the substituent X.

The diazotization reaction of substituted anilines of the above formula (XXV) or salts thereof can be carried out under conventional conditions, for example, by reacting with sodium nitrite in hydrochloric acid under cooling to $-20$–$10°$ C., by which the substituted benzenediazonium chloride of the above formula (XXIV) is synthesized. This substituted benzenediazonium chloride is then allowed to react with sulfur dioxide in the presence of cuprous chloride to produce the substituted benzenesulfonyl chloride of the above formula (XXII).

Amounts of each reagent used for synthesis of the substituted benzenediazonium chloride of the formula (XXIV) are as follows.

The amount of sodium nitrite used is about 1.2 times by mol per mol of substituted aniline of the formula (XXV) or salt thereof.

The amount of hydrochloric acid used is usually 2.5–6 times by mol per mol of substituted aniline of the formula (XXV) or salt thereof. Aqueous solution of 35% concentration is preferably used.

Lower alkanoic acid such as acetic acid or propionic acid may be used as a reaction solvent together with aqueous hydrochloric acid.

Amounts of each reagent used for synthesis of the substituted benzenesulfonyl chloride of the formula (XXII) are as follows.

Cuprous chloride is used in a range of about 0.01–3 times by mol and sulfur dioxide is used in a range of about 0.8–8 times by mol, per mol of substituted benzenediazonium chloride of the formula (XXIV), but the sulfur dioxide may be used in a large excess amount.

The sulfur dioxide may be introduced as a gas from a gas cylinder, or it may be prepared by mixing sodium hydrogen sulfite with aqueous hydrochloric acid. In such a case, lower alkanoic acid such as acetic acid or propionic acid may be used as a reaction solvent.

Accordingly, in case of conducting the reaction, it is possible to use lower alkanoic acid absorbing the sulfur dioxide gas may be used, or to use a lower alkanoic acid mixture which is prepared by adding aqueous hydrochloric acid to lower alkanoic acid containing sodium hydrogen sulfite at $-10$–$5°$ C. so that sulfur dioxide is generated. In the latter case, 0.8–1.4 times by mol of hydrochloric acid are usually used per mol of sodium hydrogen sulfite in order to generate sulfur dioxide.

The reaction of synthesizing the substituted benzenesulfonyl chloride of the above formula (XXII) by reacting substituted benzenediazonium chloride with sulfur dioxide in the presence of cuprous chloride is conducted under acidic conditions. The reaction temperature is in a range of about $-20$–$100°$ C., preferably $-10$–$30°$ C. The reaction time is in a range of from 30 minutes to 12 hours or so.

(3) Process for producing the substituted benzenesulfonyl chloride of the formula (XXII) which comprises oxidatively chlorinating the 2-valent sulfur substituent of substituted benzene sulfide of the formula (XXVI) with a chlorinating agent in the presence of water as shown in the following reaction formula:

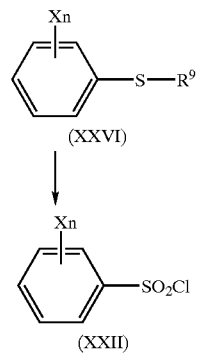

wherein X and n mean each the same definition as described above, and $R^9$ represents hydrogen atom, benzyl group, or phenylthio group having substituents Xn on the benzene ring.

This process for production is suitable in case of using substituted benzene sulfide having substituents such as halogen atom, C1–C4 alkyl group, C1–C4 haloalkyl group, C1–C4 alkoxy group, C1–C4 haloalkoxy group, (C1–C4 alkoxy)carbonyl group, (di-C1–C4 alkylamino)sulfonyl group, [N—(C1–C4 alkyl)-N—(C1–C4 alkoxy)-amino] sulfonyl group, (C1–C4 alkylamino)sulfonyl group, nitro group etc. as the substituent X.

This process is carried out oxidatively chlorinating the 2-valent sulfur substituent of the substituted benzene sulfide of the above formula (XXVI) in the presence of water to derive substituted benzenesulfonyl chloride of the formula (XXII).

Chlorine, sodium hypochlorite, potassium hypochlorite, N-chlorosuccinimide, etc. are used as the chlorinating agent. The chlorinating agent is used in a range of from about 1 to 10 times by mol per mol of the starting compound.

This reaction is preferred to conduct under acidic conditions by adding hydrochloric acid, acetic acid, etc. The reaction temperature is in a range of from about $-10$ to $30°$ C. and the reaction time is in a range of from 30 minutes to 5 hours or so.

Substituted benzenesulfonamides having a C1–C4 alkylsulfinyl group or C1–C4 alkylsulfonyl group of the formula (III-a) can be synthesized by oxidizing a C1–C4 alkylthio group of the substituted benzenesulfonamide having the C1–C4 alkylthio group of the formula (III-b) as shown in the following reaction formula.

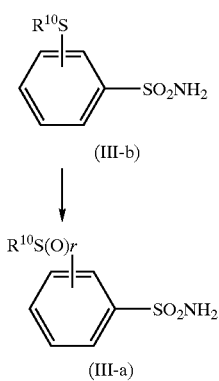

wherein $R^{10}$ represents C1–C4 alkyl group and r is 1 or 2.

Benzenesulfonamides having a C1–C4 alkylsulfonyl group can be prepared as shown in the following reaction formula which comprises protecting amino group of aniline having a C1–C4 alkylthio group, oxidizing the C1–C4 alkylthio group into a C1–C4 alkylsulfonyl group, separating the acetyl group to return to amino group, and converting the amino group into a sulfamoyl group by reactions of synthesizing the compound of the formula (XXII) from the compound of the above formula (XXV) via the compound of the formula (XXIV) or reactions of synthesizing the compound of the formula (III) from the compound of the formula (XXII).

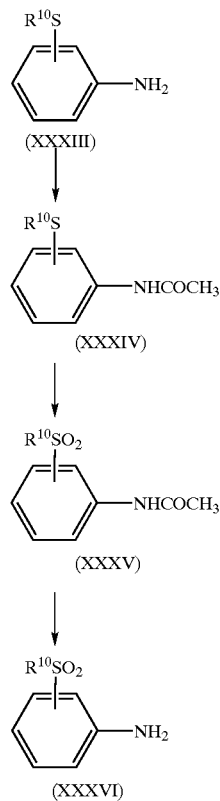

wherein $R^{10}$ represents C1–C4 alkyl group.

Examples of the oxidizing agents used for the above described oxidation reaction include peracids, sodium hypochlorite, chlorine, potassium permanganate and sodium tungstate. Examples of preferable peracids include acetic peracid, benzoic peracid, metachlorobenzoic peracid and phthalic peracid. In case of using acetic peracid, it may be formed during the oxidation step from acetic acid and aqueous hydrogen peroxide.

As the reaction solvent, various kinds of solvent such as inert solvent such as chloroform, and acetic acid, water, etc. can be used alone or as a mixture thereof.

The reaction temperature is usually in a range of about 0 to 100° C., preferably 10–60° C. and the reaction time is in a range of 3 hours to 15 days or so.

For example, the compound can be used as a starting material of the present invention by converting 2-$SCH_3$ into 2-$SOCH_3$ or 2-$SO_2CH_3$ by oxidation.

The process of conversion of the thio bond to the sulfuryl bond or sulfonyl bond by oxidation can be utilized not only for production of substituted benzenesulfonamide of the formula (III) having a plurality of C1–C4 alkylthio groups as the substituents Xn but also for production of substituted benzenesulfonamide of the formula (III) having substituents other than C1–C4 alkylthio groups.

Furthermore, it can be utilized as a process for converting the C1–C4 alkylthio group in the N-(phenylsulfonyl) picolinic acid amide derivatives of the formula (I) having at least one C1–C4 alkylthio group into a C1–C4 alkylsulfonyl group or a C1–C4 alkylsulfinyl group.

The N-(phenylsulfonyl)picolinamide derivatives of the above formula (I) has a 2-substituted carbamoyl group attached to the pyridine ring and an N-substituted sulfamoyl group attached to the benzene ring.

Replacing hydrogen atoms on the nitrogen atoms of the 2-substituted carbamoyl group and the 2-substituted sulfamoyl group by suitable cations can produce salts. These salts are generally metal salts, particularly alkali metal salts or alkaline earth metal salts or, sometimes, alkylated ammonium salts or organic amine salts, which may be produced in a solvent such as water, methanol or acetone at a temperature of 20–100° C. In the present invention, examples of suitable bases for producing salts include alkali metal carbonates, alkaline earth metal carbonates, ammonia and ethanolamine.

The N-(phenylsulfonyl)picolinamide derivatives of the above formula (I) according to the present invention exhibit reliable herbicidal activity at low application dosages and show selectivity between crops and weeds. The herbicides containing these compounds as an active ingredient are therefore suitable for controlling either before or after emergence monocotyledonous weeds and dicotyledonous weeds in important crops such as wheat, rice, corn, soybean, etc.

Exemplary dicotyledonous weeds which can be controlled by the herbicides of the present invention include Amaranthus, Bidens, Stellaria, Abutilon, Convolvulus, Matricaria, Galium, etc.

Exemplary monocotyledonous weeds include Echinochloa, Setaria, Digitaria, Avena, Cyperus, etc.

The applicable places of the herbicides according to the present invention range from agricultural lands such as upland fields, paddy fields, orchard, etc. to non-agricultural lands such as athletic fields, factory sites, etc.

Although the compounds of the present invention may be used alone, they are generally used as various preparation forms such as powder, wettable powder, granule, emulsion, etc. together with preparation aids.

Preparation is carried out such a manner that one or more of the compounds according to the present invention are contained in the composition in an amount of 0.1–95% by weight, preferably 0.5–90% by weight and more preferably 2–70% by weight.

In exemplifying carriers, diluents and surfactants used as the preparation aids, examples of solid carrier include talc, kaolin, bentonite, diatom earth, white carbon, clay, etc. Examples of liquid diluents include water, xylene, toluene, chlorobenzene, cyclohexane, cyclohexanone, methylsulfoxide, N,N-dimethylformamide, ethyl alcohol, 1-methylethyl alcohol, etc.

The surfactants are used according to their effect. Examples of emulsifiers include polyoxyethylene alkylaryl ether, polyoxyethylene sorbitan monolaurate, etc. Examples of dispersing agents include lignin sulfonate, dibutylnaphthalene sulfonate, etc. Examples of wetting agents include alkylsulfonate, alkylphenylsulfonate, etc.

The above preparation herbicides are divided into those which are be used intact and those which are used by diluting with a diluent such as water to a desired concentration. In case of the preparation herbicides using by dilution, it is preferable that the compound of the present invention is in a range of 0.001–1.0%.

The application dosage of the compound according to the present invention is 0.01–10 kg and preferably 0.05–5 kg per ha.

Since the concentration and the application dosage depend on type of formulations, application term, method of application, place to be applied and crops to be applied, they can be varied of course irrespective of the above-described ranges. Moreover, the compound of the present invention may be used together with other active ingredients such as fungicides, insecticides, miticides, and herbicides.

In the following, the present invention will be explained with reference to synthesis examples of N-(phenylsulfonyl) picolinamide derivatives, formulation examples and test examples thereof.

The present invention is not restricted to the following synthesis examples, formulation examples and test examples, if not departing from the spirits thereof.

In the following examples, compound Nos. in Tables 1, 2 and 3 are used for the compounds of the formulas (I), (II) and (III). Compound Nos. used for the picolinic acid phenyl esters of the formula (IV) and the substituted picolinic acid alkyl esters of the formula (V) correspond to the Compound No. of the Compound (II) in Table 2. Accordingly, for example, Compound (IV-17) and Compound (V-17) correspond each compound (II-17) and the substituent Ym of them is 4,6-Cl$_2$.

Similarly, compounds Nos. of the substituted aniline of the formula (XXV) and the substituted benzenesulfonyl chloride of the formula (XXII) correspond each to compound No. of the compound (III) in Table 3. Accordingly, for example, Compound (III-13), Compound (XXII-13) and Compound (XXV-13) correspond each Compound (III-13) and the substituents Xn of them is 2-SO$_2$N(CH$_3$)$_2$.

In the synthesis Examples, the abbreviations in the column for NMR data have the following means. s(single), d(double), t(triple), q(quartet), m(multiple), dd(double doublet), bs(broad single)

EXAMPLE

Synthesis Example 1
Synthesis of N-[(2,6-Dichlorophenyl)sulfonyl]-6-chloro-5-methoxy-2-pyridinecarboxamide [Compound (I-618)]

2,6-Dichlorobenzenesulfonamide [Compound (III-7)] (0.257 g, 1.138 mmol) was dissolved in 5 ml of dry N,N-dimethylformamide. To the resultant solution was added sodium hydride (60% in mineral oil, 0.05 g, 1.138× 1.1 mmol) under cooling with water. After conclusion of bubbling, 5 ml of a solution of 6-chloro-5-methoxypicolinic acid phenyl ester [Compound (IV-78)] (0.3 g, 1.138 mmol) in dry N,N-dimethylformamide was added dropwise thereto.

The mixture was then stirred at 70° C. for 1 hour, and the reaction solution was poured into a mixture of 55 ml of iced-water and 0.44 ml of 35% hydrochloric acid, and a solid precipitate was collected by filtration, followed by washing with water. The resultant solid was washed with a small amount of acetonitrile and dried.

White solid, yield: 0.3181 g, percent yield: 70.7%, m.p.: 183–185° C. IR KBr cm$^{-1}$: 1725, 1590, 1430, 1290, 1200. $^1$H-NMR (60 MHz, CDCl$_3$, δ): 3.9 (3H, s, OCH$_3$), 7.2 (1H, d, J=8 Hz, pyridine ring H), 7.36 (3H, s, aromatic ring H), 7.9 (1H, d, J=8 Hz, pyridine ring H), 10.3 (1H, bs, NH).

Synthesis Example 2
Synthesis of N-[[2-(N,N-Dimethylaminosulfonyl)phenyl]-sulfonyl-5-methoxy-2-pyridinecarboxamide [Compound (I-864)]

To a solution of 2-(N,N-dimethylaminosulfonyl)benzene-sulfonamide [Compound (III-13)] (0.231 g, 0.873 mmol) dissolved in 10 ml of dry N,N-dimethylformamide was added sodium hydride (60% in mineral oil, 0.038 g, 0.873× 1.1 mmol).

After conclusion of bubbling, 5 ml of a solution of 5-methoxypicolinic acid phenyl ester [Compound (IV-54)] (0.2 g, 0.873 mmol) in dry N,N-dimethylformamide was added.

The mixture was then stirred at 70° C. in an oil bath for 2 hours. The reaction solution was then poured into a mixture of 50 ml of iced-water and 0.4 ml of 35% hydrochloric acid, and a solid precipitate was collected by filtration, followed by washing with water and drying to obtain the Compound (I-864).

White solid, yield: 0.32 g, percent yield: 92.3%, m.p.: 190–193° C. IR KBr cm$^{-1}$: 1725, 1428, 1350, 1275, 1179, 753, 564. $^1$H-NMR (60 MHz, CDCl$_3$, δ): 2.85 (6H, s, N—CH$_3$×2), 3.81 (3H, s, OCH$_3$), 7.15 (1H, dd, J=3 Hz, 9 Hz, pyridine ring H), 7.46–7.96 (3H, m, aromatic ring H), 7.90 (1H, d, J=9 Hz, pyridine ring H), 8.15 (1H, d, J=3 Hz, pyridine ring H), 8.36–8.66 (1H, m, aromatic ring H), NH indistinctness.

Synthesis Example 3
Synthesis of 2-[[[(6-Chloro-4-methoxypyridin-2-yl) carbonyl]-amino]sulfonyl]benzoic Acid Methyl Ester [Compound (I-255)]

1,3-Dicyclohexylcarbodiimide (0.242 g, 1.17 mmol), 4-dimethylaminopyridine (0.0127 g, 1.17×0.089 mmol) and 2-methoxycarbonylphenylsulfonamide [Compound (III-3)] (0.252 g, 1.17 mmol) were dissolved in 15 ml of anhydrous dichloromethane. To the resultant solution was added 10 ml of a suspension of 6-chloro-4-methoxypicolic acid [Compound (II-75)] (0.22 g, 1.17 mmol) in of anhydrous dichloromethane at 0–5° C. The stirring was continued at 0–5° C. for 1 hour and then for 3 hours till the mixture became room temperature. Thereafter, the solid was separated by filtration and the filtrate was concentrated. To the residue was added 30 ml of a 2N aqueous solution of sodium carbonate and stirred at room temperature for 10 minutes, followed by carrying out distribution by adding 100 ml of ethyl acetate. After the organic layer was washed with saturated saline solution, it was dried with sodium sulfate, followed by removing ethyl acetate by concentration to obtain a solid. It was purified by silica gel column chromatography to obtain a white solid.

Yield: 0.25 g, percent yield: 55.5%, m.p.: 163–165° C. IR KBr cm$^{-1}$: 3358, 1725, 1590, 1479, 1428, 1359, 1308, 1041. $^1$H-NMR (60 MHz, CDCl$_3$, δ): 3.8 (3H, s, COOCH$_3$ or OCH$_3$), 3.96 (3H, s, COOCH$_3$ or OCH$_3$), 6.9 (1H, d, J=2 Hz, pyridine ring H), 7.4 (1H, d, J=2 Hz, pyridine ring H), 7.5–7.7 (3H, m, aromatic ring H), 8.1–8.4 (1H, m, aromatic ring H), 10.2–10.6 (1H, bs, NH).

Synthesis Example 4

Synthesis of 6-Chloro-N-[(2,6-Dichlorophenyl)sulfonyl]-4-methoxypyridine-2-carboxamide [Compound (I-615)]

1,3-Dicyclohexylcarbodiimide (0.243 g, 1.17 mmol), 4-dimethylaminopyridine (0.013 g, 1.17×0.089 mmol) and 2,6-dichlorobenzenesulfonamide [Compound (III-7)] (0.263 g, 1.17 mmol) were dissolved in 15 ml of anhydrous dichloromethane. To the resultant solution was added 10 ml of a suspension of 6-chloro-4-methoxypicolic acid [Compound (II-75)] (0.218 g, 1.17 mmol) in anhydrous dichloromethane at 0–5° C. The stirring was continued at 0–5° C. for 1 hour and then for 3 hours till the mixture became room temperature. Thereafter, the solid was separated by filtration and the filtrate was concentrated. To the residue was added 30 ml of a 2N aqueous solution of sodium carbonate and stirred at room temperature for about 10 minutes, followed by carrying out distribution by adding 100 ml of ethyl acetate. After the organic layer was washed with saturated saline solution, it was dried with sodium sulfate. It was then concentrated to remove ethyl acetate and the residue was washed with a small amount of warm acetonitrile and separated by filtration.

White solid, yield: 0.184 g, percent yield: 40%, m.p.: 175–178° C. IR KBr cm$^{-1}$: 3346, 2938, 1716, 1632, 1437, 1362, 1212, 1194. $^1$H-NMR (60 MHz, d$_6$-DMSO, δ): 3.8 (3H, s, OCH$_3$), 7.25 (1H, d, J=2 Hz, pyridine ring H), 7.35 (1H, d, J=2 Hz, pyridine ring H), 7.53 (3H, m, aromatic ring H), NH indistinctness.

Synthesis Example 5

Synthesis of N-[(2-Trifluoromethylphenyl)sulfonyl]-5-methoxy-2-pyridinecarboxamide [Compound (I-54)]

Using 2-trifluoromethylbenzenesulfonamide [Compound (III-1)] (0.197 g, 0.87 mmol) and 5-methoxypicolinic acid phenyl ester [Compound (IV-54)] (0.2 g, 0.87 mmol), the Compound (I-54) was synthesized according to the process of Synthesis Example 1.

White solid, yield: 0.262 g, percent yield: 83.7%, m.p.: 153–156° C. IR KBr cm$^{-1}$: 3340, 1722, 1587, 1422, 1398, 1359, 1311, 1272, 1188, 1149, 588, 561. $^1$H-NMR (60 MHz, CDCl$_3$, δ): 3.80 (3H, s, OCH$_3$), 7.16 (1H, dd, J=3 Hz, 9 Hz, pyridine ring H), 7.46–7.80 (3H, m, aromatic ring H), 7.9 (1H, d, J=9 Hz, pyridine ring H), 8.13 (1H, d, J=3 Hz, pyridine ring H), 8.23–8.66 (1H, m, aromatic ring H), NH indistinctness.

Synthesis Example 6

Synthesis of 2-[[[(4-Chloro-6-methoxypyridin-2-yl)carbonyl]-amino]sulfonyl]benzoic Acid Methyl Ester [Compound (I-221)]

Using 2-methoxycarbonylbenzenesulfonamide [Compound (III-3)] (0.229 g, 1.07 mmol) and 4-chloro-6-methoxypicolinic acid [Compound (II-41)] (0.2 g, 1.07 mmol), the Compound (I-221) was synthesized according to the process of Synthesis Example 3.

White solid, yield: 0.0886 g, percent yield: 22.7%, m.p.: 147–149° C. IR KBr cm$^{-1}$: 3352, 1725, 1596, 1470, 1434, 1179, 855, 588. $^1$H-NMR (60 MHz, CDCl$_3$, δ): 3.9 (3H, s, OCH$_3$ or COOCH$_3$), 4.0 (3H, s, OCH$_3$ or COOCH$_3$), 6.9 (1H, d, J=2 Hz, pyridine ring H), 7.4–7.85 (4H, m, aromatic ring H×3, pyridine ring H), 8.1–8.45 (1H, m, aromatic ring H), 10.4–11.0 (1H, bs, NH).

Synthesis Example 7

Synthesis of 2-[[[(5-Methoxypyridin-2-yl)carbonyl]amino]-sulfonyl]benzoic Acid Methyl Ester [Compound (I-234)]

Using 2-methoxycarbonylbenzenesulfonamide [Compound (III-3)] (0.422 g, 1.96 mmol) and 5-methoxypicolinic acid [Compound (II-54)] (0.3 g, 1.96 mmol), the Compound (I-234) was synthesized according to the process of Synthesis Example 3.

White solid, yield: 0.113 g, percent yield: 16.5%, m.p.: 164–165° C. IR KBr cm$^{-1}$: 3316, 1746, 1707, 1392, 1353, 1278, 1179. $^1$H-NMR (60 MHz, CDCl$_3$, δ): 3.81 (3H, s, COOCH$_3$ or OCH$_3$), 3.9 (3H, s, COOCH$_3$ or OCH$_3$), 7.15 (1H, dd, J=3 Hz, 9 Hz, pyridine ring H), 7.35–7.65 (3H, m, aromatic ring H), 7.95 (1H, d, J=9 Hz, pyridine ring H), 8.15 (1H , d, J=3 Hz, pyridine ring H), 8.13–8.36 (1H, m, aromatic ring H), NH indistinctness.

Synthesis Example 8

Synthesis of 2-[[[(4,6-Dimethoxypyridin-2-yl)carbonyl]-amino]sulfonyl]benzoic Acid Methyl Ester [Compound (I-257)]

Using 2-methoxycarbonylbenzenesulfonamide [Compound (III-3)] (0.106 g, 0.49 mmol) and 4,6-dimethoxypicolinic acid [Compound (II-77)] (0.09 g, 0.49 mmol), the Compound (I-257) was synthesized according to the process of Synthesis Example 3.

White solid, yield: 0.14 g, percent yield: 75.6%, m.p.: 156–158° C. IR KBr cm$^{-1}$: 1728, 1617, 1473, 1392, 1347, 1293, 1182. $^1$H-NMR (60 MHz, CDCl$_3$, δ): 3.73 (3H, s, OCH$_3$ or COOCH$_3$), 3.9 (3H, s, OCH$_3$ or COOCH$_3$), 4.0 (3H, s, OCH$_3$), 6.3 (1H, d, J=2 Hz, pyridine ring H), 7.2 (1H, d, J=2 Hz, pyridine ring H), 7.5–7.8 (3H, m, aromatic ring H), 8.1–8.5 (1H, m, aromatic ring H), NH indistinctness.

Synthesis Example 9

Synthesis of 2-[[[(6-Chloro-5-methoxypyridin-2-yl)carbonyl]-amino]sulfonyl]benzoic Acid Methyl Ester [Compound (I-258)]

Using 2-methoxycarbonylbenzenesulfonamide [Compound (III-3)] (0.344 g, 1.6 mmol) and 6-chloro-5-methoxypicolinic acid [Compound (II-78)] (0.3 g, 1.6 mmol), the Compound (I-258) was synthesized according to the process of Synthesis Example 3.

White solid, yield: 0.26 g, percent yield: 43.1%, m.p.: 180–183° C. IR KBr cm$^{-1}$: 3364, 1740, 1713, 1440, 1407, 1362, 1275, 1182, 1059, 855. $^1$H-NMR (60 MHz, CDCl$_3$, δ): 3.9 (3H, s, COOCH$_3$ or OCH$_3$), 3.96 (3H, s, COOCH$_3$ or OCH$_3$), 7.16 (1H, d, J=8 Hz, pyridine ring H), 7.4–7.7 (3H, m, aromatic ring H), 7.9 (1H, d, J=8 Hz, pyridine ring H), 8.1–8.4 (1H, m, aromatic ring H), 10–10.5 (1H, bs, NH).

Synthesis Example 10

Synthesis of N-[(2,3-Dichlorophenyl)sulfonyl]-6-chloro-4-methoxypyridine-2-carboxamide [Compound (I-345)]

Using 2,3-dichlorobenzenesulfonamide [Compound (III-4)] (0.3 g, 1.33 mmol) and 6-chloro-4-methoxypicolinic acid [Compound (II-75)] (0.25 g, 1.33 mmol), the Compound (I-345) was synthesized according to the process of Synthesis Example 3.

White solid, yield: 0.14 g, percent yield: 26.5%, m.p.: 132–135° C. IR KBr cm$^{-1}$: 3358, 1722, 1602, 1560, 1437, 1386, 1167, 1029. $^1$H-NMR (60 MHz, CDCl$_3$, δ): 3.8 (3H, s, OCH$_3$), 6.9 (1H, d, J=2 Hz, pyridine ring H), 7.4 (1H, d, J=2 Hz, pyridine ring H), 7.3–7.4 (1H, m, aromatic ring H), 7.6 (1H, dd, J=2, 8 Hz, aromatic ring H), 8.16 (1H, dd, J=2, 8 Hz, aromatic ring H), NH indistinctness.

Synthesis Example 11
Synthesis of 4,6-Dichloro-N-[(2,6-Dichlorophenyl)sulfonyl]-pyridine-2-carboxamide[Compound (I-557)]

Using 2,6-dichlorobenzenesulfonamide [Compound (III-7)] (0.353 g, 1.56 mmol) and 4,6-dichloropicolinic acid [Compound (II-17)] (0.3 g, 1.56 mmol), the Compound (I-557) was synthesized according to the process of Synthesis Example 3.

White solid, yield: 0.314 g, percent yield: 50.6%, m.p.: 207–210° C. IR KBr cm$^{-1}$: 3358, 1725, 1575, 1437, 1422, 1359, 1200, 1167. $^1$H-NMR (60 MHz, d$_6$-DMSO, δ): 7.55 (3H, s, aromatic ring H), 7.9 (1H, d, J=2 Hz, pyridine ring H), 7.96 (1H, d, J=2 Hz, pyridine ring H), NH indistinctness.

Synthesis Example 12
Synthesis of N-[(2,6-Dichlorophenyl)sulfonyl]-4-chloro-6-methoxy-2-pyridinecarboxamide [Compound (I-581)]

Using 2,6-dichlorobenzenesulfonamide [Compound (III-7)] (0.241 g, 1.07 mmol) and 4-chloro-6-methoxypicolinic acid [Compound (II-41)] (0.2 g, 1.07 mmol), the Compound (I-581) was synthesized according to the process of Synthesis Example 3.

White solid, yield: 0.26 g, percent yield: 62.3%, m.p.: 187–190° C. IR KBr cm$^{-1}$: 3358, 1725, 1632, 1569, 1470, 1431, 1362, 1179, 861, 594. $^1$H-NMR (60 MHz, CDCl$_3$, δ): 3.9 (3H, s, OCH$_3$), 6.9 (1H, d, J=2 Hz, pyridine ring H), 7.35 (3H, s, aromatic ring H), 7.56 (1H, d, J=2 Hz, pyridine ring H), NH indistinctness.

Synthesis Example 13
Synthesis of N-[(2,6-Dichlorophenyl)sulfonyl]-5-methoxy-2-pyridinecarboxamide [Compound (I-594)]

Using 2,6-dichlorobenzenesulfonamide [Compound (III-7)] (0.0986 g, 0.436 mmol) and 5-methoxypicolinic acid [Compound (II-54)] (0.1 g, 0.436 mmol), the Compound (I-594) was synthesized according to the process of Synthesis Example 3.

White solid, yield: 0.1 g, percent yield: 63.7%, m.p.: 176–178° C. IR KBr cm$^{-1}$: 3286, 1707, 1587, 1566, 1434, 1416, 1383, 1362, 1275, 1179, 786, 594. $^1$H-NMR (60 MHz, CDCl$_3$, δ): 3.84 (3H, s, OCH$_3$), 7.0–7.45 (4H, m, aromatic ring H, pyridine ring H), 7.93 (1H, d, J=9 Hz, pyridine ring H), 8.13 (1H, d, J=2 Hz, pyridine ring H), NH indistinctness.

Synthesis Example 14
Synthesis of N-[(2-Chlorophenyl)sulfonyl]-6-chloro-4-methoxypyridine-2-carboxamide [Compound (I-705)]

Using 2-chlorobenzenesulfonamide [Compound (III-11)] (0.255 g, 1.33 mmol) and 6-chloro-4-methoxypicolinic acid [Compound (II-75)] (0.25 g, 1.33 mmol), the Compound (I-705) was synthesized according to the process of Synthesis Example 3.

White solid, yield: 0.27 g, percent yield: 66.3%, m.p.: 175–177° C. IR KBr cm$^{-1}$: 3472, 3292, 1728, 1605, 1434, 1392, 1170, 1035. $^1$H-NMR (60 MHz, CDCl$_3$, δ): 3.8 (3H, s, OCH$_3$), 6.9 (1H, d, J=2 Hz, pyridine ring H), 7.3–7.6 (4H, m, pyridine ring H×1, aromatic ring H×3), 8.0–8.4 (1H, m, aromatic ring H), NH indistinctness.

Synthesis Example 15
Synthesis of N-[(2-Trifluoromethoxyphenyl)sulfonyl]-5-methoxy-2-pyridinecarboxamide [Compound (I-774)]

Using 2-trifluoromethoxybenzenesulfonamide [Compound (III-12)] (0.21 g, 0.87 mmol) and 5-methoxypicolinic acid phenyl ester [Compound (IV-54)] (0.2 g, 0.87 mmol), the Compound (I-774) was synthesized according to the process of Synthesis Example 1.

White solid, yield: 0.374 g, percent yield: 78.9%, m.p.: 153–156° C. IR KBr cm$^{-1}$: 3298, 1722, 1632, 1581, 1482, 1428, 1398, 1359, 1185, 1164. $^1$H-NMR (60 MHz, CDCl$_3$, δ): 3.84 (3H, s, OCH$_3$), 7.16 (1H, dd, J=3 Hz, 9 Hz, pyridine ring H), 7.28–7.60 (3H, m, aromatic ring H), 7.9 (1H, d, J=9 Hz, pyridine ring H), 8.06–8.3 (1H, m, aromatic ring H), 8.15 (1H, d, J=3 Hz, pyridine ring H), NH indistinctness.

Synthesis Example 16
Synthesis of N-[(2-Trifluoromethoxyphenyl)sulfonyl]-6-chloro-4-methoxy-2-pyridinecarboxamide [Compound (I-795)]

Using 2-trifluoromethoxybenzenesulfonamide [Compound (III-12)] (0.23 g, 0.96 mmol) and 6-chloro-4-methoxypicolinic acid [Compound (II-75)] (0.18 g, 0.96 mmol), the Compound (I-795) was synthesized according to the process of Synthesis Example 3.

White solid, yield: 0.20 g, percent yield: 52%, m.p.: 135–138° C. IR KBr cm$^{-1}$: 3372, 1728, 1598, 1440, 1356, 1262, 1192. $^1$H-NMR (60 MHz, CDCl$_3$, δ): 3.80 (3H, s, OCH$_3$), 6.9 (1H, d, J=2 Hz, pyridine ring H), 7.28–7.65 (3H, m, aromatic ring H), 7.46 (1H, d, J=2 Hz, pyridine ring H), 8.2 (1H, dd, J=2 Hz, 8 Hz, aromatic ring H), NH indistinctness.

Synthesis Example 17
Synthesis of N-[(2-Trifluoromethoxyphenyl)sulfonyl]-6-chloro-5-methoxy-2-pyridinecarboxamide [Compound (I-798)]

Using 2-trifluoromethoxybenzenesulfonamide [Compound (III-12)] (0.3 g, 1.24 mmol) and 6-chloro-5-methoxypicolinic acid phenyl ester [Compound (IV-78)] (0.328 g, 1.24 mmol), the Compound (I-798) was synthesized according to the process of Synthesis Example 1.

White solid, yield: 0.408 g, percent yield: 80%, m.p.: 146–148° C. IR KBr cm$^{-1}$: 3292, 1713, 1572, 1446, 1386, 1362, 1281, 1065, 864. $^1$H-NMR (60 MHz, CDCl$_3$, δ): 3.9 (3H, s, OCH$_3$), 7.26–8.26 (4H, m, aromatic ring H), 4.16 (1H, d, J=8 Hz, pyridine ring H), 7.9 (1H, d, J=8 Hz, pyridine ring H), NH indistinctness.

Synthesis Example 18
Synthesis of N-[[2-(N,N-Dimethylaminosulfonyl)phenyl]sulfonyl]-6-chloro-5-methoxy-2-pyridinecarboxamide [Compound (I-888)]

Using 2-(N,N-dimethylaminosulfonyl)benzene sulfonamide [Compound (III-13)] (0.3 g, 1.138 mmol) and 6-chloro-5-methoxypicolinic acid phenyl ester [Compound (IV-78)] (0.3 g, 1.138 mmol), Compound (I-888) was synthesized according to the process of Synthesis Example 1.

White solid, yield: 0.44 g, percent yield: 88.7%, m.p.: 228° C. (decomposition). IR KBr cm$^{-1}$: 3358, 1725, 1440, 1416, 1278, 1161, 576. $^1$H-NMR (60 MHz, CDCl$_3$, δ): 2.86 [6H, s N(CH$_3$)$_2$], 3.85 (3H, s, OCH$_3$), 7.0–8.0 (5H, m, aromatic ring H×3, pyridine ring H×2), 8.2–8.7 (1H, m, aromatic ring H), 10.5 (1H, bs, NH).

Synthesis Example 19
Synthesis of N-[(2,6-Difluorophenyl)sulfonyl]-6-chloro-4-methoxy-2-pyridinecarboxamide [Compound (I-975)]

Using 2,6-difluorobenzenesulfonamide [Compound (III-14)] (0.309 g, 1.6 mmol) and 6-chloro-4-methoxypicolinic acid [Compound (II-75)] (0.3 g, 1.6 mmol), the Compound (I-975) was synthesized according to the process of Synthesis Example 3.

White solid, yield: 0.3129 g, percent yield: 54.0%, m.p.: 160–163° C. IR KBr cm$^{-1}$: 3262, 1725, 1620, 1434, 1398, 1317, 1188, 1029, 891, 642. $^1$H-NMR (60 MHz, CDCl$_{3,\ 6}$): 3.8 (3H, s, OCH$_3$), 6.7–7.5 (4H, m, aromatic H×3, pyridine ring H), 7.43 (1H, d, J=2 Hz, pyridine ring H), NH indistinctness.

Synthesis Example 20
Synthesis of 4,6-Dichloropicolinic Acid [Compound (II-17)]

(1) Synthesis of pyridonic acid

A mixture of chelidonic acid (25 g, 0.123 mol) and 40% aqueous solution of methylamine (500 ml) was stirred at room temperature for about 15 minutes, followed by stirring at 90–100° C. for 10 hours. The reaction mixture was then cooled and acidified with concentrated hydrochloric acid. The solid precipitate was collected by filtration, washed with water and dried.

White solid, yield: 13 g, percent yield: 53.3%, m.p.: 205° C. (decomposition). IR KBr cm$^{-1}$: 1737, 1638, 1485, 1275, 1131. $^1$H-NMR (60 MHz, CDCl$_3$, δ): 3.75 (3H, s, N—CH$_3$), 4.0 (2H, s, COOH×2), 6.7 (2H, s, pyridone ring H).

(2) Synthesis of 4,6-Dichloropicolinic Acid Methyl Ester [Compound (V-17)]

N-Methylpyridonic acid (13 g, 0.066 mol) was stirred in thionyl chloride (50 ml) containing a catalytic amount of N,N-dimethylformamide (35 mg) at 90° C. for 1.5 hours. Thereafter, thionyl chloride was completely removed by distillation. The reaction mixture was added into 100 ml of methanol under cooling with water. After being stirred for 2 hours, methanol was distilled off and the residue was distributed with ethyl acetate and water. The organic layer was washed with saturated saline solution and dried with sodium sulfate. After the solvent was distilled off, the product was purified by silica gel column chromatography to obtain 4,6-dichloropicolinic acid methyl ester.

White solid, yield: 3.63 g, percent yield: 26.6%, m.p.: 75–77° C. IR KBr cm$^{-1}$: 3100, 1728, 1395, 1296, 810. $^1$H-NMR (60 MHz, CDCl$_3$, δ): 3.9 (3H, s, COOCH$_3$), 7.4 (1H, d, J=2 Hz, pyridine ring H), 7.9 (1H, d, J=2 Hz, pyridine ring H).

(3) Synthesis of 4,6-Dichloropicolinic Acid [Compound (II-17)]

4,6-Dichloropicolinic acid methyl ester (0.5 g, 2.43 mmol) was stirred in a mixture of sodium hydroxide (0.11 g, 2.43×1.1 mmol), 1.1 ml of water and 11 ml of ethanol at 60° C. for 1 hour.

Ethanol in the reaction solution was distilled off and the residue was washed with dichloromethane. The aqueous layer was acidified with diluted hydrochloric acid. After being extracted with ethyl acetate, the product was washed with saturated saline solution and dried with sodium sulfate.

White solid, yield: 0.46 g, percent yield: 98.7%, m.p.: 114–116° C. IR KBr cm$^{-1}$: 3562, 1692, 1557, 1395, 1287, 819.

Synthesis Example 21
Synthesis of 4-Chloro-6-methoxypicolinic Acid [Compound (II-41)]

(1) Synthesis of 4-chloro-6-methoxypicolinic acid methyl ester [Compound (V-41)]

1 ml of methanol and sodium hydride (60% in mineral oil, 0.21 g, 4.85×1.1 mmol) were added to 20 ml of dry dioxane. After conclusion of bubbling, a solution of 4,6-dichloropicolinic acid methyl ester [Compound (V-17)] (1 g, 4.85 mmol) in 5 ml of dioxane was added dropwise thereto. Cuprous iodide (0.92 g, 4.85 mmol) was then added, and the mixture was stirred at 120° C. for 4 hours with heating. Thereafter, the mixture was filtered with a glass filter equipped with a high-flow super cell, and washed with methanol. The filtrate was concentrated and distributed with water and ethyl acetate. The organic layer was separated and dried with sodium sulfate. It was concentrated and purified by silica gel column chromatography to obtain 0.78 g of a white solid in a percent yield of 80%.

m.p.: 65–66° C. IR KBr cm$^{-1}$: 1758, 1731, 1593, 1461, 1398, 1269, 1149, 1047. $^1$H-NMR (60 MHz, CDCl$_3$, δ): 3.86 (3H, s, OCH$_3$ or COOCH$_3$), 3.93 (3H, s, OCH$_3$ or COOCH$_3$), 6.8 (1H, d, J=2 Hz, pyridine ring H), 7.55 (1H, d, J=2 Hz, pyridine ring H).

(2) Synthesis of 4-chloro-6-methoxypicolinic acid [Compound (II-41)]

Using 4-chloro-6-methoxypicolinic acid methyl ester [Compound (V-4)] (0.72 g, 3.57 mmol), the Compound (II-41) was synthesized according to the process of Synthesis Example 20 (3).

White solid, m.p.: 149° C., yield: 0.503 g, percent yield: 75.2%. IR KBr cm$^{-1}$: 1710, 1596, 1467, 1284. $^1$H-NMR (60 MHz, d$_6$-DMSO, δ): 3.85 (3H, s, OCH$_3$), 7.13 (1H, d, J=1 Hz, pyridine ring H), 7.5 (1H, d, J=1 Hz, pyridine ring H), COOH indistinctness.

Synthesis Example 22
Synthesis of 6-Chloro-4-methoxypicolinic Acid [Compound (II-75)]

(1) Synthesis of 6-chloropicoline-N-oxide

6–Chloropicoline (50 g, 0.392 mol) was dissolved in acetic acid (146 g, 0.392×2.5 mol). To the resultant solution was added 31% aqueous hydrogen peroxide (107 g, 0.392× 2.5 mol) and the mixture was stirred at 40–90° C. for 1 hour and at 100° C. for 32 hours. To the reaction solution was added 300 ml of water and then sodium carbonate so as to be weak alkaline. It was then extracted with ethyl acetate, washed with saturated saline solution and dried with sodium sulfate. After the solvent was distilled off, it was distilled by a glass tube oven to obtain a light yellow transparent liquid.

Yield: 26.2 g, percent yield: 46.5%. IR NaCl film cm$^{-1}$: 1482, 1377, 1161, 783. $^1$H-NMR (60 MHz, CDCl$_3$, δ): 2.58 (3H, s, CH$_3$), 7.28–7.63 (3H, m, pyridine ring H).

(2) Synthesis of 6-chloro-4-nitropicoline-N-oxide

98% Sulfuric acid (131 g, 0.207×6.3 mol) was added to 6-chloropicoline-N-oxide (29.7 g, 0.207 mol). To the resultant mixture was added 98% fuming sulfuric acid (72.34 g, 0.207×5 mol) and stirred at 100° C. for 1.5 hours. The reaction solution was then poured into iced water. A solid precipitate was filtered out, washed with water and dried to obtain 15.98 g of the target product. Furthermore, the filtrate was changed into weak alkalinity with sodium carbonate. A solid precipitate was filtered out, washed with water and dried to obtain 13.28 g of the target product. Percent yield: 75.0%, light yellow solid, m.p.: 118–121° C. IR KBr cm$^{-1}$: 1540, 1360, 1310, 1250, 920, 745. $^1$H-NMR (60 MHz, CDCl$_3$, δ): 2.56 (3H, s, CH$_3$), 8.0 (1H, d, J=3 Hz, pyridine ring H), 8.2 (1H, d, J=3 Hz, pyridine ring H).

(3) Synthesis of 6-chloro-4-methoxypicoline-N-oxide

6-Chloro-4-nitropicoline-N-oxide (5 g, 26.5 mmol) was dissolved in 100 ml of dry methanol. To the resultant solution was added sodium hydride (60% in mineral oil, 1.1 g, 26.5×1.05 mmol). The solution was then stirred at room temperature for 2 hours and additionally for 2.5 hours under stirring with heat. Methanol was then distilled off and the residue was distributed with water and chloroform. The organic layer was-washed with saturated saline solution and dried with sodium sulfate. The solvent was distilled off to obtain 4.5 g of the target product.

Percent yield: 98%, m.p.: 103–105° C. IR KBr cm$^{-1}$: 1632, 1557, 1482, 1251, 1206, 1185, 1050, 960. $^1$H-NMR (60 MHz, CDCl$_3$, δ): 2.5 (3H, s, CH$_3$), 3.76 (3H, s, OCH$_3$), 6.6 (1H, d, J=3 Hz, pyridine ring H), 6.8 (1H, d, J=3 Hz, pyridine ring H).

(4) Synthesis of 6-chloro-4-methoxy-2-acetoxymethylpyridine

6-Chloro-4-methoxypicoline-N-oxide (3.58 g, 20.6 mmol) was dissolved in 9.6 ml of acetic acid. To the solution, 21 ml of anhydrous acetic acid was added dropwise with heating to 120° C. Thereafter the mixture was stirred at 130° C. for 4 hours. Acetic acid and anhydrous acetic acid were distilled off under vacuum. The residue was distributed with water and ethyl acetate, and the organic layer was washed with saturated saline solution and dried with sodium sulfate. After the solvent was distilled off, the target product was purified by silica gel column chromatography.

White solid, Yield: 2.85 g, percent yield: 64.8%, m.p.: 64–65° C. IR KBr cm$^{-1}$: 3094, 1746, 1599, 1566, 1449, 1386, 1299, 1263, 1125, 852. $^1$H-NMR (60 MHz, CDCl$_3$, δ): 2.1 (3H, s, COCH$_3$), 3.8 (3H, s, OCH$_3$), 5.0 (2H, s, CH$_2$), 6.8 (2H, s, pyridine ring H).

(5) Synthesis of 6-chloro-4-methoxy-2-hydroxymethylpyridine

6-Chloro-4-methoxy-2-acetoxymethylpyridine (3.38 g, 15.7 mmol) was stirred in 23.5 ml of 10% hydrochloric acid at 80° C. for 1.5 hours. The reaction mixture was then cooled and neutralized with sodium carbonate. The product was extracted with chloroform, washed with saturated saline solution and dried with sodium sulfate.

White solid, yield: 2.52 g, percent yield: 92.6%, m.p.: 75–76° C. IR KBr cm$^{-1}$: 1599, 1566, 1437, 1413, 1296, 1119, 1044, 993, 852, 840. $^1$H-NMR (60 MHz, CDCl$_3$, δ): 3.5–4.0 (1H, bs, OH), 3.76 (3H, s, OCH$_3$), 4.58 (2H, s, CH$_2$), 6.6 (1H, d, J=2 Hz, pyridine ring H), 6.73 (1H, d, J=2 Hz, pyridine ring H).

(6) Synthesis of 6-chloro-4-methoxypicolinic acid [Compound (II-75)]

To a solution of 6-chloro-4-methoxy-2-hydroxymethylpyridine (2.43 g, 14 mmol) in 27.5 ml of benzene was added tetra-n-butylammonium bromide (0.175 g, 14×0.0388 mmol).

It was then cooled to 5–10° C., and 72.5 ml of an aqueous solution of potassium permanganate (2.95 g, 14×1.33 mmol) was added dropwise over 45 minutes. Thereafter, the mixture was stirred at 5–10° C. for 30 minutes. The reaction solution was filtered with a glass filter equipped with high-flow super cell and washed with hot water. The filtrate was acidified with hydrochloric acid and the solid precipitate was filtered out and washed with water.

White solid, yield: 1.24 g, percent yield: 47.4%, m.p.: 184–185° C. IR KBr cm$^{-1}$: 1707, 1599, 1473, 1320, 1284, 1107, 1038, 921, 870, 723. $^1$H-NMR (60 MHz, d$_6$-DMSO+CDCl$_3$, δ): 3.85 (3H, s, OCH$_3$), 6.95 (1H, d, J=2 Hz, pyridine ring H), 7.46 (1H, d, J=2 Hz, pyridine ring H), COOH indistinctness.

Synthesis Example 23

Synthesis of 6-Chloro-4-methoxypicolinic Acid [Compound (II-75)]

(1) Synthesis of 6-chloro-4-methoxypicolinic Acid Methyl Ester [Compound (V-75)], 4,6-Dichloropicolinic acid methyl ester [Compound (V-17)] (0.42 g, 2.04 mmol) and 0.5 ml of dry methanol were dissolved in 10 ml of dry N,N-dimethylacetamide. To the resultant solution was added sodium hydride (60% in mineral oil, 0.086 g, 2.04×1.05 mmol) and stirred at 80° C. for 2 hours. The reaction solution was distributed by adding diluted hydrochloric acid and ethyl acetate. After the organic layer was separated and washed with saturated saline solution, the solvent was removed by concentration. The product was purified by silica gel column chromatography.

White solid, yield: 0.26 g, percent yield: 64.3%, m.p.: 92–93° C. IR KBr cm$^{-1}$: 1728, 1602, 1446, 1320, 1101, 1038. $^1$H-NMR (60 MHz, CDCl$_3$, δ): 3.8 (3H, s, COOCH$_3$ or OCH$_3$), 3.9 (3H, s, COOCH$_3$ or OCH$_3$), 6.9 (1H, d, J=2 Hz, pyridine ring H), 7.5 (1H, d, J=2 Hz, pyridine ring H).

(2) Synthesis of 6-chloro-4-methoxypicolinic Acid [Compound (II-75)]

Using 6-chloro-4-methoxypicolinic acid methyl ester [Compound (V-75)] (0.5 g, 2.48 mmol), the Compound (II-75) was synthesized according to the process of Synthesis Example 20 (3).

White solid, yield: 0.45 g, percent yield: 97.0%, m.p.: 183–185° C. IR KBr cm$^{-1}$: 1707, 1599, 1473, 1320, 1284, 1107, 1038, 921, 870, 723. $^1$H-NMR (60 MHz, d$_6$-DMSO, δ): 3.84 (3H, s, OCH$_3$), 6.94 (1H, d, J=2 Hz, pyridine ring H), 7.45 (1H, d, J=2 Hz, pyridine ring H), COOH indistinctness.

Synthesis Example 24

Synthesis of 4,6-Dimethoxypicolinic Acid [Compound (II-77)]

(1) Synthesis of 4,6-dimethoxypicolinic Acid Methyl Ester [Compound (V-77)]

To a solution obtained by dissolving 4,6-dichloropicolinic acid methyl ester [Compound (V-17)] (1.0 g, 4.85 mmol) and 2 ml of dry methanol in 20 ml of dry N,N-dimethylacetamide was added sodium hydride (60% in mineral oil, 0.4 g, 4.85×2.05 mmol) and stirred at 80° C. for 4 hours. The reaction solution was then distributed by adding diluted hydrochloric acid and ethyl acetate. After the organic layer was separated and washed with saturated saline solution, the solvent was removed by concentration. The product was purified by silica gel column chromatography.

White solid, yield: 0.15 g, percent yield: 16%, m.p.: 105° C. IR KBr cm$^{-1}$: 1716, 1617, 1464, 1365, 1293, 1257, 1221, 1119, 1038. $^1$H-NMR (60 MHz, CDCl$_3$, δ): 3.76 (3H, s, OCH$_3$), 3.86 (3H, s, OCH$_3$), 3.9 (3H, s, COOCH$_3$), 6.2 (1H, d, J=2 Hz, pyridine ring H), 7.2 (1H, d, J=2 Hz, pyridine ring H).

(2) Synthesis of 4,6-dimethoxypicolinic acid [Compound (II-77)]

Using 4,6-dimethoxypicolinic acid methyl ester [Compound (V-77)] (0.148 g, 0.75 mmol), the Compound (II-77) was synthesized according to the process of Synthesis Example 20 (3).

White solid, m.p.: 145–148° C., yield: 0.0966 g, percent yield: 70.5%. IR KBr cm$^{-1}$: 1701, 1620, 1473, 1296, 1218. $^1$H-NMR (60 MHz, d$_6$-DMSO, δ): 3.75 (3H, OCH$_3$), 3.80 (3H, s, OCH$_3$), 6.4 (1H, d, J=2 Hz, pyridine ring H), 7.1 (1H, d, J=2 Hz, pyridine ring H), COOH indistinctness.

Synthesis Example 25

Synthesis of 6-Chloro-5-methoxypicolinic Acid Phenyl Ester [Compound (IV-78)]

(1) Synthesis of 6-chloro-5-hydroxypicoline

To a solution obtained by dissolving 5-hydroxypicoline (10 g, 91.6 mmol) in pyridine (30 ml) was added N-chlorosuccinimide (12.2 g, 91.6 mmol). The mixture was stirred at room temperature for 4 hours. Pyridine was then distilled off by an evaporator and water was added to the residue. The precipitate was filtered out and washed water to obtain a white solid.

Yield: 4.59 g, percent yield: 34.7%, m.p.: 190–192° C. IR KBr cm$^{-1}$: 2872, 2782, 2692, 2590, 1563, 1500, 1296, 1227, 1095, 831. $^1$H-NMR (60 MHz, CDCl$_3$+d$_6$-DMSO, δ): 2.35 (3H, s, CH$_3$), 6.8 (1H, d, J=8 Hz, pyridine ring H), 7.08 (1H, d, J=8 Hz, pyridine ring H), 9.16–9.35 (1H, bs, OH).

(2) Synthesis of 6-chloro-5-methoxypicoline

To a solution obtained by dissolving 6-chloro-5-hydroxypicoline (5.1 g, 35.4 mmol) in 40 ml of acetone was added solid sodium carbonate (6.62 g, 35.4×1.5 mmol). Methyl iodide (9.07 g, 35.4×2.0 mmol) was then added dropwise to the mixture with stirring at 50° C., followed by stirring for 5 hours. Acetone was then distilled off and the residue was purified by silica gel column chromatography to obtain the target product as a white solid.

Yield: 4.53 g, percent yield: 81.3%, m.p.: 43–45° C. IR KBr cm$^{-1}$: 1572, 1473, 1302, 1101, 1020, 825, 747. $^1$H-NMR (60 MHz, CDCl$_3$, δ): 2.4 (3H, s, CH$_3$), 3.8 (3H, s, OCH$_3$), 6.9 (1H, d, J=8 Hz, pyridine ring H), 7.05 (1H, d, J=8 Hz, pyridine ring H).

(3) Synthesis of 6-chloro-5-methoxypicolinic acid [Compound (II-78)]

6-Chloro-5-methoxypicoline (4.53 g, 28.76 mmol) was mixed with 20 ml of water, followed by stirring at 50–60° C. To the resultant mixture was added potassium permanganate (4.77 g, 28.76×1.05 mmol) and stirred for an hour. Potassium permanganate (4.77 g, 28.76×1.05 mmol) was additionally added, and the mixture was stirred at the same temperature for 2 hours. The reaction solution was stirred for 30 minutes after addition of methanol and filtered with a glass filter equipped with a high-flow super cell. The residue was washed with warm water and the filtrate was acidified with diluted hydrochloride. The solid precipitate was filtered out, washed with water and dried to obtain a white solid.

Yield: 2.26 g, percent yield: 42.1%, m.p.: 229° C. (decomposition). IR KBr cm$^{-1}$: 1698, 1575, 1422, 1344, 1269, 1092, 999, 852. $^1$H-NMR (60 MHz, CDCl$_3$, δ): 3.87 (3H, s, OCH$_3$), 7.5 (1H, d, J=8 Hz, pyridine ring H), 7.9 (1H, d, J=8 Hz, pyridine ring H), COOH indistinctness.

(4) Synthesis of 6-chloro-5-methoxypicolinic acid phenyl ester [Compound (IV-78)]

A mixture of 6-chloro-5-methoxypicolinic acid (1.5 g, 8.0 mmol), thionyl chloride (5 g, 8.0×5.25 mmol), a catalytic amount (35 mg) of N,N-dimethylformamide and 5 ml of benzene was refluxed for 1 hour. Then, thionyl chloride and benzene were distilled off, and the residue was distributed with water and dichloromethane. A dichloromethane layer was separated and dried with sodium sulfate. The solvent was then distilled off to obtain 1.64 g of 6-chloro-5-methoxypicolinic acid chloride. It was dissolved again in 5 ml of dichloromethane and the resultant solution was added dropwise to a solution of phenol (0.79 g, 8×1.05 mmol) and triethyl amine (0.89 g, 8×1.1 mmol) in 30 ml of dichloromethane under cooling with ice. After conclusion of the addition, the reaction solution was stirred at room temperature for 2 hours, followed by adding water to separate an organic layer. The organic layer was washed with a saturated aqueous solution of sodium hydrogen carbonate and dried with sodium sulfate. The organic solvent was distilled off to obtain a white solid.

Yield: 2.06 g, percent yield: 98%, m.p.: 141–143° C. IR KBr cm$^{-1}$: 1755, 1566, 1395, 1254, 1194, 1089, 999, 708. $^1$H-NMR (60 MHz, CDCl$_3$, δ): 3.9 (3H, s, OCH$_3$), 7.16 (1H, d, J=8 Hz, pyridine ring H), 6.95–7.35 (5H, m, aromatic ring H), 8.05 (1H, d, J=8 Hz, pyridine ring H).

Synthesis Example 26
Synthesis of 2,6-Dichlorobenzenesulfonamide [Compound (III-7)]

To a solution obtained by dissolving 29% aqueous ammonia (6.9 g, 20.36×5 mmol) in 40 ml of acetonitrile was added dropwise a solution of 2,6-dichlorobenzenesulfonyl chloride [Compound (XXII-7)] (5 g, 20.36 mmol) in 10 ml of acetonitrile under cooling with water. Thereafter, the reaction solution was stirred at room temperature for 3 hours and distilled off. Water was added to the residue, followed by filtration to obtain an insoluble material, which was washed with water and then with a small amount of acetonitrile.

White solid, m.p.; 173–5° C., yield: 4.3 g, percent yield: 94%. IR KBr cm$^{-1}$: 3382, 3268, 1575, 1428, 1338, 1143, 780. $^1$H-NMR (60 MHz, d$_6$-DMSO, δ): 7.4–7.6 (3H, aromatic ring H), 7.6–7.9 (2H, bs NH$_2$).

Synthesis Example 27
Synthesis of 2-Trifluoromethylbenzenesulfonamide [Compound (III-1)]

Using 2-trifluoromethylbenzenesulfonyl chloride [Compound (XXII-1)] (5 g, 0.0204 mol), the Compound (III-1) was synthesized according to the process of Synthesis Example 26.

White solid, m.p.: 186–187° C., yield: 4.4 g, percent yield: 95.6%. IR KBr cm$^{-1}$: 3394, 3274, 1347, 1161, 1140. $^1$H-NMR (60 MHz, d$_6$-DMSO, δ): 7.4–7.9 (5H, m, aromatic ring H×3, NH$_2$), 7.9–8.4 (1H, m, aromatic ring H).

Synthesis Example 28
Synthesis of 2,3-Dichlorobenzenesulfonamide [Compound (III-4)]

Using 2,3-dichlorobenzenesulfonyl chloride [Compound (XXII-4)] (5 g, 0.0203 mol), the Compound (III-4) was synthesized according to the process of Synthesis Example 26.

White solid, m.p.: 217–219° C., yield: 4.37 g, percent yield: 95%. IR KBr cm$^{-1}$: 3388, 3268, 1344, 1170, 1146, 1095, 606. $^1$H-NMR (60 MHz, d$_6$-DMSO, δ): 7.2–7.96 (5H, m, aromatic ring H×3, NH$_2$).

Synthesis Example 29
Synthesis of 2,5-Dichlorobenzenesulfonamide [Compound (III-6)]

Using 2,5-dichlorobenzenesulfonyl chloride [Compound (XXII-6)] (5 g, 0.02036 mol), the Compound (III-6) was synthesized according to the process of Synthesis Example 26.

White solid, m.p.: 177–178° C., yield: 4.27 g, percent yield: 93%. IR KBr cm$^{-1}$: 3280, 3094, 1455, 1344, 1164, 1044, 828, 600. $^1$H-NMR (60 MHz, d$_6$-DMSO, δ): 7.36–7.7 (4H, m, aromatic ring H×2, NH$_2$), 7.8–7.9 (1H, m, aromatic ring H).

Synthesis Example 30
Synthesis of 2-Chlorobenzenesulfonamide [Compound (III-11)]

Using 2-chlorobenzenesulfonyl chloride [Compound (XXII-11)] (5 g, 0.0237 mol), the Compound (III-11) was synthesized according to the process of Synthesis Example 26.

White solid, m.p.: 185–7° C., yield: 4.42 g, percent yield: 97.5%. IR KBr cm$^{-1}$: 3268, 3106, 1563, 1344, 1161, 1044, 768, 672. $^1$H-NMR (60 MHz, d$_6$-DMSO, δ): 7.3–7.7 (5H, m, aromatic ring H×3, NH$_2$), 7.7–8.06 (1H, m, aromatic ring H).

Synthesis Example 31
Synthesis of 2-(N,N-Dimethylaminosulfonyl)benzene Sulfonamide [Compound (III-13)]

(1) Synthesis of 2-(N,N-dimethylaminosulfonyl) nitrobenzene

N,N-Dimethylamine hydrochloride (5.5 g, 45.1×1.5 mmol) was suspended in 50 ml of acetonitrile. To the resultant suspension was added triethylamine (11.86 g, 45.1×2.6 mmol) under cooling with ice, followed by adding dropwise a solution of 2-nitrobenzenesulfonnyl chloride (10 g, 45.1 mmol) in 50 ml of acetonitrile. Thereafter, the mixture was stirred at room temperature for 3 hours. The reaction solution was then concentrated and the residue was distributed with ethyl acetate and diluted hydrochloric acid. An organic layer was separated, washed with water and dried with sodium sulfate (anhydrous). The solvent was then distilled off to obtain a solid, which was washed with a small amount of ethyl acetate and filtered out.

Light yellow solid, m.p.: 77–78° C., yield: 7.8 g, percent yield: 75.4%. IR KBr cm$^{-1}$: 1542, 1374, 1338, 1164, 1146, 975. $^1$H-NMR (60 MHz, CDCl$_3$, δ): 2.83 (6H, s, CH$_3$×2), 7.4–8.0 (4H, m, aromatic ring H).

(2) Synthesis of 2-(N,N-dimethylaminosulfonyl)aniline 2-(N,N-Dimethylaminosulfonyl)nitrobenzene (8 g, 34.78 mmol) was dissolved in 27 ml of toluene, followed by adding 11 ml of water. To the resultant solution was added reduced iron (5.7 g, 34.78×2.93 mmol) and then was added 0.56 ml of acetic acid with vigorously stirring in an oil bath at 100–110° C. After refluxed vigorously for 1.5 hours, the reaction solution was cooled and changed into weak alkalinity with sodium carbonate, followed by filtration with a glass filter equipped with a high-flow cell. The toluene layer was separated from the filtrate and washed with water, dried with sodium sulfate (anhydrous) and concentrated to obtain a white solid.

m.p.: 86° C., yield: 5.89 g, percent yield: 84.7%. IR KBr cm$^{-1}$: 3514, 3412, 1629, 1326, 1140, 951, 738, 714. $^1$H-NMR (60 MHz, CDCl$_3$, δ): 2.68 (6H, s, CH$_3$×2), 4.6–5.25 (2H, bs, NH$_2$), 6.43–6.76 (2H, m, aromatic ring H), 7.0–7.58 (2H, m, aromatic ring H).

(3) Synthesis of 2-(N,N-dimethylaminosulfonyl)benzene Sulfonamide [Compound (III-13)]

To a solution obtained by dissolving 2-(N,N-dimethylaminosulfonyl)aniline [Compound (XXV-13)] (5.12 g, 25.6 mmol) in 2.7 ml of acetic acid was added 35% hydrochloric acid (8.96 ml, 25.6×3.35 mmol) under cooling with ice. A solution of sodium nitrite (2.11 g, 25.6×1.2 mmol) in 4.1 ml of water (diazonium solution) was added dropwise over about 15 minutes at 0–5° C.

On the other hand, sodium hydrogen sulfite (7.46 g, 25.6×2.8 mmol) was suspended in 33.6 ml of acetic acid under cooling with ice, followed by adding dropwise 35% hydrochloric acid (7.26 ml, 25.6×2.72 mmol) little by little. Thereafter, a cuprous chloride powder (0.508 g, 25.6×0.2 mmol) was added at a time thereto and then the diazonium solution previously prepared was added dropwise over 15 minutes. The mixture was stirred for about 2 hours with slowly elevating the temperature to room temperature. The reaction solution was poured into iced-water and extracted with dichloromethane. The organic layer was separated and concentrated to obtain 6.2 g (percent yield: 85.4%) of the intermediate: 2-(N,N-dimethylaminosulfonyl)-phenylsulfonyl chloride.

A solution obtained by dissolving 5 g (17.6 mmol) of it in 10 ml of acetonitrile was added dropwise to a solution consisting of 29% aqueous ammonia (10.6 g, 17.6×5 mmol) and 10 ml of acetonitrile under cooling with water. After stirred about 3 hours, it was concentrated to remove acetonitrile and the residue was filtered out, washed with water and dried to obtain the target compound.

White solid, m.p.: 145–146° C., yield: 3.74 g, percent yield: 80.5%. IR KBr cm$^{-1}$: 3430, 3322, 1359, 1323, 1161, 963, 789. $^1$H-NMR (60 MHz, CDCl$_3$+d$_6$-DMSO, δ): 2.86 (6H, s, N—CH$_3$×2), 6.56–6.81 (2H, bs, NH$_2$), 7.38–7.96 (3H, m, aromatic ring H), 8.1–8.3 (1H, m, aromatic ring H).

Synthesis Example 32

Synthesis of 2-Trifluoromethoxybenzenesulfonamide [Compound (III-12)]

Using 2-trifluoromethoxyaniline [Compound (XXV-12)] (5 g, 0.0282 mmol), 7.3 g (percent yield: 99.4%) of 2-trifluoromethoxybenzenesulfonyl chloride [Compound (XXII-12)] was synthesized according to the process of Synthesis Example 31 (3). Thereafter, the compound (III-12) was synthesized using 3.9 g (0.0149 mol) of the Compound (XXII-12) according to Synthesis Example 31 (3).

White solid, m.p.: 183–184° C., yield: 2.09 g, percent yield: 46.2%. IR KBr cm$^{-1}$: 3382, 3268, 1482, 1344, 1230, 1164, 768. $^1$H-NMR (60 MHz, d$_6$-DMSO, δ): 7.2–7.65 (5H, m, aromatic ring H×3, NH$_2$), 7.86 (1H, dd, J=2Hx, 8 Hz, aromatic ring H).

Synthesis Example 33

Synthesis of 2,6-Difluorobenzenesulfonamide [Compound (III-14)]

Using 2,6-difluoroaniline [Compound (XXV-14)] (5 g, 0.0387 mol), 8.2 g (percent yield: theoretic) of 2,6-difluorobenzenesulfonyl chloride [Compound (XXII-14)] was synthesized according to the process of Synthesis Example 31 (3). Thereafter, the Compound (III-14) was synthesized using 8.2 g (0.0387 mol) of the Compound (XXII-14) according to Synthesis Example 31 (3).

White solid, m.p.: 184–5° C., yield: 2.79 g, percent yield: 37.4%. IR KBr cm$^{-1}$: 3370, 3262, 1620, 1593, 1473, 1356, 1170, 789. $^1$H-NMR (60 MHz, d$_6$-DMSO, δ): 6.9–7.7 (3H, m, aromatic ring H), 7.7–7.9 (2H, bs, NH$_2$).

Synthesis Example 34

Synthesis of 6-Bromo-5-methoxy-2-pyridinecarboxylic Acid [Compound (II-85)]

(1) Synthesis of 6-bromo-5-hydroxy-2-methylpyridine [R$^4$=Br in Compound (XIV)]

To a solution obtained by dissolving 5-hydroxypicoline (10 g, 0.0916 mol) in pyridine (30 ml) was added dropwise bromine (15.4 g, 0.0916×1.05 mol), followed by stirring at room temperature for 4 hours. Pyridine was then distilled off by an evaporator. To the residue was added water and the precipitate was filtered out, washed with water to obtain a white solid.

Yield: 5.38 g, percent yield: 31.3%, m.p.: 185–187° C. IR KBr cm$^{-1}$: 2776, 1563, 1296, 1221, 1083, 831. $^1$H-NMR (60 MHz, d$_6$-DMSO, δ): 2.26 (3H, s, CH$_3$), 6.93 (1H, d, J=8 Hz, pyridine ring H), 7.1 (1H, d, J=8 Hz, pyridine ring H), 10.2 (1H, s OH).

(2) Synthesis of 6-bromo-5-methoxy-2-methylpyridine [R$^4$=Br, R$^5$=CH$_3$ in Compound (XIII)]

Using 6-bromo-5-hydroxy-2-methylpyridine [R$^4$=Br in Compound (XIV)] (5.18 g, 27.5 mmol), 6-bromo-5-methoxy-2-methyl-pyridine [R$^4$=Br, R$^5$=CH$_3$ in Compound (XIII)] was synthesized according to the process of Synthesis Example 25 (2).

White solid, m.p.: 49–50° C., yield: 5.4 g, percent yield: 98.2%. IR KBr cm$^{-1}$: 1563, 1470, 1371, 1296, 1080, 828. $^1$H-NMR (60 MHz, CDCl$_3$, δ): 2.4 (3H, s, CH$_3$), 3.8 (3H, s, CH$_3$), 6.93 (2H, s, pyridine ring H).

(3) Synthesis of 6-bromo-5-methoxy-2-pyridinecarboxylic Acid [Compound (II-85)]

6-Bromo-5-methoxy-2-methylpyridine [R$^4$=Br, R$^5$=CH$_3$ in Compound (XIII)] (2.7 g, 13.36 mmol) was mixed with 9.3 ml of water, and the bath temperature was controlled to 50–60° C. To the resultant mixture was added potassium permanganate (2.22 g, 13.36×1.05 mmol) and stirred for 1 hour. Thereafter, potassium permanganate (2.22 g, 13.36× 1.05 mmol) was additionally added and the mixture was stirred at the same temperature for 2 hours. After addition of 5 ml of methanol, the reaction solution was stirred at room temperature for 30 minutes. It was then filtered with a glass filter equipped with a high-flow super cell. To the filtrate was added 3 ml of concentrated hydrochloric acid to change into weak acidity. The solid precipitate was filtered out and dried.

White solid, m.p.: 227° C. (decomposition), yield: 1.1 g, percent yield: 35%. IR KBr cm$^{-1}$: 3200, 2600, 1098, 1566, 1419, 1341, 1269, 1077, 999. $^1$H-NMR (60 MHz, d$_6$-DMSO, δ): 3.9 (3H, s, OCH$_3$), 3.2–5.3 (1H, br, COOH), 7.5 (1H, d, J=8 Hz, pyridine ring H), 8.0 (1H, d, J=8 Hz, pyridine ring H).

Synthesis Example 35
Synthesis of 5-Methoxy-6-nitro-2-pyridinecarboxylic Acid [$R^4$=$NO_2$, $R^5$=$CH_3$ in Compound (XII)]

(1) Synthesis of 2-methyl-5-methoxy-6-nitropyridine [$R^4$=$NO_2$, $R^5$=$CH_3$ in Compound (XIII)]

Using 6-nitro-5-hydroxy-2-methylpyridine [$R^4$=$NO_2$ in Compound (XIV)] (5 g, 32.4 mmol), the above-mentioned compound was synthesized according to the process of Synthesis Example 25 (2).

White solid, m.p.: 86–87° C., yield: 4.83 g, percent yield: 89%. IR KBr cm$^{-1}$: 2932, 1545, 1494, 1386, 1311, 1122, 831. $^1$H-NMR (60 MHz, CDCl$_3$, δ): 2.5 (3H, s, CH$_3$), 3.8 (3H, s, OCH$_3$), 7.28 (2H, s, pyridine ring H).

(2) Synthesis of 5-methoxy-6-nitro-2-pyridinecarboxylic Acid [$R^4$=$NO_2$, $R^5$=$CH_3$ in Compound (XII)]

Using 2-methyl-5-methoxy-6-nitropyridine [$R^4$=$NO_2$, $R^5$=$CH_3$ in Compound (XIII)] (2 g, 11.89 mmol), the above-mentioned compound was synthesized according to the process of Synthesis Example 25 (3).

White solid, m.p.: 178–179° C. decomposition, yield: 0.27 g, percent yield: 12.3%. IR KBr cm$^{-1}$: 3100–2600 (br), 1713, 1599, 1338, 1302, 1275, 1116, 996. $^1$H-NMR (60 MHz, d$_6$-DMSO, δ): 4.0 (3H, s, OCH$_3$), 7.9 (1H, d, J=8 Hz, pyridine ring H), 8.3 (1H, d, J=8 Hz, pyridine ring H).

Synthesis Example 36
Synthesis of N-[[2-(N,N-Dimethylaminosulfonyl)phenyl]-sulfonyl]-5-methoxy-6-nitro-2-pyridinecarboxamide [Compound (I-858)]

Using 2-(N,N-dimethylaminosulfonyl)benzenesulfonamide [Compound (III-13)] (0.34 g, 1.29 mmol) and 6-nitro-5-methoxy-2-pyridine carboxylic acid (0.254 g, 1.29 mmol), the Compound (I-858) was synthesized according to the process of Synthesis Exampl 3.

White solid, m.p.: 190–192° C., yield: 0.288 g, percent yield: 50.5%. IR KBr cm$^{-1}$: 3328, 1734, 1605, 1407, 1362, 1191, 1164, 567. $^1$H-NMR (60 MHz, CDCl$_3$, δ): 2.9 [6H, s, N(CH$_3$)$_2$], 3.96 (3H, s, OCH$_3$), 7.53–8.66 (4H, m, aromatic ring H), 7.53 (1H, d, J=8 Hz, pyridine ring H), 8.2 (1H, d, J=8 Hz, pyridine ring H), NH indistinctness.

Synthesis Example 37
Synthesis of N-[(2-(Trifluoromethoxyphenyl)sulfonyl)-5-methoxy-6-nitro-2-pyridinecarboxamide [Compound (I-778)]

Using 2-trifluoromethoxyphenylsulfonamide [Compound (III-12)] (0.352 g, 1.46 mmol) and 6-nitro-5-methoxy-2-pyridinecarboxylic acid (0.289 g, 1.46 mmol), the Compound (I-778) was synthesized according to the process of Synthesis Example 1.

White solid, m.p.: 168–170° C., yield: 0.0904 g, percent yield: 14.8%. IR KBr cm$^{-1}$: 3260, 1730, 1620, 1565, 1445, 1310, 1270, 1200. $^1$H-NMR (60 MHz, CDCl$_3$, δ): 4.0 (3H, s, OCH$_3$), 7.26–7.80 (3H, m, aromatic ring H), 7.45 (1H, d, J=8 Hz, pyridine ring H), 8.0–8.3 (1H, m, aromatic ring H), 8.2 (1H, d, J=8 Hz, pyridine ring H), NH indistinctness.

Synthesis Example 38
Synthesis of N-[[2-(N,N-Dimethylaminosulfonyl)phenyl]-sulfonyl]-6-bromo-5-methoxy-2-pyridinecarboxamide [Compound (I-895)]

Using 2-(N,N-dimethylaminosulfonyl)benzenesulfonamide [Compound (III-13)] (0.34 g, 1.29 mmol) and 6-bromo-5-methoxy-2-pyridinecarboxlic acid [Compound (II-85)] (0.3 g, 1.29 mmol), the compound (I-895) was synthesized according to the process of Synthesis Example 3.

White solid, m.p.: 215–218° C., yield: 0.41 g, percent yield: 66.3%. IR KBr cm$^{-1}$: 3352, 1725, 1632, 1569, 1437, 1410, 1356, 1176, 1068. $^1$H-NMR (60 MHz, d$_6$-DMSO, δ): 2.81 [6H, s, N(CH$_3$)$_2$], 3.96 (3H, s, OCH$_3$), 7.56 (1H, d, J=8 Hz, pyridine ring H), 7.76–8.0 (3H, m, aromatic ring H), 7.9 (1H, d, J=8 Hz, pyridine ring H), 8.10–8.46 (1H, m, aromatic ring H), NH indistinctness.

Synthesis Example 39
Synthesis of N-[[2-Trifluoromethoxyphenyl]sulfonyl]-6-bromo-5-methoxy-2-pyridinecarboxamide [Compound (I-805)]

Using 2-trifluoromethoxyphenylsulfonamide [Compound (III-12)] (0.31 g, 1.29 mmol) and 6-bromo-5-methoxy-2-pyridine carboxylic acid [Compound (II-85)] (0.3 g, 1.29 mmol), the compound (I-805) was synthesized according to the process of Synthesis Example 3.

White solid, m.p.: 143–145° C., yield: 0.211 g, percent yield: 36.0%. IR KBr cm$^{-1}$: 3298, 1716, 1569, 1410, 1362, 1281, 1254, 1179. $^1$H-NMR (60 MHz, CDCl$_3$, δ): 3.9 (1H, s, OCH$_3$), 7.13 (1H, d, J=8 Hz, pyridine ring H), 7.2–7.7 (3H, m, aromatic ring H), 7.9 (1H, d, J=8 Hz, pyridine ring H), 8.0–8.3 (1H, m, aromatic ring H), 9.8–10.3 (1H, br, NH).

Synthesis Example 40
Synthesis of 2-[[[(6-Bromo-5-methoxypyridin-2-yl)carbonyl]-amino]sulfonyl]benzoic acid methyl ester [Compound (1–265)]

Using 2-(aminosulfonyl)benzoic acid methyl ester [Compound (III-3)] (0.278 g, 1.29 mmol) and 6-bromo-5-methoxy-2-pyridine-carboxlic acid [Compound (II-85)], the Compound (I-265) was synthesized according to the process of Synthesis Example 3.

White solid, m.p.: 178–179° C., yield: 0.36 g, percent yield: 66.0%. IR KBr cm$^{-1}$: 3358, 1725, 1569, 1404, 1359, 1275, 1185, 1074, 594. $^1$H-NMR (60 MHz, CDCl$_3$, δ): 3.9 (3H, s, COOCH$_3$ or OCH$_3$), 4.0 (3H, s, COOCH$_3$ or OCH$_3$), 7.15 (1H, d, J=8 Hz, pyridine ring H), 7.38–7.75 (3H, m, aromatic ring H), 8.0 (1H, d, J=8 Hz, pyridine ring H), 8.06–8.46 (1H, m, aromatic ring H) NH indistinctness.

Synthesis Example 41
Synthesis of 6-Cyano-4-methoxy-2-picoline [$R^7$=$OCH_3$ in Compound (XVIII)]

(1) Synthesis of 4-nitro-2-picoline-N-oxide

To picoline-N-oxide (20 g, 0.183 mol) were added 95% sulfuric acid (115.8 g, 0.183×6.1 mol) and 97% fuming nitric acid (63.9 g, 0.183×5.37 mol), followed by stirring at 100° C. for 1.5 hours. The reaction solution was then poured into 500 ml of iced-water and extracted with chloroform (100 ml×3 times). After dried with sodium sulfate (anhydrous), chloroform was distilled off to obtain 17.2 g of the target product. In addition, 200 g of sodium carbonate was added to the aqueous layer to change into weak alkalinity, which was then extracted by the same manner as described above to obtain 8.2 g of the target product.

Light yellow solid, m.p.: 152–3° C., yield: 25.4 g, percent yield: 90.1%. IR KBr cm$^{-1}$: 3130, 3052, 1617, 1518, 1464, 1344, 1290, 1272, 1236, 1092. $^1$H-NMR (60 MHz, CDCl$_3$, δ): 2.5 (3H, s, CH$_3$), 7.76–8.1 (2H, m, pyridine ring H×2), 8.23 (1H, d, J=7 Hz, pyridine ring H).

(2) Synthesis of 6-cyano-4-nitro-2-picoline [$R^7$=$NO_2$ in Compound (XVIII)]

A mixture of 4-nitro-2-picoline-N-oxide (11 g, 71,36 mmol) and dimethyl sulfate (10.8 g, 71.36×1.19 mmol) was heated to 65–70° C. with stirring for 2 hours. It was then cooled to solidify picoline salt, which was broken into pieces, filtered out and washed with 30 ml of n-hexane. It was dissolved in 27 ml of water and charged into a reaction flask. Then sodium cyanide (7.7 g, 71.36×2.2 mmol) was dissolved in 55 ml of water. The resultant solution was added dropwise to the above mixture at −7—−8° C. in a nitrogen atmosphere with vigorously stirring by means of a motor equipped with a agitation rod. The addition required 50 minutes. The mixture was then stirred for 3 hours at the same temperature and charged into a mixture of ethyl acetate: 200 ml/water: 100 ml. After the mixture was stirred for about 1 hour, it was allowed to stand for a night. The organic layer was separated, washed with water and dried with sodium sulfate (anhydrous). After the solvent was distilled off, the product was purified by silica gel column chromatography.

Yellow solid, m.p.: 74–6° C., yield: 8.36 g, percent yield: 72%. IR KBr cm$^{-1}$: 3100, 2236, 1584, 1551, 1362, 882, 765, 744. $^1$H-NMR (60 MHz, CDCl$_3$, δ): 2.76 (3H, s, CH$_3$), 8.0 (1H, d, J=2 Hz, pyridine ring H), 8.14 (1H, d, J=2 Hz, pyridine ring H).

(3) Synthesis of 6-cyano-4-methoxy-2-picoline [R$^7$=OCH$_3$ in Compound (XVIII)]

To 20 ml of dry tetrahydrofuran were added dry methanol (0.41 g, 13.12 mmol) and sodium hydride (60% mineral oil, 0.52 g, 13.12 mmol) under cooling with ice. After conclusion of bubbling, a solution of 6-cyano-4-nitro-2-picoline (2.14 g, 13.12 mmol) in 20 ml of dry tetrahydrofuran was added dropwise at room temperature. After stirring for 3 hours at room temperature, methanol was distilled off and the residue was distributed with ethyl acetate: 100 ml/water: 50 ml. The organic layer was separated, washed with water and dried with sodium sulfate (anhydrous). The product was purified by silica gel column chromatography.

White solid, m.p.: 105–6° C., yield: 1.65 g, percent yield: 85.2%. IR KBr cm$^{-1}$: 2236, 1602, 1473, 1344, 1212, 1056, 861. $^1$H-NMR (60 MHz, CDCl$_3$, δ): 2.5 (3H, s, CH$_3$), 3.8 (3H, s, OCH$_3$), 6.75 (1H, d, J=2 Hz, pyridine ring H), 7.0 (1H, d, J=2 Hz, pyridine ring H).

(4) Synthesis of 4-methoxy-6-methyl-2-pyridinecarboxylic Acid [R$^7$=OCH$_3$ in Compound (XVII)]

6-Cyano-4-methoxy-2-picoline [R$^7$=OCH$_3$ in Compound (XVIII)] (3.8 g, 25.67 mmol) was heated in 90% sulfuric acid (100 g, 25.67×35.1 mmol) to 120° C. for 2 hours with stirring. Thereafter, 100 ml of water and 90 g of sodium carbonate were added to the reaction solution so as to be pH 4–5. It was extracted 4 times with 100 ml of ethyl acetate. It was washed with saturated saline solution and dried with sodium sulfate.

Light yellow solid, m.p.: 170–2° C., yield: 1.8 g, percent yield: 41.7%. IR KBr cm$^{-1}$: 1680, 1617, 1485, 1395, 1338, 1206. $^1$H-NMR (60 MHz, d$_6$-DMSO, δ): 2.45 (3H, s, CH$_3$), 3.8 (3H, s, OCH$_3$), 4.3–4.8 (1H, br, COOH), 7.0 (1H, d, J=2 Hz, pyridine ring H), 7.3 (1H, d, J=2 Hz, pyridine ring H).

Synthesis Example 42

Synthesis of 2-[[[(4-Methoxy-6-methylpyridin-2-yl)carbonyl]-amino]sulfonyl]benzoic Acid Methyl Ester [Compound (I-254)]

Using 2-(aminosulfonyl)benzoic acid methyl ester [Compound (III-3)] (0.45 g, 2.1 mmol) and 4-methoxy-6-methyl-2-pyridinecarboxyloic acid [Compound (II-74)] (0.35 g, 2.1 mmol), the compound (I-254) was synthesized according to the process of Synthesis Example 3.

White solid, m.p.: 144–146° C., yield: 0.25 g, percent yield: 33.6%. IR KBr cm$^{-1}$: 3328, 1731, 1605, 1473, 1443, 1413, 1359, 1287, 1185, 861, 603. $^1$H-NMR (60 MHz, CDCl$_3$, δ): 2.5 (3H, s, CH$_3$), 3.74 (3H, s, COOCH$_3$ or OCH$_3$), 3.93 (3H, s, COOCH$_3$ or OCH$_3$), 6.71 (1H, d, J=2 Hz, pyridine ring H), 7.33 (1H, d, J=2 Hz, pyridine ring H), 7.4–7.66 (3H, m, aromatic ring H), 8.1–8.4 (1H, m, aromatic ring H), 9.0–9.5 (1H, bs, NH).

Synthesis Example 43

Synthesis of 5,6-Dimethoxy-2-pyridinecarboxylic Acid Phenyl Ester (IV-79)

(1) Synthesis of 5,6-dimethoxy-2-pyridinecarboxylic acid Methyl ester (XV-79)

Methanol (2 g, 83 mmol) and sodium hydride (60% in mineral oil, 0.625 g, 15.64 mmol) were added to 50 ml of dry dioxane. After conclusion of bubbling, 6-chloro-5-methoxy-2-pyridinecarboxylic acid methyl ester (XVI-78) (3.0 g, 14.9 mmol) and cuprous iodide (2.83 g, 14.9 mmol) were added thereto, followed by heating at 100° C. with stirring for 8 hours. The reaction solution was cooled and filtered by a glass filter equipped with a super cell. The filtrate was concentrated and the residue was then distributed with ethyl acetate and water. An organic layer was separated and dried with sodium sulfate (anhydrous). After the solvent was distilled off, the residue was purified with silica gel column chromatography.

White solid, m.p.: 92–94° C., yield: 1.56 g, percent yield: 53.4%. IR KBr cm$^{-1}$: 1730, 1600, 1510, 1390, 1250, 1130, 1030, 770, 640. $^1$H-NMR (60 MHz, CDCl$_3$, δ): 3.85 (6H, s, OCH$_3$ and COOCH$_3$), 4.03 (3H, s, OCH$_3$), 7.00 (1H, d, J=8 Hz, pyridine ring H), 7.68 (1H, d, J=8 Hz, pyridine ring H).

(2) Synthesis of 5,6-dimethoxy-2-pyridinecarboxylic acid (II-79)

Synthesis of 5,6-dimethoxy-2-pyridinecarboxylic acid methyl ester (XV-79) (1.56 g, 7.9 mmol) was hydrolyzed in a solution consisting of sodium hydroxide (0.32 g, 7.9×1.01 mmol) and 3.2 ml of water and 31 ml of ethyl alcohol to obtain the Compound (II-79)

White solid, m.p.: 175–176° C., yield: 1.07 g, percent yield: 74.6%. IR KBr cm$^{-1}$: 2968, 1695, 1581, 1497, 1419, 1305, 1278. $^1$H-NMR (60 MHz, d$_6$-DMSO, δ): 3.78 (3H, s, OCH$_3$), 3.85 (3H, s, OCH$_3$), 7.26 (1H, d, J=8 Hz, pyridine ring H), 7.61 (1H, d, J=8 Hz, pyridine ring H).

(3) Synthesis of 5,6-dimethoxy-2-pyridinecarboxylic acid phenyl ester (IV-79)

5,6-Dimethoxy-2-pyridinecarboxyloic acid (0.744 g, 4.065 mmol) was allowed to react with thionyl chloride (2.42 g, 4.06×5 mmol) to synthesize 5,6-dimethoxy-2-pyridinecarboxylic acid chloride, which was then allowed to react with phenol (0.4 g, 4.065×1.05 mmol) to obtain the Compound (IV-79).

White solid, m.p.: 121–123° C., yield: 0.904 g, percent yield: 86.1%. IR KBr cm$^{-1}$: 1749, 1494, 1275, 1233, 1194, 1008. $^1$H-NMR (60 MHz, CDCl$_3$, δ): 3.86 (3H, s, OCH$_3$), 4.05 (3H, s, OCH$_3$), 7.03 (1H, d, J=8 Hz, pyridine ring H), 7.05–7.56 (5H, m, aromatic ring H), 7.80 (1H, d, J=8 Hz, pyridine ring H).

Synthesis Example 44

Synthesis of 2-[[[(5,6-Dimethoxypyridin-2-yl)carbonyl]-amino]sulfonyl]benzoic Acid Methyl Ester (I-259)

Using phenylsulfonamide (III-3) (0.352 g, 1.64 mmol) and 5,6-dimethoxy-2-pyridinecarboxyolic acid (II-79) (0.3 g, 1.64 mmol), the Compound (I-259) was synthesized according to the process of Synthesis Example 3. The product was purified by silica gel column chromatography.

Light brown solid, m.p.: 162–163° C., yield: 0.34 g, percent yield: 54.5%. IR KBr cm$^{-1}$: 3256, 1731, 1715, 1500, 1404, 1344, 1281, 1185, 1113, 750, 564. $^1$H-NMR (60 MHz, CDCl$_3$, δ): 3.85 (3H, s, OCH$_3$ or COOCH$_3$), 3.90 (3H, s, OCH$_3$ or COOCH$_3$), 4.10 (3H, s, OCH$_3$), 7.03 (1H, d, J=8 Hz, pyridine ring H), 7.45–7.80 (3H, m, aromatic ring H), 7.66 (1H, d, J=8 Hz, pyridine ring H), 8.20–8.46 (1H, m, aromatic ring H), 10.68 (1H, br, NH).

Synthesis Example 45
Synthesis of N-[[2-(N,N-Dimethylaminosulfonyl)phenyl]-sulfonyl]-5,6-dimethoxy-2-pyridinecarboxamide (I-889)

Using phenylsulfonamide (III-13) (0.255 g, 0.96 mmol) and 5,6-dimethoxy-2-pyridinecarboxyolic acid phenyl ester (IV-79) (0.25 g, 0.96 mmol), the Compound (I-889) was synthesized according to the process of Synthesis Example 1. The product was washed with little hot acetonitrile.

White solid, m.p.: 224–226° C., yield: 0.33 g, percent yield: 80.4%. IR KBr cm$^{-1}$: 3340, 1716, 1500, 1413, 1341, 1281, 1185, 753, 603. $^1$H-NMR (60 MHz, CDCl$_3$, δ): 2.90 [6H, s, N(CH$_3$)$_2$], 3.85 (3H, s, OCH$_3$), 4.10 (3H, s, OCH$_3$), 7.00 (1H, d, J=8 Hz, pyridine ring H), 7.46–8.1 (3H, m, aromatic ring H), 7.85 (1H, d, J=8 Hz, pyridine ring H), 8.40–8.68 (1H, m, aromatic ring H), 10.60–11.56 (1H, br, NH).

Synthesis Example 46
Synthesis of N-[(2-Trifluoromethoxyphenyl)sulfonyl]-5,6-dimethoxy-2-pyridinecarboxamide (I-799)

Using phenylsulfonamide (III-12) (0.232 g, 0.965 mmol) and 2-pyridinecarboxyolic acid phenyl ester (IV-79) (0.25 g, 0.965 mmol), the Compound (I-799) was synthesized according to the process of Synthesis Example 1.

White solid, m.p.: 149–151° C., yield: 0.29 g, percent yield: 74.3%. IR KBr cm$^{-1}$: 3350, 1719, 1500, 1407, 1353, 1278, 1251, 1185. $^1$H-NMR (60 MHz, CDCl$_3$, δ): 3.90 (3H, s, OCH$_3$), 4.03 (3H, s, OCH$_3$), 7.06 (1H, d, J=8 Hz, pyridine ring H), 7.15–7.81 (3H, m, aromatic ring H), 7.67 (1H, d, J=8 Hz, pyridine ring H), 8.27 (1H, dd, J=2 Hz, 8 Hz, aromatic ring H), 10.1 (1H, br, NH).

Synthesis Example 47
Synthesis of 6-Chloro-2-pirydinecarboxylic Acid Phenyl Ester [Compound (IV-51)]

6-Chloro-2-picoline [A=H, Ym=6-Cl in Compound (IX)] (7 g, 0.0548 mol) was mixed with 38 ml of water and the mixture was stirred to 50–60° C. on a hot bath. To the resultant mixture was added potassium permanganate (9.1 g, 0.0548×1.05 mol). After be stirred for 1 hour, potassium permanganate (9.1 g, 0.0548×1.05 mol) was additionally added to the mixture, which was stirred vigorously for 2 hours. The reaction mixture was filtered by a glass filter equipped with a high-flow super cell. The filtrate was washed with ethyl acetate and the aqueous layer was acidified with diluted hydrochloric acid. Since a solid did not formed, water was distilled off under vacuum till dryness. The resultant solid was extracted 5 times with 50 ml of methanol, followed by distilling off the methanol to give 2.8 g of a white solid. The resulted 6-chloro-2-pyridinecarboxylic acid (2.4 g, 0.0152 mol) was mixed with 20 ml of benzene and refluxed with heat in the presence of thionyl chloride (9.5 g, 0.0152×5.25 mol) and a catalytic amount of N,N-dimethylformamide. Thereafter, the treatment was carried out according to Synthesis Example 25 (4)

White solid, m.p.: 75–76° C., yield: 2.59 g, percent yield: 72.7%. IR KBr cm$^{-1}$: 1758, 1596, 1296, 1245. $^1$H-NMR (60 MHz, CDCl$_3$, δ): 6.56–8.15 (8H, m, aromatic ring H, pyridine ring H).

Synthesis Example 48
Synthesis of N-[[2-(N,N-Dimethylaminosulfonyl)phenyl]-sulfonyl)-6-chloro-2-pirydinecarboxamide [Compound (I-861)]

Using 2-(N,N-dimethylaminosulfonyl) phenylsulfonamide [Compound (III-13) (0.249 g, 0.94 mmol)] and 6-chloro-2-pyridinecarboxyolic acid phenyl ester [Compound (IV-51)] (0.22 g, 0.94 mmol), the Compound (I-861) was synthesized according to the process of Synthesis Example 1.

White solid, m.p.: 207–209° C., yield: 0.25 g, percent yield: 67.8%. IR KBr cm$^{-1}$: 3298, 1731, 1452, 1317, 1188, 1152. $^1$H-NMR (60 MHz, d$_6$-DMSO, δ): 2.80 [6H, s, N(CH$_3$)$_2$], 7.63–8.10 (6H, m, aromatic ring H, pyridine ring H), 8.20–8.50 (1H, aromatic ring or pyridine ring H), NH indistinctness.

Synthesis Example 49
Synthesis of N-[[2-Trifluoromethoxyphenyl]sulfonyl]-6-chloro-2-pyridinecarboxamide [Compound (I-771)]

Using 2-trifluoromethoxyphenylsulfonamide [Compound (III-12)] (0.263 g, 1.09 mmol) and 6-chloro-2-pyridinecarboxyolic acid phenyl ester [Ym=6-Cl, Zs=H in Compound (IV)] (0.255 g, 1.09 mmol), the Compound (I-771) was synthesized according to the process of Synthesis Example 1.

White solid, m.p.: 94–95° C., yield: 0.29 g, percent yield: 69.7%. IR KBr cm$^{-1}$: 3334, 1734, 1455, 1407, 1359, 1290, 1263, 1188. $^1$H-NMR (60 MHz, CDCl$_3$, δ): 7.10–8.05 (6H, m, aromatic ring H, pyridine ring H), 8.05 (1H, dd, J=2 Hz, 8 Hz, pyridine ring H), NH indistinctness.

Synthesis Example 50
Synthesis of N-[(2,6-Dichlorophenyl)sulfonyl]-6-chloro-2-pyridinecarboxamide [Compound (I-591)]

Using 2,6-dichlorophenylsulfonamide [Compound (III-7)] (0.247 g, 1.09 mmol) and 6-chloro-2-pyridinecarboxyolic acid phenyl ester [Compound (IV-51)] (0.255 g, 1.09 mmol), the Compound (I-591) was synthesized according to the process of Synthesis Example 1.

White solid, m.p.: 140–142° C., yield: 0.158 g, percent yield: 39.5%. IR KBr cm$^{-1}$: 3358, 3304, 1722, 1707, 1449, 1371, 1188. $^1$H-NMR (60 MHz, CDCl$_3$, δ): 7.16–7.83 (5H, m, aromatic ring H, pyridine ring H), 7.93 (1H, m, aromatic ring H or pyridine ring H), NH indistinctness.

Synthesis Example 51
Synthesis of 2-[[[(6-Chloropyridin-2-yl)carbonyl]amino]-sulfonyl]benzoic Acid Methyl Ester [Compound (I-231)]

Using 2-methoxycarbonylphenylsulfonamide [Compound (III-3)] (0.319 g, 1.48 mmol) and 6-chloro-2-pyridinecarboxyolic acid phenyl ester [Compound (IV-51)] (0.346 g, 1.48 mmol), the Compound (I-231) was synthesized according to the process of Synthesis Example 1.

White solid, m.p.: 122–124° C., yield: 0.29 g, percent yield: 55.7%. IR KBr cm$^{-1}$: 3328, 1746, 1725, 1452, 1185, 1062, 756. $^1$H-NMR (60 MHz, CDCl$_3$, δ): 4.0 (3H, s, OCH$_3$), 7.30–8.06 (6H, m, aromatic ring 3H, pyridine ring 3H), 8.06–8.46 (1H, m, aromatic ring H), 10.1–10.7 (1H, br, NH).

Synthesis Example 52
Synthesis of Starting Material: Synthesis of 2-Amino-N-methyl-N-methoxyphenylsulfonamide [Xn=2-SO$_2$N(OCH$_3$)CH$_3$ in Compound (XXV)]

(1) Synthesis of N-methyl-N-methoxy-2-nitrophenylsulfonamide:

2-Nitrobenzenesulfonyl chloride (5 g, 22.5 mmol) was allowed to react with N-methyl-N-methoxyamine hydrochloride (2.42 g, 22.5×1.2 mmol) in the presence of triethylamine (5.47 g, 22.5×2.4 mmol) to obtain 5.3 g (percent yield: 95.3%) of N-methyl-N-methoxy-2-nitrophenylsulfonamide.

White solid, m.p.: 105–106° C. IR KBr cm$^{-1}$: 1554, 1365, 1188, 1071, 780. $^1$H-NMR (60 MHz, CDCl$_3$, δ): 2.9 (3H, s, N—CH₃), 3.75 (3H, s, N—OCH₃), 7.43–8.13 (4H, m, aromatic ring H).

(2) Synthesis of 2-amino-N-methyl-N-methoxyphenylsulfonamide [Xn=2-SO₂N(OCH₃)CH₃ in Compound (XXV)]:

N-Methyl-N-methoxy-2-nitrophenylsulfonamide (6.17 g, 25.08 mmol) was reduced with reduced iron (4.14 g, 25.08× 2.93 mmol) to obtain 5.4 g (percent yield: 99.68%) of 2-amino-N-methoxyphenylsulfonamide [Xn=2-SO₂N (OCH₃)CH₃ in Compound (XXV)].

White solid, m.p.: 50° C. IR KBr cm⁻¹: 3526, 3418, 1635, 1605, 1491, 1335, 1146, 1020, 753. ¹H-NMR (60 MHz, CDCl₃, δ): 2.83 (3H, s, N—CH₃), 3.65 (3H, s, N—OCH₃), 4.6–5.5 (2H, br, NH₂), 6.45–6.85 (2H, m, aromatic ring H), 7.06–7.3 (1H, m, aromatic ring H), 7.55 (1H, dd, J=2 Hz, 8 Hz, aromatic ring H).

Synthesis Example 53
Synthesis of 2-[(N-Methyl-N-methoxyamino)sulfonyl] phenylsulfonamide [Compound (III-18)]

2-amino-N-methyl-N-methoxyphenylsulfonamide [Xn= 2-SO₂N(OCH₃)CH₃ in Compound (XXV)] (5.4 g, 25 mmol) was diazotized with sodium nitrite (2.07 g, 25×1.2 mmol) and the resultant diazonium compound was allowed to react with sodium hydrogen sulfate (7.28 g, 25×2.8 mmol) to obtain 3.95 g (percent yield: 56.37%) of 2-[(N-methyl-N-methoxyamino)sulfonyl] phenylsulfonamide [Compound (III-18)].

Light yellow solid, m.p.: 136–140° C. IR KBr cm⁻¹: 3418, 3286, 1551, 1434, 1344, 1176, 1020, 783. ¹H-NMR (60 MHz, d₆-DMSO, δ): 2.85 (3H, s, N—CH₃), 3.63 (3H, s, N—OCH₃), 6.9–7.36 (2H, br, NH₂), 7.6–8.3 (4H, m, aromatic ring H).

Synthesis Example 54
Synthesis of 2-(Methylsulfonyl)phenylsulfonamide [Compound (III-21)]

(1) Synthesis of 2-(methylmercapto)acetanilide

2-Methylmercaptoaniline (6 g, 43.1 mmol) was allowed to react with anhydrous acetic acid (21.9 g, 43.1×5 mmol) to obtain 7.8 g (percent yield: 99.8%) of 2-(methylmercapto) acetanilide.

White solid, m.p.: 100° C. IR KBr cm⁻¹: 3040, 1662, 1578, 1548, 1473, 1437, 1374, 1305. ¹H-NMR (60 MHz, CDCl₃, δ): 2.16 (3H, s, COCH₃), 2.3 (3H, s, SCH₃), 6.8–7.56 (3H, m, aromatic ring H), 7.56–8.0 (1H, m, aromatic ring H), 8.0–8.5 (1H, br, NH).

(2) Synthesis of 2-(methylsulfonyl)acetanilide

2-Methylmercaptoacetanilide (7.8 g, 43.09 mmol) was oxidized with 31% hydrogen peroxide (14.18 g, 43.09×3 mmol) in 54.6 g of acetic acid to obtain 7.96 g (percent yield: 86.72%) of 2-(methylsulfonyl)acetanilide.

Light yellow solid, m.p.: 140–141° C. IR KBr cm⁻¹: 3334, 1686, 1584, 1518, 1446, 1314, 1149, 966, 783, 762. ¹H-NMR (60 MHz, CDCl₃, δ): 2.16 (3H, s, COCH₃), 3.0 (3H, s, SO₂CH₃), 7.0–7.7 (2H, m, aromatic ring H), 7.8 (1H, dd, J=2 Hz, 7 Hz, aromatic ring H), 8.36 (1H, dd, J=2 Hz, 7 Hz, aromatic ring H), 8.95–9.8 (1H, br, NH). MS[DI]: m/z 213 (M+, 27), 171 (97), 134 (55), 92 (86), 43 (10).

(3) Synthesis of 2-(methylsulfonyl)aniline [Xn=2-SO₂CH₃ in Compound (XXV)].

2-(Methylsulfonyl)acetanilide (7.96 g, 37.37 mmol) was hydrolyzed in a mixture of sodium hydroxide (1.79 g, 37.37×1.2 mmol), 18 ml of water and 50 ml of EtOH to obtain 5.57 g (percent yield: 87.16%) of 2-(methylsulfonyl) aniline [Xn=2-SO₂CH₃ in Compound (XXV)].

Light yellow liquid. IR KBr cm⁻¹: 3502, 3394, 1629, 1491, 1320, 1290. ¹H-NMR (60 MHz, CDCl₃, δ): 3.0 (3H, s, SO₂CH₃), 4.5–5.3 (2H, br, NH₂), 6.5–6.8 (2H, m, aromatic ring H), 7.05–7.4 (1H, m, aromatic ring H), 7.5–7.75 (1H, m, aromatic ring H).

(4) Synthesis of 2-(methylsulfonyl)phenylsulfonamide [Compound (III-21)]

2-(Methylsulfonyl)aniline [Xn=2-SO₂CH₃ in Compound (XXV)] (5.57 g, 32.5 mmol) was diazotized with sodium nitrite (2.706 g, 32.5×1.2 mmol) and the resultant diazonium compound was allowed to react with sodium hydrogen sulfate (9.47 g, 32.5×2.8 mmol) to obtain 3.87 g (percent yield: 50.67%) of 2-(methylsulfonyl)phenylsulfonamide [Compound (III-21)].

White solid, m.p.: 249–250° C. IR KBr cm⁻¹: 3370, 3262, 1353, 1302, 1164, 1149, 1044. ¹H-NMR (60 MHz, d₆-DMSO, δ): 3.36 (3H, s, SO₂CH₃), 6.9–7.3 (2H, br, NH₂), 7.6–8.2 (4H, m, aromatic ring H).

Synthesis Example 55
Synthesis of 6-Bromo-5-methoxy-N-[[2-(methylsulfonyl)-phenyl]sulfonyl]-2-pyridinecarboxamide [Compound (I-819)]

Using 2-(methylsulfonyl)phenylsulfonamide (III-21) (0.153 g, 0.65 mmol) and 6-bromo-5-methoxy-2-pyridinecarboxylic acid phenyl ester [Compound (IV-85)] (0.2 g, 0.65 mmol), the compound (I-819) was synthesized according to the process of Synthesis Example 1.

White solid, m.p.: 208–210° C., yield: 0.19 g, percent yield: 63.45%. IR KBr cm⁻¹: 1725, 1569, 1422, 1356, 1314, 1185, 1155. ¹H-NMR (60 MHz, CDCl₃, δ): 3.38 (3H, s, SO₂CH₃), 3.86 (3H, s, OCH₃), 7.08 (1H, d, J=8 Hz, pyridine ring H), 7.63–8.0 (3H, m, aromatic ring H×2, pyridine ring H), 8.1–8.3 (1H, m, aromatic ring H), 8.35–8.58 (1H, m, aromatic ring H), 10.3–10.75 (1H, br, NH).

Synthesis Example 56
Synthesis of 6-Bromo-5-methoxy-N-[[2-(N-methyl-N-methoxyaminosulfonyl]phenyl]sulfonyl]-2-pyridinecarboxamide [Compound (I-830)]

Using 2-[(N-methyl-N-methoxyamino)sulfonyl] phenylsulfonamide [Compound (III-18)] (0.182 g, 0.65 mmol) and 6-bromo-5-methoxy-2-pyridinecarboxylic acid phenyl ester [Compound (IV-85)] (0.2 g, 0.65 mmol), the Compound (I-830) was synthesized according to the process of Synthesis Example 1.

White solid, m.p.: 184–185° C., HPLC (247 nm) purity: 98.3%. IR KBr cm⁻¹: 1722, 1440, 1569, 1404, 1350, 1278, 1188, 1008, 555. ¹H-NMR (60 MHz, d₆-DMSO, δ): 2.8 (3H, s, N—CH₃), 3.4 (3H, s, N—OCH₃), 3.9 (3H, s, OCH₃), 7.56 (1H, d, J=8 Hz, pyridine ring H), 7.8–8.2 (4H, m, aromatic ring H×3, pyridine ring H), 8.26–8.5 (1H, m, aromatic ring H).

Synthesis Example 57
Synthesis of 6-Chloro-4-methoxy-N-[[2-(methylsulfonyl)-phenyl]sulfonyl]-2-pyridinecarboxamide [Compound (I-818)]

2-(Methylsulfonyl)phenylsulfonamide [Compound (III-21)] (0.178 g, 0.78 mmol) was allowed to react with 6-chloro-4-methoxy-2-pyridinecarboxyolic acid phenyl ester [Compound (IV-75)] (0.2 g, 0.76 mmol) according to the process of Synthesis Example 1 to synthesize the compound (I-818).

White solid, m.p.: 194–196° C., yield: 0.25 g, percent yield: 81.53%. HPLC (247 nm) purity: 99.4%. IR KBr cm⁻¹: 1731, 1596, 1473, 1437, 1395, 1353, 1314, 1155, 1032. ¹H-NMR (60 MHz, d₆-DMSO, δ): 3.4 (s, SO₂CH₃), 3.8 (3H, s, OCH₃), 6.9 (1H, d, J=2 Hz, pyridine ring H), 7.4 (1H, d, J=2 Hz, pyridine ring H), 7.63–7.93 (2H, m, aromatic ring H), 8.03–8.63 (2H, m, aromatic ring H), NH indistinctness.

Synthesis Example 58
Synthesis of 6-Chloro-4-methoxy-N-[[2-(N-methyl-N-methoxyamino)sulfonyl]phenylsulfonyl]-2-pyridinecarboxamide [Compound (I-838)]

Using 2-(N-methyl-N-methoxyaminosulfonyl) phenylsulfonamide [Compound (III-18)] (0.213 g, 0.76 mmol) and 6-chloro-4-methoxy-2-pyridinecarboxyolic acid phenyl ester [Compound (IV-75)] (0.2 g, 0.76 mmol), the Compound (I-838) was synthesized according to the process of Synthesis Example 1.

White solid, m.p.: 148–149° C., yield: 0.26 g, percent yield: 77.4%. HPLC (247 nm) purity: 98.6%. IR KBr cm$^{-1}$: 1719, 1599, 1473, 1428, 1359, 1188, 1041, 873. $^1$H-NMR (60 MHz, d$_6$-DMSO, δ): 2.8 (3H, s, N—CH$_3$), 3.4 (3H, s, N—OCH$_3$), 3.8 (3H, s OCH$_3$), 7.3 (1H, d, J=2 Hz, pyridine ring H), 7.4 (1H, d, J=2 Hz, pyridine ring H), 7.7–8.1 (3H, m, aromatic ring H), 8.16–8.46 (1H, m, aromatic ring H), NH indistinctness.

Synthesis Example 59
Synthesis of 6-Chloro-4-methoxy-N-[[2-(N,N-dimethylaminosulfonyl)phenyl]sulfonyl]-2-pyridinecarboxamide [Compound (I-885)]

Using 2-(N,N-dimethylaminosulfonyl) phenylsulfonamide [Compound (III-13)] (0.2 g, 0.76 mmol) and 6-chloro-4-methoxy-2-pyridinecarboxylic acid phenyl ester [Compound (IV-75)] (0.2 g, 0.76 mmol), the compound (I-885) was synthesized in the presence of sodium hydride (0.03 g, 0.76×1.1 mmol) according to the process of Synthesis Example 1.

White solid, m.p.: 201–203° C., yield: 0.28 g, percent yield: 85.2%. HPLC (247 nm) purity: 98.3%. IR KBr cm$^{-1}$: 1725, 1602, 1560, 1473, 1437, 1341, 1155. $^1$H-NMR (60 MHz, d$_6$-DMSO, δ): 2.8 [6H, s, N(CH$_3$)$_2$], 3.86 (3H, s, OCH$_3$), 7.36 (1H, d, J=2 Hz, pyridine ring H), 7.43 (1H, d, J=2 Hz, pyridine ring H), 7.66–8.0 (3H, m, aromatic ring H), 8.06–8.46 (1H, m, aromatic ring H), NH indistinctness.

Synthesis Example 60
Synthesis of 6-Bromo-5-difluoromethoxy-N-[[2-(N,N-dimethyl-aminosulfonyl)phenyl]sulfonyl]-2-pyridinecarboxamide [Compound (I-900)]

Using 2-[(N,N-dimethylaminosulfonyl)phenyl] sulfonamide [Compound (III-13)] (0.15 g, 0.58 mmol) and 6-bromo-5-difluoromethoxypicolinic acid phenyl ester [Compound (IV-90)] (0.2 g, 0.58 mmol), the Compound (I-900) was synthesized according to the process of Synthesis Example 1.

White solid, m.p.: 140° C., yield: 0.185 g, percent yield: 61.9%. IR KBr cm$^{-1}$: 3352, 1716, 1455, 1413, 1344, 1269, 1188, 1161, 1074, 975. $^1$H-NMR (60 MHz, CDCl$_3$, δ): 2.9 (6H, s, N(CH$_3$)$_2$], 6.6 (1H, t, J=72 Hz, OCHF$_2$), 7.5 (1H, d, J=8 Hz, pyridine ring H), 7.9 (1H, d, J=8 Hz, pyridine ring H), 7.56–8.0 (3H, m, aromatic ring H), 8.3–8.5 (1H, m, aromatic ring H), 10.3–11.1 (1H, br, NH).

Synthesis Example 61
Synthesis of N-[[2-(N,N-Dimethylaminosulfonyl)phenyl]-sulfonyl]-6-methyl-5-nitro-2-pyridinecarboxamide [Compound (I-868)]

Using 2-[(N,N-dimethylaminosulfonyl)phenyl] sulfonamide [Compound (III-13)] (0.26 g, 0.98 mmol) and 6-methyl-5-nitropicolinic acid phenyl ester (IV-92) (0.252 g, 0.98 mmol), the Compound (I-868) was synthesized according to the process of Synthesis Example 1.

Light brown solid, m.p.: 165° C. decomposition, yield: 0.358 g, percent yield: 85.3%. IR KBr cm$^{-1}$: 1734, 1533, 1446, 1344, 1323, 1158, 756. $^1$H-NMR (60 MHz, CDCl$_3$, δ): 2.87 (3H, s, CH$_3$), 2.9 [6H, s, N(CH$_3$)$_2$], 7.5–8.73 (6H, m, aromatic ring H, pyridine ring H), 10.9–11.3 (1H, br, NH).

Synthesis Example 62
Synthesis of 6-Methyl-5-methoxy-2-pyridinecarboxylic Acid Phenyl Ester [Ym=5-OCH$_3$-6-CH$_3$, s=0 in Compound (IV)]

(1) Synthesis of 3-methoxy-2-methylpyridine-N-oxide:

To a solution obtained by dissolving 3-methoxy-2-methylpyridine (14.8 g, 0.12 mol) in acetic acid (44 g, 0.12×2.5 mol) was added 31% hydrogen peroxide (33 g, 0.12×2.5 mol), followed by stirring in an oil bath at 100° C. for 16 hours. The reaction solution was then cooled and poured into iced-water. To the mixture was then added sodium carbonate (solid) so as to be weak alkalinity. The resultant solution was extracted with ethyl acetate to obtain 1.45 g (percent yield: 16.7%) of 3-methoxy-2-methylpyridine-N-oxide IR KBr cm$^{-1}$: 1668, 1647, 1584, 1503, 1302, 1266, 1188, 1128, 792. $^1$H-NMR (60 MHz, CDCl$_3$, δ): 2.4 (3R, s, CH$_3$), 3.8 (3H, s, OCH$_3$), 6.5–7.2 (2H, m, pyridine ring H×2), 7.7–8.0 (1H, m, pyridine ring H).

(2) Synthesis of 2-cyano-5-methoxy-6-methylpyridine

To a solution obtained by dissolving 3-methoxy-2-methyl-pyridine-N-oxide (1.57 g, 11.3 mmol) in 30 ml of dichloromethane were added cyanotrimethylsilane (1.12 g, 11.3 mmol) and dimethylcarbamoyl chloride (1.21 g, 11.3 mmol), followed by stirring at room temperature for 9 days. The reaction solution was washed with 10% sodium carbonate aqueous solution and then with water. The organic layer was dried with sodium sulfate and concentrated to remove the solvent, by which 0.198 g (percent yield: 11.8%) of 2-cyano-5-methoxy-6-methylpyridine was obtained.

White solid, m.p.: 114–6° C. IR KBr cm$^{-1}$: 2236, 1587, 1467, 1443, 1266, 1140, 834. $^1$H-NMR (60 MHz, CDCl$_3$, δ): 2.4 (3H, s, CH$_3$), 3.8 (3H, s, OCH$_3$), 7.0 (1H, d, J=8 Hz, pyridine ring H), 7.4 (1H, d, J=8 Hz, pyridine ring H).

(3) Synthesis of 6-methyl-5-methoxy-2-pyridinecarboxylic acid phenyl ester:

2-Cyano-5-methoxy-6-methylpyridine [Compound (X-859)] (0.1489 g, 0.001 mol) was hydrolyzed with 10 ml of 35% hydrochloric acid by stirring in an oil bath at 100° C. for 1.5 hours. Water in the reaction solution was then completely distilled off to obtain 6-methyl-5-methoxy-2-pyridinecarboxylic acid (m.p.: 183° C., IR KBr cm$^{-1}$: 1746, 1644, 1557, 1398, 1293, 1206, 1017) as a residue. After 3 ml of thionyl chloride and benzene and a catalytic amount of DME were added to the residue, the resultant mixture was refluxed with heat for 1 hour. Thereafter, an excess amount of thionyl chloride and benzene was distilled of under vacuum.

The residue was dissolved in 5 ml of dichloromethane, which was added dropwise under cooling with water to a solution prepared by adding phenol (0.094 g, 0.001 mol) and triethylamine (0.11 g, 0.001×1.1 mol) in 5 ml of dichloromethane. The reaction solution was then stirred at room temperature for 1 hour. Thereafter, the reaction solution was washed by adding diluted hydrochloric acid and then with water. After the organic layer was dried, the solvent was distilled off, and the residue was purified by silica gel column chromatography to obtain a solid.

6-Methyl-5-methoxy-2-pyridinecarboxylic Acid Phenyl Ester:

White solid, m.p.: 103–105° C., yield: 0.146 g, percent yield: 60.3% IR KBr cm$^{-1}$: 1752, 1593, 1578, 1497, 1443, 1323, 1260, 1197, 1140, 1122. $^1$H-NMR (60 MHz, CDCl$_3$, δ): 2.5 (3H, s, CH$_3$), 3.8 (3H, s, OCH$_3$), 7.0 (1H, d, J=9 Hz, pyridine ring H), 7.0–7.4 (5H, m, aromatic ring H), 8.0 (1H, d, J=9 Hz, pyridine ring H).

Synthesis Example 63
Synthesis of N-[[2-(N,N-Dimethylaminosulfonyl)phenyl]-sulfonyl]-6-methyl-5-methoxy-2-pyridinecarboxamide [Compound (I-859)]

Using 2-(N,N-dimethylaminosulfonyl)phenyl] sulfonamide [Compound (III-13)] (0.102 g, 0.385 mmol) and 6-methyl-5-methoxypicolinic acid phenyl ester [Ym=5-OCH$_3$-6-CH$_3$, s=0 in Compound (IV)] (0.0937 g, 0.385 mmol), the Compound (I-859) was synthesized according to the process of Synthesis Example 1.

IR KBr cm$^{-1}$: 1722, 1578, 1467, 1398, 1353, 1170, 966, 753. $^1$H-NMR (60 MHz, CDCl$_3$, δ): 2.4 (3H, s, CH$_3$), 2.9 [6H, s, N(CH$_3$)$_2$], 3.8 (3H, s, OCH$_3$), 7.05 (1H, d, J=9 Hz, pyridine ring H), 7.3–8.1 (3H, m, aromatic ring H), 7.9 (1H, d, J=9 Hz, pyridine ring H), 8.3–8.6 (1H, m, aromatic ring H), NH indistinctness.

Synthesis Example 64
Synthesis of 2-(N,N-Diethylaminosulfonyl) benzenesulfonamide [Compound (III-8)]

(1) Synthesis of 2-(N,N-diethylaminosulfonyl) nitrobenzene:

Using 2-nitrobenzenesulfonyl chloride (16.5 g, 74.4 mmol) and diethylamine (8.16 g, 74.4×1.5 mmol), 2-(N,N-diethyloamino-sulfonyl)nitrobenzene was synthesized according to the process of Synthesis Example 31 (1).

Light yellow liquid, yield: 19.0 g, percent yield: 98.9% IR NaCl liq. film cm$^{-1}$: 2992, 2950, 1554, 1362, 1206, 1161, 1020, 945, 780. $^1$H-NMR (60 MHz, CDCl$_3$, δ): 1.1 (6H, t, J=7 Hz, CH$_3$×2), 3.3 (4H, q, J=7 Hz, CH$_2$×2), 7.4–8.0 (4H, m, aromatic ring H).

(2) Synthesis of 2-(N,N-diethyloaminosulfonyl)aniline:

Using 2-(N,N-diethylaminosulfonyl)nitrobenzene (19.7 g, 76.28 mmol) and reduced iron (12.5 g, 76.28×2.98 mmol), 2-(N,N-diethyloaminosulfonyl)aniline was synthesized according to the process of Synthesis Example 31 (2).

Light yellow solid, m.p.: 46–47° C., yield: 15.5 g, percent yield: 89.2% IR KBr cm$^{-1}$: 3514, 3412, 1623, 1491, 1320, 1140, 1017, 936, 756. $^1$H-NMR (60 MHz, CDCl$_3$, δ): 1.1 (6H, t, J=7 Hz, CH$_3$×2), 3.2 (4H, q, J=7 Hz, CH$_2$×2), 4.6–5.1 (2H, br, NH$_2$), 6.44–7.6 (4H, m, aromatic ring H).

(3) Synthesis of 2-(N,N-diethyloaminosulfonyl) benzenesulfonamide:

2-(N,N-diethylaminosulfonyl)aniline (15.26 g, 66.8 mmol) was diazotized by reacting with sodium nitrite (5.506 g, 66.8×1.19 mmol) according to the process of Synthesis Example 31 (3). To the resultant diazotation product were added sodium sulfite (19.46 g, 66.86×2.8 mmol)and cuprous chloride (1.32 g, 66.8×0.2 mmol) to produce 2-(N,N-diethylaminosulfonyl) benzenesulfonyl chloride, followed by reacting with a large excess amount of 29% aqueous ammonia to prepare 2-(N,N-diethylaminosulfonyl)benzenesulfonamide.

Light yellow solid, m.p.: 148–151° C., yield: 12.6 g, percent yield: 64.6% IR KBr cm$^{-1}$: 3382, 3247, 1551, 1392, 1350, 1206, 1179, 1128, 1017, 951. $^1$H-NMR (60 MHz, CDCl$_3$, δ): 1.1 [6H, t, J=7 Hz, N—(CH$_2$CH$_3$)×2], 3.4 [4H, q, J=7 Hz, N(CH$_2$—)×2], 6.6–6.9 (2H, br, NH$_2$), 7.5–8.3 (4H, m, aromatic ring H).

Synthesis Example 65
Synthesis of 3,6-Dichloro-2-pyridinecarboxylic Acid Phenyl Ester [Compound (IV-9)]

(1) Synthesis of 2,5-dichloropyridine-N-oxide

To a solution obtained by dissolving 2,5-dichloropyridine (20 g, 0.135 mol) in 240 ml of acetic acid was added 31% hydrogen peroxide (92.5 g, 0.135×6.24 mol), followed by stirring at 65° C. for 18 hours. Thereafter, the reaction solution was poured into iced-water, followed by adding sodium carbonate so as to be weak alkalinity and then extracting two times with 200 ml of chloroform. The extract was washed with 50 ml of saturated aqueous solution of sodium sulfite and with saturated saline solution. The solvent was distilled off to obtain a white solid.

m.p.: 77–80° C., Violent decomposition at 190° C. Yield: 11.9 g, percent yield: 53.7% IR KBr cm$^{-1}$: 1479, 1371, 1248, 1110, 924. $^1$H-NMR (60 MHz, CDCl$_3$, δ): 7.15 (1H, dd, J=2 Hz, 8 Hz), 7.4 (1H, d, J=8 Hz), 8.3 (1H, d, J=2 Hz).

(2) Synthesis of 3,6-dichloro-2-cyanopyridine:

2,5-Dichloropyridine-N-oxide (11.7 g, 71.38 mmol) was added little by little to dimethyl sulfate (9 g, 71.35 mmol), followed by stirring for a night. To the reaction mixture was then added 50 ml of ether, followed by stirring. Thereafter, ether was removed by decantation and the remaining ether was distilled off in vacuum. The residue was dissolved in 50 ml of water (Solution A).

On the other hand, sodium cyanide (13.77 g, 71.38×3.9 mmol) was dissolved in 67.4 ml of water and the solution was cooled to −7° C.—−15° C. under nitrogen atmosphere. To the resultant solution was added dropwise the previously prepared solution A. After the mixture was stirred at the same temperature for 1.5 hours, the resulted crystal precipitate was filtered out and washed with water, and the resultant solid was washed with a small amount of ethyl acetate.

White solid, m.p.: 90–92° C., yield: 6.6 g, percent yield: 53.6% IR KBr cm$^{-1}$: 2254, 1428, 1164, 840. $^1$H-NMR (60 MHz, CDCl$_3$, δ): 7.4 (1H, d, J=8 Hz, pyridine ring H), 7.8 (1H, d, J=8 Hz, pyridine ring H).

(3) Synthesis of 3,6-dichloro-2-pyridinecarboxylic acid [Compound (II-9)]

3,6-dichloro-2-cyanopyridine (2.5 g, 14.44 mmol) was heated to 100° C. with stirring in 15 ml of 90% sulfuric acid for 1.5 hours. Thereafter, the reaction solution was poured into 30 ml of iced water, followed by adding sodium carbonate so as to be weak alkalinity. A solid precipitate was filtered out, washed with water and dried.

White solid, m.p.: 144–145° C., yield: 2.4 g, percent yield: 86.6% IR KBr cm$^{-1}$: 1714, 1448, 1416, 1312, 1236, 1158, 1042, 836.

(4) Synthesis of 3,6-dichloro-2-pyridinecarboxylic acid phenyl ester

The captioned compound (4) was syntnesized as follows according to the process of Synthetic Example 25 (4).

3,6-Dichloro-2-pyridine carboxylic acid (1.8 g, 9.3 mmol) was heated with refluxing in the presence of 3.4 ml of thionyl chloride, benzene and a catalytic amount of DMF for 1 hour.

Thereafter, an excess amount of thionyl chloride and benzene were distilled off in vacuum and the residue was dissolved in 5 ml of dichloromethane. The resultant solution was added dropwise to a solution of phenol (0.88 g, 9.3 mmol) and triethylamine (1 g, 9.3×1.1 mmol) in 10 ml of dichloromethane under cooling with water, followed by stirring at room temperature for 2 hours. Water was then added to the reaction solution to separate an organic layer. After the organic layer was washed with a saturated aqueous solution of sodium hydrogen carbonate, it was dried and organic solvent was distilled off to obtain a solid.

White solid, m.p.: 109–111° C., yield: 1.16 g, percent yield: 46.7% IR KBr cm$^{-1}$: 1761, 1428, 1281, 1224, 1179, 1161, 1122, 1035. $^1$H-NMR (60 MHz, CDCl$_3$, δ): 7.0–7.5 (5H, m, aromatic ring H), 7.3 (1H, d, J=8 Hz, pyridine ring H), 7.7 (1H, d, J=8 Hz, pyridine ring H).

Synthesis Example 66
3,6-Dichloro-N-[[2-(N,N-Dimethylaminosulfonyl)phenyl]-sulfonyl]-2-pyridinecarboxamide [Compound (I-828)]

Using 2-(N,N-dimethylaminosulfonyl)phenylsulfonamide [Compound (III-13)] (0.197 g, 0.74 mmol) and 3,6-dichloropyridinecarboxylic acid phenyl ester [Compound (IV-9)] (0.2 g, 0.74 mmol), the Compound (I-828) was synthesized according to the process of Synthesis Example 1.

White solid, m.p.: 166–167° C., yield: 0.22 g, percent yield: 67.0% IR KBr cm$^{-1}$: 1740, 1443, 1338, 1170, 1029. $^1$H-NMR (60 MHz, d$_6$-DMSO, δ): 2.8 [6H, s, N—(CH$_3$×2)], 7.6 (1H, d, J=8 Hz, pyridine H), 7.7–8.1 (4H, m, aromatic ring H), 8.1 (1H, d, J=8 Hz, pyridine ring H), NH indistinctness.

Synthesis Example 67
Synthesis of 6-Bromo-N-[[2-(N,N-Diethylaminosulfonyl)-phenyl]sulfonyl]-5-methoxy-2-pyridinecarboxamide [Compound (I-879)]

Using 2-(N,N-diethylaminosulfonyl)phenylsulfonamide [Compound (III-8)] (0.3 g, 1.03 mmol) and 6-bromo-5-methoxy-2-pyridinecarboxylic acid phenyl ester [Compound (IV-85)] (0.31 g, 1.03 mmol), the compound (I-879) was synthesized according to the process of Synthesis Example 1.

White solid, m.p.: 220–224° C., yield: 0.37 g, percent yield: 71.6% IR KBr cm$^{-1}$: 3358, 1719, 1569, 1407, 1356, 1179, 858. $^1$H-NMR (60 MHz, d$_6$-DMSO, δ): 1.0 [6H, t, J=7 Hz, N—(CH$_2$CH$_3$×2)], 3.3 [4H, q, J=7 Hz, N(CH$_2$×2)], 3.9 (3H, s, OCH$_3$), 7.6 (1H, d, J=8 Hz, pyridine H), 7.7–8.0 (3H, m, aromatic ring H), 7.9 (1H, d, J=8 Hz, pyridine ring H), 8.1–8.5 (1H, m, aromatic ring H), NH indistinctness.

Synthesis Example 68
Synthesis of 2-[[[(3,6-Dichloropyridin-2-yl)carbonyl]-amino]sulfonyl]benzoic Acid Methyl Ester [Compound (I-189)]

Using 2-methoxycarbonylphenylsulfonamide [Compound (III-3)] (0.16 g, 0.745 mmol), 3,6-dichloro-2-pyridinecarboxylic acid phenyl ester [Compound (IV-9)] (0.2 g, 0.745 mmol) and potassium carbonate (0.126 g, 0.745 mmol), the Compound (I-189) was synthesized according to the process of Synthesis Example 1.

White solid, m.p.: 154–155° C., yield: 0.32 g, percent yield: 77.2% IR KBr cm$^{-1}$: 3328, 1755, 1734, 1446, 1350, 1296, 1179, 1032. $^1$H-NMR (60 MHz, d$_6$-DMSO, δ): 3.9 (3H, s, COOCH$_3$), 7.3 (1H, d, J=8 Hz, pyridine ring H), 7.3–7.7 (4H, m, aromatic ring H), 7.7 (1H, d, J=8 Hz, pyridine ring H), NH indistinctness.

Synthesis Example 69
Synthesis of 6-Chloro-4-methyl-2-pyridinecarboxylic Acid Phenyl Ester [Compound (IV-8)]

(1) Synthesis of 2-chloro-4-methylpyridine

2-Hydroxy-4-methylpyridine (20.3 g, 0.186 mol) was heated to 100° C. with stirring in 50 ml of phosphorus oxychloride for 4 hours. The reaction solution was poured into iced water, followed by adding sodium carbonate so as to be weak alkalinity and extracting 2 times with 200 ml of chloroform.

After the extract solution was washed with saturated saline solution, it was dried with sodium sulfate and the solvent was distilled off in vacuum. The residue was purified by silica gel column chromatography (ethyl acetate:n-hexane=1:10) to give a liquid.

Yield: 23 g, percent yield: 98.7% IR NaCl liq. Film cm$^{-1}$: 1596, 1554, 1473, 1383, 1086, 870, 825. $^1$H-NMR (60 MHz, CDCl$_3$, δ): 2.26 (3H, s, CH$_3$), 6.8–7.1 (2H, m, pyridine ring H), 8.1 (1H, d, J=4 Hz, pyridine ring H).

(2) Synthesis of 6-chloro-2-cyano-4-methylpyridine (1) Synthesis of 2-chloro-4-methylpyridine-N-oxide To a solution obtained by dissolving 2-chloro-4-methylpyridine (15.16 g, 0.1189 mol) in 240 ml of acetic acid was added 31% hydrogen peroxide (128.9 g, 0.1189× 9.88 mol), followed by stirring at 65° C. for 18 hours.

Thereafter, the reaction solution was poured into iced water, followed by adding sodium carbonate so as to be weak alkalinity and extracted 2 times with 300 ml chloroform. The extract was washed with 100 ml of saturated aqueous solution of sodium sulfite and then with saturated saline solution. After the solvent was distilled off, 30 g of the target product (purity 86.6%) was obtained, which contained the starting materials.

(2) Synthesis of 6-chloro-2-cyano-4-methylpyridine:

2-Chloro-4-methylpyridine-N-oxide (12 g, 83.6 mmol) prepared in the above (1) was added little by little to dimethyl sulfate (12.5 g, 83.6×1.19 mmol), followed stirring for a night. Thereafter, 40 ml of ether was added to the reaction mixture. Ether was then removed by decantation and remaining ether was distilled off in vacuum. The residue was dissolved in 40 ml of water (Solution A). On the other hand, sodium cyanide (16 g, 83.6×3.9 mmol) was dissolved in 78 ml of water and cooled to −7° C.−−15° C. under nitrogen atmosphere. To the resultant solution was added dropwise the previously prepared solution A. After stirring at the same temperature for 1.5 hours, the resulted crystal precipitate was filtered out and washed with water, and the solid was washed with a small amount of ethyl acetate.

Light brown solid, m.p.: 96–97° C., yield: 6.88 g, percent yield: 53.7% IR KBr cm$^{-1}$: 3082, 2248, 1596, 1446, 1398, 1188, 870. $^1$H-NMR (60 MHz, CDCl$_3$, δ): 2.4 (3H, s, CH$_3$), 7.3 (1H, s, pyridine ring H), 7.4 (1H, s, pyridine ring H).

(3) Synthesis of 6-chloro-4-methyl-2-pyridinecarboxylic acid [Compound (II-8)]

6-Chloro-2-cyano-4-methylpyridine (1.2 g, 7.86 mmol) was heated to 100° C. with stirring in 7 ml of concentrated hydrochloric acid for 30 minutes. The reaction solution was then diluted with 30 ml of water and the resulted precipitate was filtered out, washed water and dried.

White solid, m.p.: 127–128° C., yield: 1.13 g, percent yield: 84.5% IR KBr cm$^{-1}$: 3556, 1701, 1605, 1401, 1314, 1233, 1164.

(4) Synthesis of 6-chloro-4-methyl-2-pyridinecarboxylic acid phenyl ester [Compound (IV-8)]

6-Chloro-4-methyl-2-pyridinecarboxylic acid (1 g, 5.83 mmol) was suspended in 15 ml of benzene containing a catalytic amount of DMF. To the suspension was added thionyl chloride (3.46 g, 5.83 mmol), followed by refluxing with heat for 1 hour. An excess amount of thionyl chloride and benzene was then distilled off and the resultant residue was dissolved in 15 ml of dry dichloromethane.

The resultant solution was added dropwise to a solution of phenol (0.57 g, 5.83×1.05 mmol) and triethylamine (0.65 g, 5.83×1.1 mmol) in 10 ml of dichloromethane under cooling with water. After stirring for 1 hour, the reaction solution was distributed by adding 30 ml of diluted hydrochloric acid. An organic layer was separated and washed with saturated saline solution, and dried with sodium sulfate. The solvent was then distilled off to give a solid.

White solid, m.p.: 95–96° C., yield: 1.2 g, percent yield: 84% IR KBr cm$^{-1}$: 3514, 1758, 1599, 1494, 1293, 1188, 1164, 1095, 867, 732.

Synthesis Example 70
Synthesis of 3,6-Dichloro-N-[(2,6-Dichlorophenyl)sulfonyl]-2-pyridinecarboxamide [Compound (I-568)]

Using 2,6-dichlorophenylsulfonamide[Compound (III-7)] (0.17 g, 0.75 mmol) and 3,6-dichloropicolinic acid phenyl ester [Compound (IV-568)] (0.2 g, 0.75 mmol), the Compound (I-568) was synthesized according to the process of Synthesis Example 1.

White solid, m.p.: 189–190° C., yield: 0.236 g, percent yield: 78.6%. IR KBr cm$^{-1}$: 3244, 1725, 1566, 1440, 1374, 1203, 1179, 1035, 786, 612. $^1$H-NMR (60 MHz, CDCl$_3$, δ): 7.4 (1H, d, J=8 Hz, pyridine ring H), 7.4 (3H, s, aromatic ring H×3), 7.7 (1H, d, J=8 Hz, pyridine ring H), NH indistinctness.

Synthesis Example 71
Synthesis of 3,6-Dichloro-N-[(2-trifluoromethoxyphenyl)sulfonyl]-2-pyridinecarboxamide [Compound (I-738)]

Using 2-trifluoromethoxyphenylsulfonamide [Compound (III-12)] (0.19 g, 0.79 mmol) and 3,6-dichloropicolinic acid phenyl ester [Compound (IV-9)] (0.21 g, 0.79 mmol), the Compound (I-738) was synthesized according to the process of Synthesis Example 1.

White solid, m.p.: 137–138° C., yield: 0.276 g, percent yield: 84.1%. IR KBr cm$^{-1}$: 3298, 3220, 1722, 1443, 1398, 1251, 1179, 867. $^1$H-NMR (60 MHz, CDCl$_3$, δ): 7.1–7.7 (4H, m, aromatic ring H×3, pyridine ring H×1), 7.7 (1H, d, J=8 Hz, pyridine ring H×1), 8.1–8.3 (1H, m, aromatic ring H), NH indistinctness.

Synthesis Example 72
Synthesis of 6-Chloro-4-methyl-N-[(2-trifluoromethoxyphenyl)sulfonyl]-2-pyridinecarboxamide [Compound (I-728)]

Using 2-trifluoromethoxyphenylsulfonamide [Compound (III-12)] (0.195 g, 0.81 mmol) and 6-chloro-4-methylpicolinic acid phenyl ester [Compound (IV-8)] (0.2 g, 0.81 mmol), the compound (I-728) was synthesized according to the process of Synthesis Example 1.

White solid, m.p.: 135–138° C., yield: 0.278 g, percent yield: 86.8%. IR KBr cm$^{-1}$: 3352, 1728, 1599, 1455, 1428, 1353, 1293, 1257, 1179, 1071, 858, 588. $^1$H-NMR (60 MHz, CDCl$_3$, δ): 2.3 (3H, s, CH$_3$), 7.1–7.7 (5H, m, aromatic ring H×3, pyridine ring H×2), 7.9–8.3 (1H, m, aromatic ring H), NH indistinctness.

Synthesis Example 73
Synthesis of 6-Chloro-4-methyl-N-[[2-(N,N-dimethylaminosulfonyl)phenyl]sulfonyl]-2-pyridinecarboxamide [Compound (I-820)]

Using 2-(N,N-dimethylaminosulfonyl)phenylsulfonamide [Compound (III-13)] (0.32 g, 1.21 mmol) and 6-chloro-4-methylpicolinic acid phenyl ester [Compound (IV-8)] (0.3 g, 1.21 mmol), the Compound (I-820) was synthesized according to the process of Synthesis Example 1.

White solid, m.p.: 207–208° C., yield: 0.45 g, percent yield: 90.2%. IR KBr cm$^{-1}$: 1716, 1605, 1428, 1347, 1194, 1164, 966. $^1$H-NMR (60 MHz, CDCl$_3$, δ): 2.3 (3H, s, CH$_3$), 2.9 [6H, s, N(CH$_3$)$_2$], 7.0–7.9 (6H, m, aromatic ring H×4, pyridine ring H×2), NH indistinctness.

Synthesis Example 74
Synthesis of 2-[[[(6-Chloro-4-methylpyridin-2-yl)carbonyl]-amino]sulfonyl]benzoic Acid Methyl Ester [Compound (I-188)]

Using 2-methoxycarbonylphenylsulfonamide [Compound (III-3)] (0.174 g, 0.808 mmol), 6-chloro-4-methylpicolinic acid phenyl ester [Compound (IV-8)] (0.2 g, 0.808 mmol) and potassium carbonate (0.11 g, 0.808 mmol), the Compound (I-188) was synthesized according to the process of Synthesis Example 1.

White solid, m.p.: 160–163° C., yield: 0.17 g, percent yield: 57.2%. IR KBr cm$^{-1}$: 3352, 1725, 1602, 1446, 1356, 1299, 1176, 1140, 1122, 888. $^1$H-NMR (60 MHz, CDCl$_3$, δ): 2.4 (3H, s, CH$_3$), 4.0 (3H, s, COOCH$_3$), 7.1–7.8 (5H, m, aromatic ring H×3, pyridine ring H×2), 8.1–8.4 (1H, m, aromatic ring H), NH indistinctness.

Synthesis Example 75
Synthesis of 6-Chloro-N-[(2,6-dichlorophenyl)sulfonyl]-4-methyl-2-pyridinecarboxamide [Compound (I-548)]

Using 2,6-dichlorophenylsulfonamide [Compound (III-7) (0.183 g, 0.81 mmol)] and 6-chloro-4-methylpicolinic acid phenyl ester [Compound (IV-8)] (0.2 g, 0.81 mmol), the Compound (I-548) was synthesized according to the process of Synthesis Example 1.

White solid, m.p.: 182–183° C., yield: 0.27 g, percent yield: 88.4%. IR KBr cm$^{-1}$: 1734, 1431, 1398, 1362, 1176, 1134, 786, 603. $^1$H-NMR (60 MHz, CDCl$_3$, δ): 2.4 (3H, s, CH$_3$), 7.1–7.7 (5H, m, aromatic ring H×3, pyridine ring H×2), NH indistinctness.

Synthesis Example 76
Synthesis of N-[[2-(N,N-Dimethylaminosulfonyl)phenyl]-sulfonyl]-4-methyl-6-methoxy-2-pyridinecarboxamide [Compound (I-878)]

(1) Synthesis of 2-cyano-4-methyl-6-methoxy-2-pyridine

To 10 ml of dry DMF was added 4 ml of dry methanol, and was then added sodium hydride (60% in mineral oil, 0.524 g, 13.1 mmol) thereto. After conclusion of bubbling, a solution of 6-chloro-2-cyano-4-methylpyridine (2 g, 13.1 mmol) in 10 ml of dry DMF was added to the mixture, followed by stirring at 100° C. for 5 hours. The reaction solution was poured into 40 ml of water. The resulted solid precipitate was filtered out, washed with water and extracted the aqueous layer with ethyl acetate. The precipitate and the extract were collected and purified by silica gel column chromatography (ethyl acetate:n-hexane=1:5) to obtain a solid.

White solid, m.p.: 98–100° C., yield: 0.77 g, percent yield: 39.7%. IR KBr cm$^{-1}$: 2962, 2260, 1620, 1566, 1476, 1359, 1209, 1062, 861, 660. $^1$H-NMR (60 MHz, CDCl$_3$, δ): 2.3 (3H, s, CH$_3$), 3.8 (3H, s, OCH$_3$), 6.6 (1H, s, pyridine ring H), 7.0 (1H, s, pyridine ring H).

(2) Synthesis of 4-methyl-6-methoxy-2-pyridinecarboxylic acid phenyl ester [Compound (IV-6)]

To 2-cyano-4-methyl-6-methoxypyridine (0.76 g, 5.1 mmol) was added 5 ml of concentrated hydrochloric acid, followed by stirring at 100° C. for 1 hour. The reaction solution was then distilled off and the resultant solid precipitate was filtered out, washed with water and dried to obtain 0.85 g 4-methyl-6-methoxy-2-pyridin-carboxylic acid.

It was suspended in 20 ml dry benzene containing a catalytic amount of dry DMF. After addition of thionyl chloride (3 g, 5.1×5 mmol), the suspension was refluxed for 1 hour. After an excess amount of thionyl chloride and the solvent were distilled off, 4 ml of dry dichloromethane was added to the residue.

The resultant solution was added under cooling with water to a solution of phenol (0.48 g, 5.1 mmol) and triethylamine (0.56 g, 5.1×1.1 mmol) in 10 ml of dry dichloromethane. After stirring at room temperature for 1.5 hours, the reaction solution was distributed by adding 20 ml of 5% aqueous hydrochloric acid solution. The organic layer was washed with saturated saline solution and dried with sodium sulfate.

After removed the solvent by distillation, the residue was purified by silica gel column chromatography (ethyl acetate:n-hexane=1:10) to give a liquid.

Light yellow liquid, yield: 0.39 g, percent yield: 31.4%. IR NaCl liq. film cm$^{-1}$: 1743, 1620, 1569, 1497, 1470, 1362, 1278, 1242, 1197, 1056, 738. $^1$H-NMR (60 MHz, CDCl$_3$, δ): 2.3 (3H, s, CH$_3$), 3.9 (3H, s, OCH$_3$), 6.5–6.8 (1H, s, pyridine ring H), 6.8–7.3 (5H, m, aromatic ring H×5), 7.5 (1H, s, pyridine ring H).

(3) Synthesis of N-[[2-(N,N-dimethylaminosulfonyl)phenyl]-sulfonyl]-4-methyl-6-methoxy-2-pyridinecarboxamide [Compound (I-878)]

Using 2-(N,N-dimethylaminosulfonyl)phenylsulfonamide [Compound (III-13)] (0.217 g, 0.82 mmol) and 4-methyl-6-methoxy-2-pyridinecarboxylic acid phenyl ester [Compound (IV-6)] (0.2 g, 0.82 mmol), the Compound (I-878) was synthesized according to the process of Synthesis Example 1.

White solid, m.p.: 161–163° C., yield: 0.278 g, percent yield: 81.7%. IR KBr cm$^{-1}$: 1392, 1347, 1194, 1164, 867. $^1$H-NMR (60 MHz, d$_6$-DMSO, δ): 2.3 (3H, s, CH$_3$), 3.9 (3H, s, OCH$_3$), 6.8 (1H, pyridine ring H), 7.3 (1H, s, pyridine ring H), 7.6–7.9 (3H, m, aromatic ring H), 8.0–8.5 (1H, m, aromatic ring H), NH indistinctness.

Formulation examples and tests will hereinafter be described. The vehicles (diluents) and aids, their mixing ratios and effective components can vary in wide ranges. The term "parts" in each Formulation Examples means parts by weight:

Formulation Example 1 (Wettable Powder)

| | |
|---|---|
| Compound (I-255) | 50 parts |
| Sodium ligninsulfonate | 5 parts |
| Sodium alkylsulfonate | 3 parts |
| Diatomaceous earth | 42 parts |

The above ingredients are mixed and ground into a wettable powder, which is used by diluting with water.

Formulation Example 2 (Emulsion)

| | |
|---|---|
| Compound (I-615) | 25 parts |
| Xylene | 65 parts |
| Polyoxyethylene alkylaryl ether | 10 parts |

The above ingredients are mixed intimately into an emulsion, which is used by diluting with water.

Formulation Example 3 (Granule)

| | |
|---|---|
| Compound (I-888) | 8 parts |
| Bentonite | 40 parts |
| Clay | 45 parts |
| Calcium ligninsulfonate | 7 parts |

The above ingredients are mixed intimately and kneaded with addition of water, and then formed into granules by an extruding granulator.

Test Example 1

Test on Herbicidal Activity by Foliar Application:

Herbicidal solutions of each test compounds, which were prepared by dissolving at predetermined concentrations such a wettable powder of the test compound as that described in the above Formulation Example, were sprayed at dosages of 1 kg/ha over foliar parts of Amaranthus retroflexus, Bidens pilosa, Sinapis arvensis, Stellaria media, Solanum nigrum, Abutilon theophrasti, Convolvulus arvensis, Matricaria chamomilla, Galium aparine, Veronica hederaefolia, and Setaria viridis (each test plant is 1–2 leaf stage) which were grown in pots. 14 days latter after spraying, its herbicidal activity was evaluated in accordance with the below-described system.

Herbicidal Activity

1: less than 30% inhibition
2: 30% or more–50% inhibition
3: 50% or more–70% inhibition
4: 70% or more–90% inhibition
5: 90% or more inhibition The results are summarized in Table 4.

TABLE 4

| Compound No. | Application Dosage (kg/ha) | Amaranthus retroflexus | Bidens pilosa | Sinapis arvensis | Stellaria media | Solanum nigrum | Abutilon theophrasti | Convolvulus arvensis | Matricaria chamomilla | Galium aparine | Veronica hederaefolia | Setaria viridis |
|---|---|---|---|---|---|---|---|---|---|---|---|---|
| I-054 | 1 | 3 | 5 | 5 | 5 | 4 | 2 | 3 | 5 | 4 | 4 | 5 |
| I-221 | 1 | 5 | 4 | 5 | 4 | 5 | 4 | 4 | 2 | 5 | 4 | 3 |
| I-231 | 1 | 5 | 5 | 5 | 5 | 5 | 5 | 4 | 5 | 5 | 5 | 5 |
| I-234 | 1 | 5 | 5 | 5 | 5 | 5 | 5 | 4 | 5 | 4 | 4 | 4 |
| I-245 | 1 | 5 | 5 | 5 | 4 | 5 | 5 | 3 | 3 | 4 | 4 | 3 |
| I-254 | 1 | 5 | 5 | 5 | 5 | 5 | 5 | 3 | 3 | 5 | 5 | 4 |
| I-255 | 1 | 4 | 5 | 5 | 5 | 5 | 5 | 5 | 5 | 5 | 5 | 4 |
| I-258 | 1 | 5 | 5 | 5 | 5 | 5 | 5 | 5 | 5 | 5 | 4 | 5 |
| I-259 | 1 | 5 | 4 | 5 | 5 | 4 | 5 | 3 | 4 | 5 | 4 | 4 |
| I-265 | 1 | 5 | 5 | 5 | 5 | 5 | 5 | 3 | 5 | 4 | 3 | 4 |
| I-345 | 1 | 3 | 5 | 5 | 4 | 5 | 2 | 5 | 4 | 4 | 3 | 2 |
| I-557 | 1 | 5 | 5 | 5 | 5 | 5 | 5 | 5 | 5 | 5 | 5 | 5 |
| I-581 | 1 | 5 | 5 | 5 | 5 | 5 | 4 | 4 | 5 | 5 | 4 | 4 |
| I-591 | 1 | 5 | 5 | 5 | 5 | 5 | 5 | 5 | 5 | 5 | 5 | 1 |
| I-594 | 1 | 2 | 4 | 5 | 5 | 2 | 4 | 2 | 4 | 4 | 4 | 2 |
| I-615 | 1 | 4 | 5 | 5 | 5 | 5 | 5 | 4 | 5 | 5 | 4 | 4 |
| I-618 | 1 | 2 | 5 | 5 | 5 | 5 | 5 | 3 | 5 | 4 | 5 | 2 |
| I-705 | 1 | 4 | 5 | 5 | 5 | 4 | 2 | 5 | 4 | 4 | 4 | 3 |
| I-771 | 1 | 5 | 5 | 5 | 5 | 5 | 5 | 4 | 5 | 5 | 5 | 1 |
| I-774 | 1 | 4 | 5 | 5 | 5 | 5 | 5 | 4 | 5 | 4 | 5 | 5 |

TABLE 4-continued

| Compound No. | Application Dosage (kg/ha) | Amaranthus retroflexus | Bidens pilosa | Sinapis arvensis | Stellaria media | Solanum nigrum | Abutilon theophrasti | Convolvulus arvensis | Matricaria chamomilla | Galium aparine | Veronica hederaefolia | Setaria viridis |
|---|---|---|---|---|---|---|---|---|---|---|---|---|
| I-778 | 1 | 4 | 5 | 5 | 3 | 5 | 5 | 5 | 5 | 4 | 2 | 3 |
| I-795 | 1 | 4 | 5 | 5 | 5 | 5 | 4 | 3 | 5 | 5 | 5 | 2 |
| I-798 | 1 | 5 | 5 | 5 | 5 | 5 | 5 | 4 | 5 | 5 | 5 | 3 |
| I-799 | 1 | 3 | 4 | 5 | 5 | 4 | 5 | 3 | 5 | 4 | 4 | 3 |
| I-805 | 1 | 5 | 5 | 5 | 5 | 5 | 5 | 5 | 5 | 5 | 4 | 4 |
| I-818 | 1 | 5 | 5 | 5 | 5 | 5 | 4 | 5 | 5 | 5 | 4 | 5 |
| I-819 | 1 | 5 | 5 | 5 | 5 | 5 | 5 | 4 | 5 | 4 | 3 | 5 |
| I-830 | 1 | 5 | 5 | 5 | 5 | 5 | 5 | 5 | 5 | 5 | 5 | 4 |
| I-838 | 1 | 4 | 5 | 5 | 4 | 5 | 5 | 5 | 5 | 5 | 4 | 5 |
| I-858 | 1 | 5 | 5 | 5 | 5 | 5 | 5 | 5 | 4 | 5 | 4 | 5 |
| I-859 | 1 | 5 | 5 | 5 | 5 | 5 | 5 | 4 | 5 | 5 | 5 | 5 |
| I-861 | 1 | 5 | 5 | 5 | 5 | 5 | 5 | 5 | 5 | 5 | 4 | 5 |
| I-864 | 1 | 3 | 5 | 5 | 5 | 4 | 5 | 3 | 5 | 4 | 4 | 4 |
| I-868 | 1 | 3 | 5 | 5 | 4 | 4 | 3 | 3 | 2 | 5 | 3 | 3 |
| I-885 | 1 | 5 | 5 | 5 | 5 | 5 | 5 | 5 | 5 | 5 | 4 | 5 |
| I-888 | 1 | 5 | 5 | 5 | 5 | 5 | 5 | 5 | 5 | 5 | 4 | 5 |
| I-889 | 1 | 5 | 5 | 5 | 5 | 4 | 5 | 4 | 5 | 5 | 3 | 4 |
| I-895 | 1 | 5 | 5 | 5 | 5 | 5 | 5 | 5 | 5 | 5 | 5 | 5 |
| I-975 | 1 | 3 | 5 | 5 | 4 | 5 | 5 | 4 | 4 | 5 | 3 | 3 |

Industrial Applicability

The N-phenylsulfonylpicolinamide derivatives of the above formula (I) according to the present invention exhibit a certain herbicidal effect in a low dosage and have a selectivity between crops and weeds. Accordingly, the herbicidal composition according to the present invention which comprises this compound as an active ingredient is particularly suitable, e.g., for preventing monocotyledon and dicotyledon weeds important crops, such as wheat, rice, corn, soybean, etc. The composition can be applied in areas such as farming areas, inclusive of farms, paddy fields, and orchards, as well as non-farming areas, inclusive of grounds and industrial sites.

What is claimed is:

1. An N-(phenylsulfonyl)picolinamide derivative of the following formula (I'):

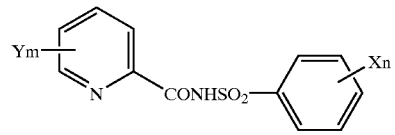

(I')

wherein
X represents halogen atom, C1–C4 alkyl group, C1–C4 haloalkyl group, C1–C4 alkoxy group, C1–C4 haloalkoxy group, (C1–C4 alkoxy)carbonyl group, (di-C1–C4 alkylamino)sulfonyl group, (N—(C1–C4 alkyl)-N—(C1–C4 alkoxy)amino)sulfonyl group, (C1–C4 alkylamino)-sulfonyl group, C1–C4 alkylthio group, C1–C4 alkylsulfinyl group, C1–C4 alkylsulfonyl group or nitro group;

n is an integer of 0–3, each X may be identical or different in case of n being 2 or more;

Y represents halogen atom, C1–C4 alkyl group, C1–C4 haloalkyl group, C1–C4 alkoxy group, C1–C4 haloalkoxy group, C1–C4 alkylthio group, C1–C4 haloalkylthio group, amino group, C1–C4 alkylamino group, di-C1–C4 alkylamino group, (C1–C4 alkoxy) C1–C4 alkyl group, (C1–C4 alkylthio) C1–C4 alkyl group or nitro group; and m is an integer of 0–2, each Y may be identical or different in case of m being 2;

with the proviso that X is not a methyl group at the para position in formula (I') when n is 1 and m is 0.

2. A herbicide composition including an active ingredient comprising the N-(phenylsulfonyl)picolinamide derivative according to claim 1 in admixture with a suitable herbicide preparation aid.

* * * * *